(12) United States Patent
Stuyver

(10) Patent No.: US 6,803,187 B1
(45) Date of Patent: Oct. 12, 2004

(54) METHOD FOR DETECTION OF DRUG-SELECTED MUTATIONS IN THE HIV PROTEASE GENE

(75) Inventor: Lieven Stuyver, Herzele (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/720,435

(22) PCT Filed: Jun. 22, 1999

(86) PCT No.: PCT/EP99/04317

§ 371 (c)(1),
(2), (4) Date: Jun. 25, 2001

(87) PCT Pub. No.: WO99/67428

PCT Pub. Date: Dec. 29, 1999

(30) Foreign Application Priority Data

Jun. 24, 1998 (EP) .............................. 98870143

(51) Int. Cl.⁷ ................................................. C12Q 1/20
(52) U.S. Cl. ......................... 435/5; 435/91.2; 536/24.3; 536/24.32
(58) Field of Search .................... 435/5, 91.2; 536/24.3, 536/24.32

(56) References Cited

PUBLICATIONS

Eastman 1998, J Virol. 72 (6) pp. 5154–5164.*

* cited by examiner

*Primary Examiner*—Jeffrey Fredman
*Assistant Examiner*—Juliet C. Switzer

(74) *Attorney, Agent, or Firm*—Howrey Simon Arnold & White, LLP

(57) ABSTRACT

The present invention relates to a method for the rapid and reliable detection of drug-selected mutations in the HIV protease gene allowing the simultaneous charaterization of a range of codons involved in drug resistance using specific sets of probes optimized to function together in a reverse-hybridization assay. More particularly, the present invention relates to a method for determining the susceptibility to antiviral drugs of HIV viruses in a biological sample, with said method comprising: a) if need be, releasing, isolating or concentrating the polynucleic acids present in the sample; b) if need be amplifying the relevant part of the protease gene of HIV with at least one suitable primer pair; c) hybrydizing the polynucleic acids of step a) or b) with at least one of the following probes: probes specifically hybridizing to a target sequence comprising codon 30; probes specifically hybridizing to a target sequence comprising codon 46 and/or 48; probes specifically hybridizing to a target sequence comprising codon 50; probes specifically hybridizing to a target sequence comprising codon 54; probes specifically hybridizing to a target sequence comprising codon 82 and/or 84; probes specifically hybridizing to a target sequence comprising codon 90; or the complement of said probes; further characterized in that said probes specifically hybridize to any of the target sequences presented in FIG. (1), or the complement of said target sequences; d) inferring from the result of step c) whether or not a mutation giving rise to drug resistance is present in any of said target sequences.

11 Claims, 21 Drawing Sheets

Figure 1

Codon 30

Figure 2A:
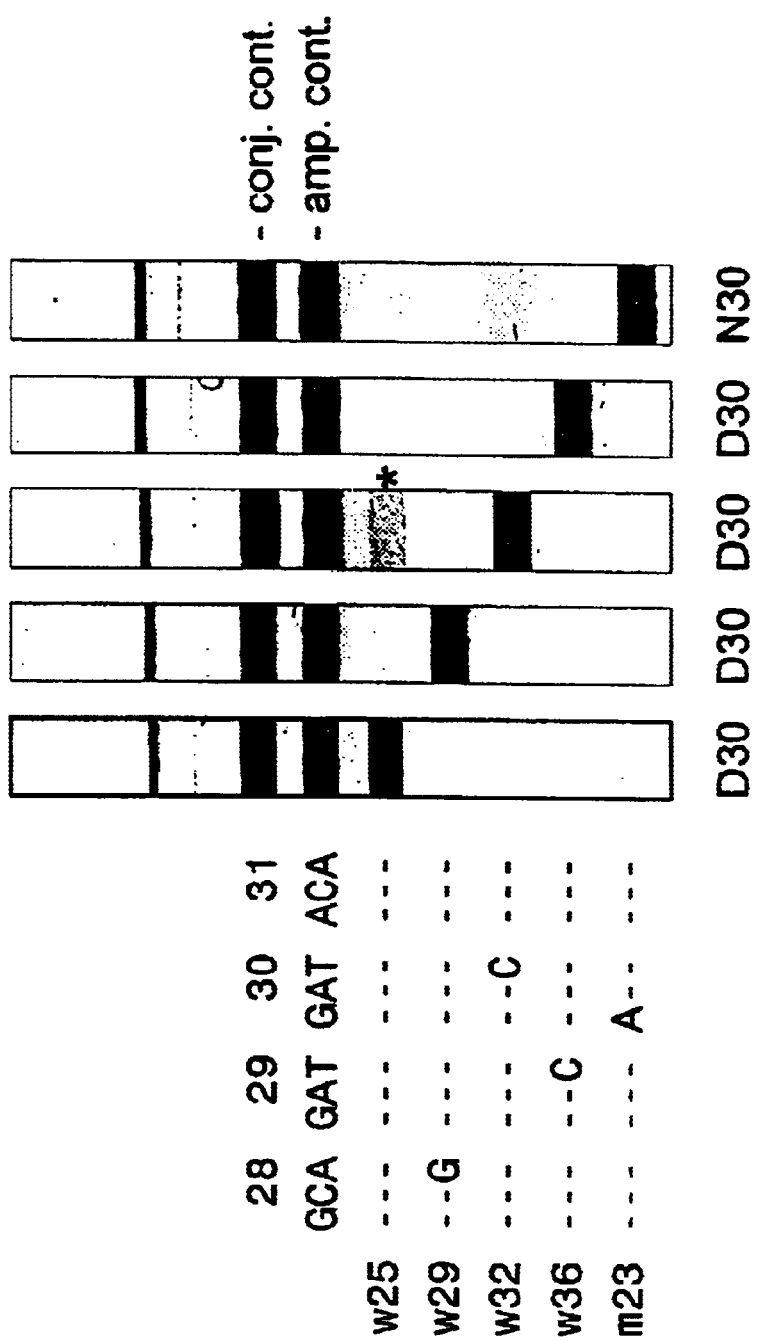

| 26 | 27 | 28 | 29 | 30 | 31 | 32 | 33 | 34 | 35 |
|---|---|---|---|---|---|---|---|---|---|
| ACA | GGA | GCA | GAT | GAT | ACA | GTA | TTA | GAA | GAA |
|  | G | G | C | A |  | A | G |  |  |
|  |  |  |  | C |  | G | G |  |  |
|  |  |  |  |  |  | C |  |  |  |
|  |  |  |  |  |  | C |  |  |  |
|  |  |  |  |  |  | G |  |  |  |

Codon 46/48

| 44 | 45 | 46 | 47 | 48 | 49 | 50 | 51 | 52 | 53 | 54 |
|---|---|---|---|---|---|---|---|---|---|---|
| CCA | AAA | ATG | ATA | GGG | GGA | ATT | GGA | GGT | TTT | ATC |
|  | G | T | G | T | A | G |  | G | GG |  |
|  | G | A |  | A | G | G |  |  | G |  |
|  |  |  |  |  |  |  |  |  | G |  |

Codon 50

| 45 | 46 | 47 | 48 | 49 | 50 | 51 | 52 | 53 | 54 |
|---|---|---|---|---|---|---|---|---|---|
| AAA | ATG | GTA | GGG | GGA | ATT | GGA | GGT | TTT | ATC |
|  |  | T |  |  | G | C | G | G | G |
|  |  | A |  |  |  | G | C | G | G |
|  |  |  |  |  |  |  |  | G | T |
|  |  |  |  |  |  |  |  | C | GC |
|  |  |  |  |  |  |  |  | GG |  |
|  |  |  |  |  |  |  |  | GG |  |

Codon 54

| 51 | 52 | 53 | 54 | 55 | 56 | 57 | 58 |
|---|---|---|---|---|---|---|---|
| GGA | GGT | TTT | ATC | AAA | GTA | AGA | CAG |
| G | C | C | G | G | C | A | G |
|  | G | A | C | G |  | G | A |
|  |  |  | T |  |  |  |  |
|  |  |  | GC |  |  |  |  |

Figure 1 - Cont'd

Codon 82/84

| 78 | 79 | 80 | 81 | 82 | 83 | 84 | 85 | 86 | 87 |
|----|----|----|----|----|----|----|----|----|----|
| GGA | CCT | ACA | CCT | GTC | AAC | ATA | ATT | GGA | AGA |
|  | A | T |  | T | C | G | G |  |  |
|  | G |  | T | A |  | T | G |  |  |
|  |  | G |  | C |  |  | GG |  |  |
|  |  |  | A | T |  |  | C |  |  |
|  |  |  |  | AC |  |  |  |  |  |
|  |  |  |  | TC |  |  |  |  |  |

Codon 90

| 86 | 87 | 88 | 89 | 90 | 91 | 92 | 93 | 94 |
|----|----|----|----|----|----|----|----|----|
| GGA | AGA | AAT | CTG | TTG | ACT | CAG | ATT | GGT |
| C |  | C | A | A | C | A | C | G |
|  | A |  | T | C |  | A | G | C |
|  | G |  | C | A |  |  | G | A |
|  |  |  | A | AA |  |  | A |  |
|  |  |  | A A |  |  |  | GG |  |
|  |  |  |  |  |  |  | C G |  |

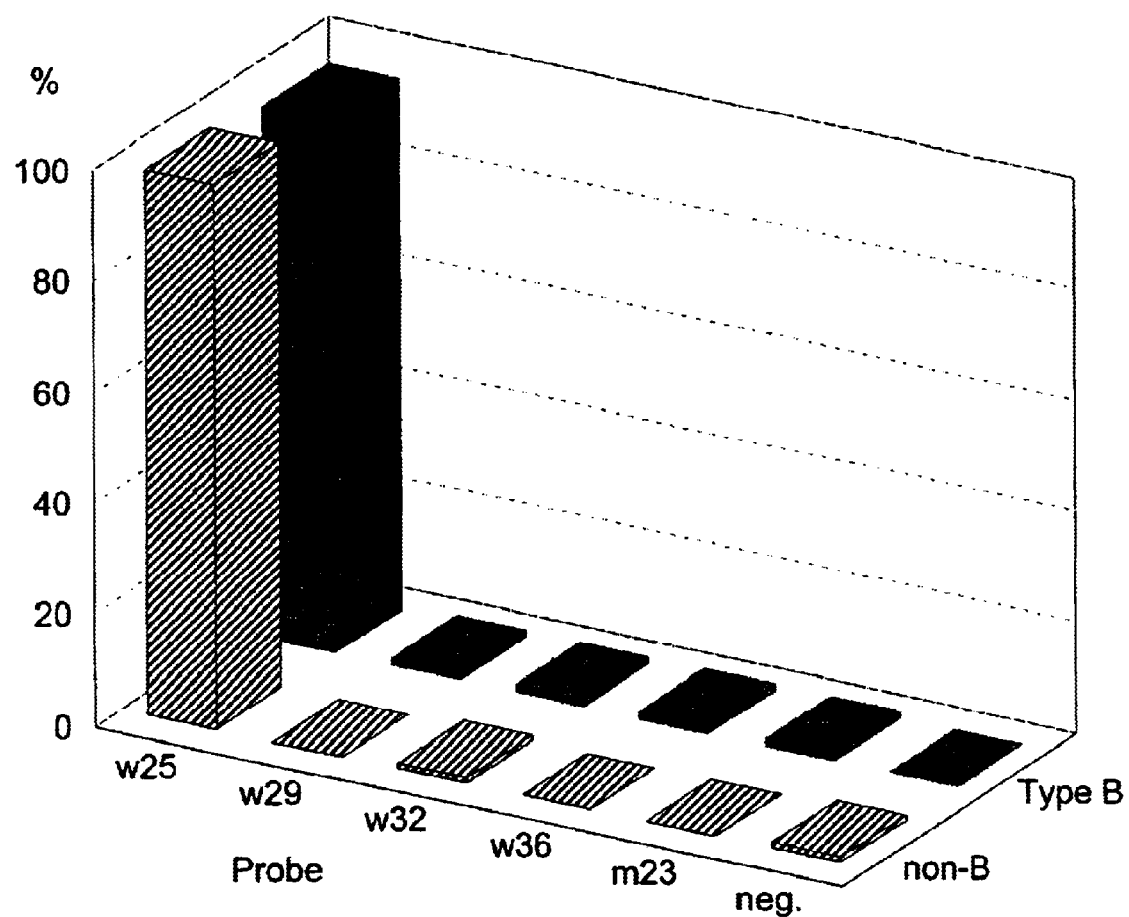

METHOD FOR DETECTION OF DRUG-SELECTED MUTATIONS IN THE HIV PROTEASE GENE

This application is a §371 national stage filing of PCT/EP99/04317, filed 22 Jun. 1999 (published in English on 29 Dec. 1999 as WO 99/67428) and claiming priority to EP 98870143.9 filed 24 Jun. 1998.

1. FIELD OF THE INVENTION

The present invention relates to the field of HIV diagnosis. More particularly, the present invention relates to the field of diagnosing the susceptibility of an HIV sample to antiviral drugs used to treat HIV infection.

The present invention relates to a method for the rapid and reliable detection of drug-selected mutations in the HIV protease gene allowing the simultaneous characterization of a range of codons involved in drug resistance using specific sets of probes optimized to function together in a reverse-hybridization assay.

2. BACKGROUND OF THE INVENTION

The human immunodeficiency virus (HIV) is the ethiological agent for the acquired immunodeficiency syndrome (AIDS). HIV, like other retroviruses, encodes an aspartic protease that mediates the maturation of the newly produced viral particle by cleaving viral polypeptides into their functional forms (Hunter et al). The HIV protease is a dimeric molecule consisting of two identical subunits each contributing a catalytic aspartic residue (Navia et al, Whodawer et al, Meek et al). Inhibition of this enzyme gives rise to noninfectious viral particles that cannot establish new cycles of viral replication (Kohl et al, Peng et al).

Attempts to develop inhibitors of HIV-1 protease were initially based on designing peptide compounds that mimicked the natural substrate. The availability of the 3-dimensional structure of the enzyme have more recently allowed the rational design of protease inhibitors (PI) using computer modeling (Huff et al, Whodawer et al). A number of second generation PI that are partially peptidic or entirely nonpeptidic have proven to exhibit particularly potent antiviral effects in cell culture. Combinations of various protease inhibitors with nucleoside and non-nucleoside RT inhibitors have also been studied extensively in vitro. In every instance, the combinations have been at least additive and usually synergistic.

In spite of the antiviral potency of many recently developed HIV-1 PI, the emergence of virus variants with decreased sensitivity to these compounds has been described both in cell culture and in treated patients thereby escaping the inhibitory effect of the antiviral (Condra et al.). Emergence of resistant variants depends on the selective pressure applied to the viral population. In the case of a relatively ineffective drug, selective pressure is low because replication of both wild-type virus and any variants can continue. If a more effective drug suppresses replication of virus except for a resistant variant, then that variant will be selected. Virus variants that arise from selection by PI carry several distinct mutations in the protease coding sequence that appear to emerge sequentially. A number of these cluster near the active site of the enzyme while others are found at distant sites. This suggests conformational adaptation to primary changes in the active site and in this respect certain mutations that increase resistance to PI also decrease protease activity and virus replication.

Amongst the PI, the antiviral activity of the PI ritonavir (A-75925; ABT-538), nelfinavir (AG-1343), indinavir (MK-639; L735; L524) and saquinavir (Ro 31-8959) have been approved by the Food and Drug Administration and are currently under evaluation in clinical trials involving HIV-infected patients. The VX-487 (141W94) antiviral compound is not yet approved. The most important mutations selected for the above compounds and leading to gradually increasing resistance are found at amino acid (aa) positions 30 (D to N), 46 (M to I), 48 (G to V), 50 (I to V), 54 (I to A, I to V), 82 (V to A, or F, or I, or T), 84 (I to V) and 90 (L to M). Other mutations associated with drug resistance to the mentioned compounds have been described (Schinazi et al). Saquinavir-resistant variants, which usually carry mutations at amino acid positions 90 and/or 48, emerge in approximately 45% of patients after 1 year of monotherapy. Resistance appears to develop less frequently with higher doses of saquinavir. Resistance to indinavir and ritonavir requires multiple mutations; usually at greater than 3 and up to 11 sites, with more amino acid substitutions conferring higher levels of resistance. Resistant isolates usually carry mutations at codons 82, 84, or 90. In the case of ritonavir, the mutation at codon 82 appears fist in most patients. Although mutant virions resistant to saquinavir are not cross-resistant to indinavir or ritonavir, isolates resistant to indinavir are generally ritonavir resistant and visa versa. Resistance to either indinavir or ritonavir usually results in cross-resistance to saquinavir. Approximately one third of indinavir resistant isolates are cross-resistant to nelfinavir as well.

The regime for an efficient antiviral treatment is currently not clear at all. Patterns of reduced susceptibility to HIV protease inhibitors have been investigated in vitro by cultivating virus in the presence of PI. These data, however, do not completely predict the pattern of amino-acid changes actually seen in patients receiving PI. Knowledge of the resistance and cross-resistance patterns should facilitate selection of optimal drug combinations and selection of sequences with non-overlapping resistance patterns. This would delay the emergence of cross-resistant viral strains and prolong the duration of effective antiretroviral activity in patients. Therefore, there is need for methods and systems that detect these mutational events in order to give a better insight into the mechanisms of HIV resistance. Further, there is need for methods and systems which can provide data important for the antiviral therapy to follow in a more time-efficient and economical manner compared to the conventional cell-culture selection techniques.

3. AIMS OF THE INVENTION

It is an aim of the present invention to develop a rapid and reliable detection method for determination of the antiviral drug resistance of viruses, which contain protease genes such as HIV retroviruses present in a biological sample.

More particularly it is an aim of the present invention to provide a genotyping assay allowing the detection of the different HIV protease gene wild type and mutation codons involved in the antiviral resistance in one single experiment.

It is also an aim of the present invention to provide an HIV protease genotyping assay or method which allows to infer the nucleotide sequence at codons of interest and/or the amino acids at the codons of interest and/or the antiviral drug selected spectrum, and possibly also infer the HIV type or subtype isolate involved.

Even more particularly it is an aim of the present invention to provide a genotyping assay allowing the detection of the different HIV protease gene polymorphisms representing wild-type and mutation codons in one single experimental setup.

It is another aim of the present invention to select particular probes able to discriminate wild-type HIV protease sequences from mutated or polymorphic HIV protease sequences conferring resistance to one or more antiviral drugs, such as ritonavir (A-75925; ABT-538), nelfinavir (AG-1343), indinavir (MK-639; L735; L524), saquinavir (Ro 31-8959) and VX-478 (141W94) or others (Shinazi et al).

It is more particularly an aim of the present invention to select particular probes able to discriminate wild-type HIV protease sequences from mutated or polymorphic HIV protease sequences conferring resistance to ritonavir (A-75925; ABT-538).

It is more particularly an aim of the present invention to select particular probes able to discriminate wild-type HIV protease sequences from mutated HIV protease sequences conferring resistance to nelfinavir (AG-1343).

It is more particularly an aim of the present invention to select particular probes able to discriminate wild-type HIV protease sequences from mutated HIV protease sequences conferring resistance to indinavir (MK-639; L735; L524).

It is more particularly an aim of the present invention to select particular probes able to discriminate wild-type HIV protease sequences from mutated HIV protease sequences conferring resistance to saquinavir (Ro 31-8959).

It is more particularly an aim of the present invention to select particular probes able to discriminate wild-type HIV protease sequences from mutated HIV protease sequences conferring resistance to VX-478 (141W94).

It is also an aim of the present invention to select particular probes able to determine and/or infer cross-resistance to HIV protease inhibitors.

It is more particularly an aim of the present invention to select particular probes able to discriminate wild-type HIV protease from mutated HIV protease sequences involving at least one of amino acid positions 30 (D to N), 46 (M to I), 48 (G to V), 50 (I to V), 54 (I to A or V), 82 (V to A or F or I or T), 84(I to V) and 90 (L to M) of the viral protease gene.

It is particularly an aim of the present invention to select a particular set of probes, able to discriminate wild-type HIV protease sequences from mutated HIV protease sequences conferring resistance to any of the antiviral drugs defined above with this particular set of probes being used in a reverse hybridization assay.

It is moreover an aim of the present invention to combine a set of selected probes able to discriminate wild-type HIV protease sequences from mutated HIV protease sequences conferring resistance to antiviral drugs with another set of selected probes able to identify the HIV isolate, type or subtype present in the biological sample, whereby all probes can be used under the same hybridization and wash-conditions.

It is also an aim of the present invention to select primers enabling the amplification of the gene fragment(s) determining the antiviral drug resistance trait of interest.

It is also an aim of the present invention to select particular probes able to identify mutated HIV protease sequences resulting in cross-resistance to antiviral drugs.

The preset invention also aims at diagnostic kits comprising said probes useful for developing such a genotyping assay.

The present invention also aims at diagnostic kits comprising said primers useful for developing such a genotyping assay.

4. DETAILED DESCRIPTION OF THE INVENTION

All the aims of the present invention have been met by the following specific embodiments.

According to one embodiment, the present invention relates to a method for determining the susceptibility to antiviral drugs of HIV viruses in a biological sample, with said method comprising:

a) if need be, releasing, isolating or concentrating the polynucleic acids present in the sample;

b) if need be amplifying the relevant part of the protease gene of HIV with at least one suitable primer pair;

c) hybridizing the polynucleic acids of step a) or b) with at least one of the following probes:
   probes specifically hybridizing to a target sequence comprising codon 30;
   probes specifically hybridizing to a target sequence comprising codon 46 and/or 48;
   probes specifically hybridizing to a target sequence comprising codon 50;
   probes specifically hybridizing to a target sequence comprising codon 54;
   probes specifically hybridizing to a target sequence comprising codon 82 and/or 84;
   probes specifically hybridizing to a target sequence comprising codon 90;
   or the complement of said probes,
   further characterized in that said probes specifically hybridize to any of the target sequences presented in FIG. 1, or to the complement of said target sequences;

d) inferring from the result of step c) whether or not a mutation giving rise to drug resistance is present in any of said target sequences.

The numbering of HIV-1 protease gene encoded amino acids is as generally accepted in literature. Mutations that give rise to an amino acid change at position 48 or 90 are known to confer resistance to saquinavir (Eriebe et al; Tisdale et al). An amino acid change at codon 46 or 54 or 82 or 84 results in ritonavir and indinavir resistance (Kempf et al; Emini et al; Condra et al). Amino acid changes at positions 30 and 46 confer resistance to nelfinavir (Patick et al) and amino acid changes at position 50 confers resistance to VX-487 (Rao et al). Therefore, the method described above allows to determine whether a HIV strain is susceptible or resistant to any of the drugs mentioned above. This method can be used, for instance, to screen for mutations conferring resistance to any of the mentioned drugs before initiating therapy. This method may also be used to s for mutations that may arise during the course of therapy (i.e. monitoring of drug therapy). It is obvious that this method may also be used to determine resistance to drugs other than the above-mentioned drugs, provided that resistance to these other drugs is linked to mutations that can be detected by use of this method. This method may also be used for the specific detection of polymorphic nucleotides. It is to be understood that the said probes may only partly overlap with the targets sequences of FIG. 1, table 2 and table 3, as long as they allow for specific detection of the relevant polymorphic nucleotides as indicated above. The sequences of FIG. 1, table 2 and table 3 were derived from polynucleic acid fragments comprising the protease gene. These fragments were obtained by PCR amplification and were inserted into a cloning vector and sequence analyzed as described in example 1. It is to be noted that some polynucleic acid fragments comprised polymorphic nucleotides in their sequences, which have not been previously disclosed. These novel polymorphic nucleotide sequences are represented in table 4 below.

The present invention thus also relates to these novel sequences, or a fragment thereof, wherein said fragment consists of at least 10, preferably 15, even more preferably 20 contiguous nucleotides and contains at least one polymorphic nucleotide. It is furthermore to be understood that these new polymorphic nucleotides may also be expected to arise in another sequence context than in the mentioned sequences. For instance a G at the third position of codon 55 is shown in SEQ ID N° 478 m combination with a T at the third position of codon 54, but a G at the third position of codon 55 may also be expected to occur in the context of a wild type sequence. It is also to be understood that the above mentioned specifications apply to the complement of the said target sequences as well. This applies also to FIG. 1.

According to a preferred embodiment the present invention relates to a method as indicated above, further characterized in that said probes are capable of simultaneously hybridizing to their respective target regions under appropriate hybridization and wash conditions allowing the detection of the hybrids formed.

According to a preferred embodiment, step c is performed using a set of at least 2, preferably at least 3, more preferably at least 4 and most preferably at least 5 probes meticulously designed as such that they show the desired hybridization results. In general this method may be used for any purpose that relies on the presence or absence of mutations that can be detected by this method, e.g. for genotyping. The probes of table 1 have been optimized to give specific hybridization results when used in a LiPA assay (see below), as described in examples 2 and 3. These probes have thus also been optimized to simultaneously hybridize to their respective target regions under the same hybridization and wash conditions allowing the detection of hybrids. The sets of probes for each of the codons 30,46/48, 50, 54 and 82/84 have been tested experimentally as described in examples 2 and 3. The reactivity of the sets shown in table 1 with 856 serum samples from various geographic origins was evaluated. It was found that the sets of probes for codons 30, 46/48, 50, 54 and 82/84 reacted with 98.9%, 99.6%, 98.5%, 99.20%, 95.4% and 97.2% of the test samples, respectively. The present invention thus also relates to the sets of probes for codons 30, 46/48, 50, 54, 82/84 and 90, shown in table 1 and table 7.

According to another even more preferred embodiment, the present invention relates to a method as defined above, further characterized in that:

step b) comprises amplifying a fragment of the protease gene with at least one 5'-primer specifically hybridizing to a target sequence located between nucleotide position 210 and nucleotide position 260 (codon 87), more preferably between nucleotide position 220 and nucleotide position 260 (codon 87), more preferably between nucleotide position 230 and nucleotide position 260 (codon 87), even more preferably at nucleotide position 241 to nucleotide position 260 (codon 87) in combination with at least one suitable 3'-primer, and step c) comprises hybridizing the polynucleic acids of step a) or b) with at least one of the probes specifically hybridizing to a target sequence comprising codon 90.

According to another even more preferred embodiment, the present invention relates to a method as defined above, further characterized in that:

step b) comprises amplifying a fragment of the protease gene with at least one 3'-primer specifically hybridizing to a target sequence located between nucleotide position 253 (codon 85) and nucleotide positions 300, more preferably between nucleotide position 253 (codon 85) and nucleotide positions 290, more preferably between nucleotide position 253 (codon 85) and nucleotide positions 280, even more preferably at nucleotide position 253 (codon 85) to nucleotide position 273 (codon 91), in combination with at least one suitable 5'-primer, and step c) comprises hybridizing the polynucleic acids of step a) or b) with at least one of the probes specifically hybridizing to a target sequence comprising any of codons 30, 46, 48, 50, 52, 54, 82 and 84.

It has been found, unexpectedly, that an amplified nucleic acid fragment comprising all of the above-mentioned codons, does not hybridize optimally to probes comprising codon 82, 84 or 90. On the other hand, a shorter fragment, for instance the fragment which is amplified by use of the primers Prot41bio and Prot6bio with respectively seq id no 5 and seq id no 4; hybridizes better to probes comprising codon 90. Better hybridization is also obtained when the fragment is amplified with primer Prot41bio in combination with primers Prot6abio, Prot6bbio, Prot6cbio and Prot6dbio. The present invention thus also relates to a method as defined above, finder characterized in that the 5'-primer is seq id no 5 and at least one 3' primer is chosen from seq id no 4, seq id no506, seq id no 507, seq id no 508, and seq id 509. Likewise, another shorter fragment, for instance the fragment which is amplified by use of the primers Prot2bio and Prot31bio with respectively seq id no 3 and seq id no 6, was found to hybridize better to probes comprising codon 82 and/or 84. Hence the present invention also relates to a method as defined above, further characterized in that the 5'-primer is seq id no 5 and at least one 3'-primer is chosen from seq id no 4, seq id no506, seq id no 507, seq id no 508, and seq id no 509.

New sets of amplification primers as mentioned in example 1 were selected. The present invention thus also relates to primers: prot16 (SEQ ID NO 501), prot5 (SEQ ID NO 5), prot2abio (SEQ ID NO 503), prot2bbio (SEQ ID NO 504), prot31bio (SEQ ID NO 6), prot41-bio (SEQ ID NO 505), prot6a (SEQ ID NO 506), prot6b (SEQ ID NO 507), prot6c (SEQ ID NO 508) and prot6d (SEQ DID NO 509). A number of these primers are chemically modified (biotinylated), others are not. The present invention relates to any of the primers mentioned, primers containing unmodified nucleotides, or primers containing modified nucleotides.

Different techniques can be applied to perform the sequence-specific hybridization methods of the present invention. These techniques may comprise immobilizing the amplified HIV polynucleic acids on a solid support and performing hybridization with labeled oligonucleotide probes. HIV polynucleic acids may also be immobilized on a solid support without prior amplification and subjected to hybridization. Alternatively, the probes may be immobilized on a solid support and hybridization may be performed with labeled HIV polynucleic acids, preferably after amplification. This technique is called reverse hybridization. A convenient reverse hybridization technique is the line probe assay (LiPA). This assay uses oligonucleotide probes immobilized as parallel lines on a solid support strip (Stuyver et al., 1993). It is to be understood that any other technique based on the above-mentioned methods is also covered by the present invention.

According to another preferred embodiment, the present invention relates to any of the probes mentioned above and/or to any of the primers mentioned above, with said primers and probes being designed for use in a method for determining the susceptibility to antiviral drugs of HIV viruses in a sample. According to an even more preferred embodiment, the present invention relates to the probes with seq id no 7 to seq id no 477 and seq id no510 to seq id no 519, more preferably to the seq id no mentioned in Table 1 and Table 7, and to the primers with seq id no 3, 4, 5 and 6, 501, 502, 503, 504, 505, 506, 507, 508 and 509. The skilled man will recognize that addition or deletion of one or more nucleotides at their extremities may adapt the said probes and primers. Such adaptations may be requited if the conditions of amplification or hybridization are changed, or if the amplified material is RNA instead of DNA, as is the case in the NASBA system According to another preferred embodiment, the present invention relates to a diagnostic kit enabling a method for determining the susceptibility to antiviral drugs of HIV viruses in a biological sample, with said kit comprising:

a) when appropriate, a means for releasing, isolating or concentrating the polynucleic acids present in said sample;

b) when appropriate, at least one of the primers of any of claims 4 to 6;

c) at least one of the probes of any of claims 1 to 3, possibly fixed to a solid support;

d) a hybridization buffer, or components necessary for producing said buffer;

e) a wash solution, or components necessary for producing said solution;

f) when appropriate, a means for detecting the hybrids resulting from the preceding hybridization;

h) when appropriate, a means for attaching said probe to a solid support.

DEFINITIONS

The following definitions serve to illustrate the terms and expressions used in the present invention.

The term "antiviral drugs" refers particularly to any antiviral protease inhibitor. Examples of such antiviral drugs and the mutation they may cause in the HIV protease gene are disclosed in Schinazi et al., 1997. The contents of the latter two documents particularly are to be considered as forming part of the present invention. The most important antiviral drugs focussed at in the present invention are disclosed in Tables 1 to 2.

The target material in the samples to be analyzed may either be DNA or RNA, e.g.: genomic DNA, messenger RNA, viral RNA or amplified versions thereof. These molecules are also termed polynucleic acids.

It is possible to use genomic DNA or RNA molecules from HIV samples in the methods according to the present invention.

Well-known extraction and purification procedures are available for the isolation of RNA or DNA from a sample (fi. in Maniatis et al., Molecular Cloning: A Laboratory Manual, 2nd Edition, Cold Spring Harbour Laboratory Press (1989)).

The term "probe" refers to single stranded sequence-specific oligonucleotides, which have a sequence, which is complementary to the target sequence to be detected.

The term "target sequence" as referred to in the present invention describes the wild type nucleotide sequence, or the sequence comprising one or more polymorphic nucleotides of the protease gene to be specifically detected by a probe according to the present invention. This nucleotide sequence may encompass one or several nucleotide changes. Target sequences may refer to single nucleotide positions, codon positions, nucleotides encoding amino acids or to sequences spanning any of the foregoing nucleotide positions. In the present invention said target sequence often includes one or two variable nucleotide positions.

The term "polymorphic nucleotide" indicates a nucleotide in the protease gene of a particular HIV virus that is different from the nucleotide at the corresponding position in at least one other HIV virus. The polymorphic nucleotide may or may not give rise to resistance to an antiviral drug. It is to be understood that the complement of said target sequence is also a suitable target sequence in some cases. The target sequences as defined in the present invention provide sequences which should be complementary to the central part of the probe which is designed to hybridize specifically to said target region.

The term "complementary" as used herein means that the sequence of the single stranded probe is exactly the (inverse) complement of the sequence of the single-stranded target, with the target being defined as the sequence where the mutation to be detected is located.

"Specific hybridization" of a probe to a target sequence of the HIV polynucleic acids means that said probe forms a duplex with part of this region or with the entire region under the experimental conditions used, and that under those conditions said probe does not form a duplex with other regions of the polynucleic acids present in the sample to be analyzed.

Since the current application requires the detection of single basepair mismatches, very stringent conditions for hybridization are required, allowing in principle only hybridization of exactly complementary sequences. However, variations arm possible in the length of the probes (see below), and it should be noted that, since the central part of the probe is essential for its hybridization characteristics, possible deviations of the probe sequence versus the target sequence may be allowable towards head and tail of the probe, when longer probe sequences are used. These variations, which may be conceived from the common knowledge in the art, should however always be evaluated experimentally, in order to check if they result in equivalent hybridization characteristics than the exactly complementary probes.

Preferably, the probes of the invention are about 5 to 50 nucleotides long, more preferably from about 10 to 25 nucleotides. Particularly preferred lengths of probes include 10, 11, 12, 13, 14, 15, 16, 17, 18, 19, 20, 21, 22, 23, 24 or 25 nucleotides. The nucleotides as used in the present invention may be ribonucleotides, deoxyribonucleotides and modified nucleotides such as inosine or nucleotides containing modified groups, which do not essentially alter their hybridization characteristics.

Probe sequences are represented throughout the specification as single stranded DNA oligonucleotides from the 5' to the 3' end. It is obvious to the man skilled in the art that any of the below-specified probes can be used as such, or in their complementary form, or in their RNA form (wherein U replaces T).

The probes according to the invention can be prepared by cloning of recombinant plasmids containing inserts including the corresponding nucleotide sequences, if need be by cleaving the latter out from the cloned plasmids upon using the adequate nucleases and recovering them, e.g. by fractionation according to molecular weight. The probes according to the present invention can also be synthesized chemically, for instance by the conventional phosphotriester method.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead) or a chip. Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin, haptens or proteins.

The term "labeled" refers to the use of labeled nucleic acids. Labeling may be carried out by the use of labeled nucleotides incorporated during the polymerase step of the amplification such as illustrated by Saiki et al. (1988) or Bej et al. (1990) or labeled primers, or by any other method known to the person skilled in the art. The nature of the label may be isotopic ($^{32}P$, $^{35}S$, etc.) or non-isotopic (biotin, digoxigenin, etc.).

The term "primer" refers to a single stranded oligonucleotide sequence capable of acting as a point of initiation for synthesis of a primer extension product, which is complementary to the nucleic acid strand to be copied. The length and the sequence of the primer must be such that they allow to prime the synthesis of the extension products. Preferably the primer is about 5–50 nucleotides long. Specific length and sequence will depend on the complexity of the required DNA or RNA targets, as well as on the conditions of primer use such as temperature and ionic strength.

The term "primer pair" refers to a set of primers comprising at least one 5' primer and one 3' primer. The primer pair may consist of more than two primers, the complexity of the number of primers will depend on the hybridization conditions, variability of the sequences in the regions to be amplified and the target sequences to be detected.

The fact that amplification primers do not have to match exactly with the corresponding template sequence to warrant proper amplification is amply documented in the literature (Kwok et al., 1990).

The amplification method used can be either polymerase chain reaction (PCR; Saiki et al., 1988), ligase chain reaction (LCR; Landgren et al., 1988; Wu & Wallace, 1989; Barany, 1991), nucleic acid sequence-based amplification (NASBA; Guatelli et al., 1990; Compton, 1991), transcription-based amplification system (TAS; Kwoh et al., 1989), strand displacement amplification (SDA; Duck, 1990) or amplification by means of QB replicase (Lomeli et al., 1989) or any other suitable method to amplify nucleic acid molecules known in the art.

The oligonucleotides used as primers or probes may also comprise nucleotide analogues such as phosphorothiates (Matsukura et al., 1987), alkylphosphorothiates (Miller et al., 1979) or peptide nucleic acids (Nielsen et al., 1991; Nielsen et al., 1993) or may contain intercalating agents (Asseline et al., 1984).

As most other variations or modifications introduced into the original DNA sequences of the invention these variations will necessitate adaptations with respect to the conditions under which the oligonucleotide should be used to obtain the required specificity and sensitivity. However the eventual results of hybridization will be essentially the same as those obtained with the unmodified oligonucleotides.

The introduction of these modifications may be advantageous in order to positively influence characteristics such as hybridization kinetics, reversibility of the hybrid-formation, biological stability of the oligonucleotide molecules, etc.

The "sample" may be any biological material taken either directly from the infected human being (or animal), or after culturing (enrichment). Biological material may be e.g. expectorations of any kind, broncheolavages, blood, skin tissue, biopsies, sperm, lymphocyte blood culture material, colonies, liquid cultures, fecal samples, urine etc.

The sets of probes of the present invention will include at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more probes. Said probes may be applied in two or more distinct and known positions an a solid substrate. Often it is preferable to apply two or more probes together in one and the same position of said solid support.

For designing probes with desired characteristics, the following useful guidelines known to the person skilled in the art can be applied.

Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

The stability of the [probe:target] nucleic acid hybrid should be chosen to be compatible with the assay conditions. This may be accomplished by avoiding long AT-rich sequences, by terminating the hybrids with G:C base pairs, and by designing the probe with an appropriate Tm. The beginning and end points of the probe should be chosen so that the length and % GC result in a Tm about 2–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account when designing a probe. It is known that hybridization will increase as the ionic strength of the reaction mixture increases, and that the thermal stability of the hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at tempts below the optimum may allow mismatched base sequences to hybridize and can therefore result in reduced specificity.

It is desirable to have probes, which hybridize only under conditions of high stringency. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. The degree of stringency is chosen such as to maximize the difference in stability between the hybrid formed with the target and the nontarget nucleic acid. In the present case, single base pair changes need to be detected, which requires conditions of very high stringency.

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another that differs merely by a single base. While it is possible for nucleic acids that are not perfectly complementary to hybridize, the longest stretch of perfectly complementary base sequence will normally primarily determine hybrid stability. While oligonucleotide probes of different lengths and base composition may be used, preferred oligonucleotide probes of this invention arm between about 5 to 50 (more particularly 10–25) bases in length and have a sufficient stretch in the sequence which is perfectly complementary to the target nucleic acid sequence.

Regions in the target DNA or RNA, which are known to form strong internal structures inhibitory to hybridization, are less preferred. Likewise, probes with extensive self-complementarity should be avoided. As explained above, hybridization is the association of two single strands of complementary nucleic acids to form a hydrogen bonded double strand. It is implicit that if one of the two strands is wholly or partially involved in a hybrid that it will be less able to participate in formation of a new hybrid. There can be intramolecular and intermolecular hybrids formed within the molecules of one type of probe if there is sufficient self complementarity. Such structures can be avoided through careful probe design. By designing a probe so that a substantial portion of the sequence of interest is single stranded, the rate and extent of hybridization may be greatly increased. Computer programs are available to search for this type of interaction. However, in certain instances, it may not be possible to avoid this type of interaction.

Standard hybridization and wash conditions are disclosed in the Materials & Methods section of the Examples. Other conditions are for instance 3×SSC (Sodium Saline Citrate), 20% deionized FA (Formamide) at 50° C.

Other solutions (SSPE (Sodium saline phosphate EDTA), TMACl (tetramethyl ammonium Chloride), etc.) and temperatures can also be used provided that the specificity and sensitivity of the probes is maintained. If need be, slight modifications of the probes in length or in sequence have to be carried out to maintain the specificity and sensitivity required under the given circumstances.

Primers may be labeled with a label of choice (e.g. biotin). Different primer-based target amplification systems may be used, and preferably PCR-amplification, as set out in the examples. Single-round or nested PCR may be used.

The term "hybridization buffer" means a buffer enabling a hybridization reaction to occur between the probes and the polynucleic acids present in the sample, or the amplified product, under the appropriate stringency conditions.

The term "wash solution" means a solution enabling washing of the hybrids formed under the appropriate stringency conditions.

The following examples only serve to illustrate the present invention. These examples are in no way intended to limit the scope of the present invention.

FIGURE AND TABLE LEGENDS

FIG. 1: Natural and drug selected variability in the vicinity of codons 30, 46, 48, 50, 54, 82, 84, and 90 of the HIV-1 protease gene. The most frequently observed wild-type sequence is shown in the top line (SEQ ID NO: 520 for codon 30, SEQ ID NO: 521 for codon 46/48, SEQ ID NO: 522 for codon 50, SEQ ID NO: 523 for codon for codon 54, SEQ ID NO: 524 for codon 82/84, and SEQ ID NO: 525 for codon 90). Naturally occurring variations are indicated below and occur independently from each other. Variants sequences for each of the indicated codons are as follows: SEQ ID NO: 7–46 for codon 30, SEQ ID NO: 47–120 for codon 46/48, SEQ ID NO: 121–175 for codon 50, SEQ ID NO: 176–227 for codon 54, SEQ ID NO: 228–357 for codon 82/84, and SEQ ID NO: 358–477 for codon 90. Drug-selected variants are indicated in bold.

FIG. 2A: Reactivities of the selected probes for codon 30 immobilized on LiPA strips with reference material. The information in the boxed surface is not relevant for the discussion of probes for codon 30. The position of each selected probe on the membrane strip is shown at the left of each panel. The sequence of the relevant part of the selected probes is shown at the left and is given in Table 1. Each strip is incubated with a biotinylated PCR fragment from the reference panel. The reference panel accession numbers are indicated in Table 1 (SEQ ID NO: 31 corresponds to w25, SEQ ID NO: 35 corresponds to w29, SEQ ID NO: 32 corresponds to w32, SEQ ID NO: 42 corresponds to w36, and SEQ ID NO: 29 corresponds to m23). For several probes multiple reference panel possibilities are available, but only one relevant accession number given each time. *: False positive reactivities. At the bottom the strips, the amino acids at the relevant codon, as derived from the probe reactivity, is indicated.

Figure 2B:
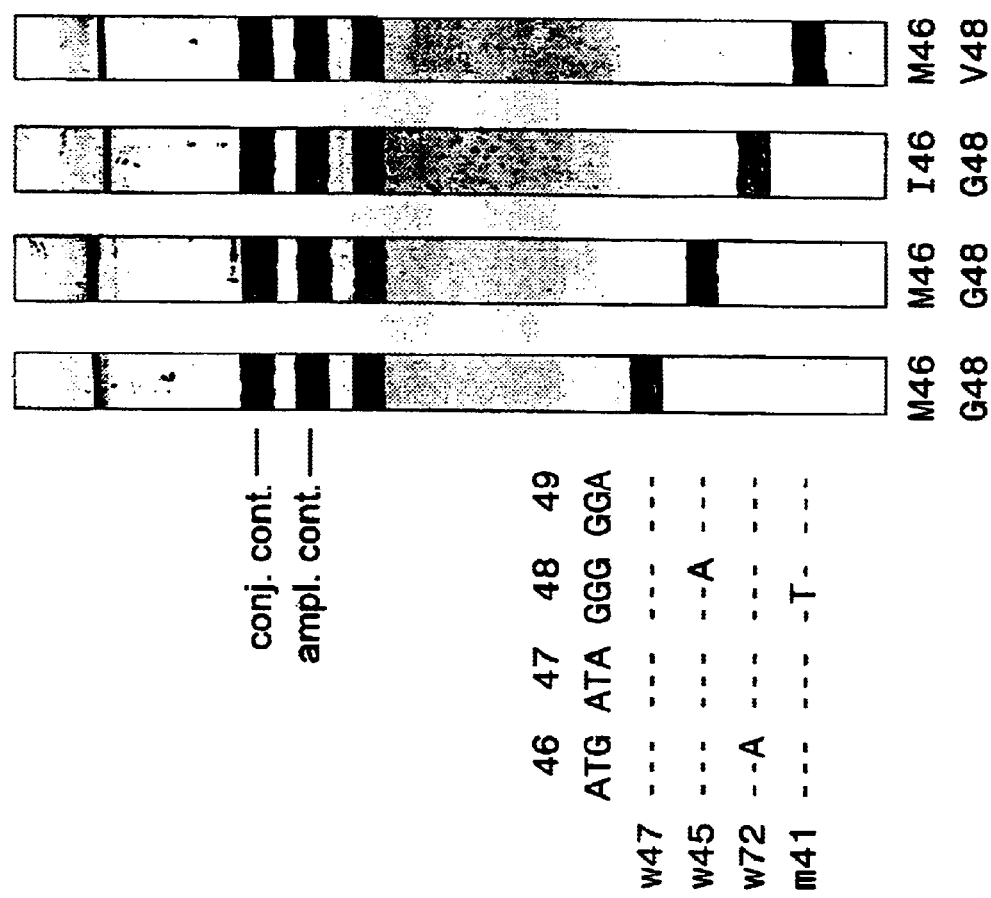

FIG. 2B: Reactivities of the selected probes for codons 46 and 48 immobilized on LiPA strips with reference material. The information in the boxed surface is not relevant for the discussion of probes for codons 46 and 48. The position of each selected probe on the membrane strip is shown at the left of each panel. The sequence of the relevant part of the selected probes is given in Table 1. Each strip is incubated with a biotinylated PCR fragment from the reference panel. The reference panel accession numbers are indicated in Table 1 (SEQ ID NO: 93 corresponds to w47, SEQ ID NO: 91 corresponds to w45, SEQ ID NO: 120 corresponds to w72, and SEQ ID NO: 87 corresponds to m41). For several probes multiple reference panel possibilities are available, but only one relevant accession number given each time. *: False positive reactivities. On top of the strips, the amino acids at the relevant codon, as derived from the probe reactivity, is indicated.

Figure 2C:
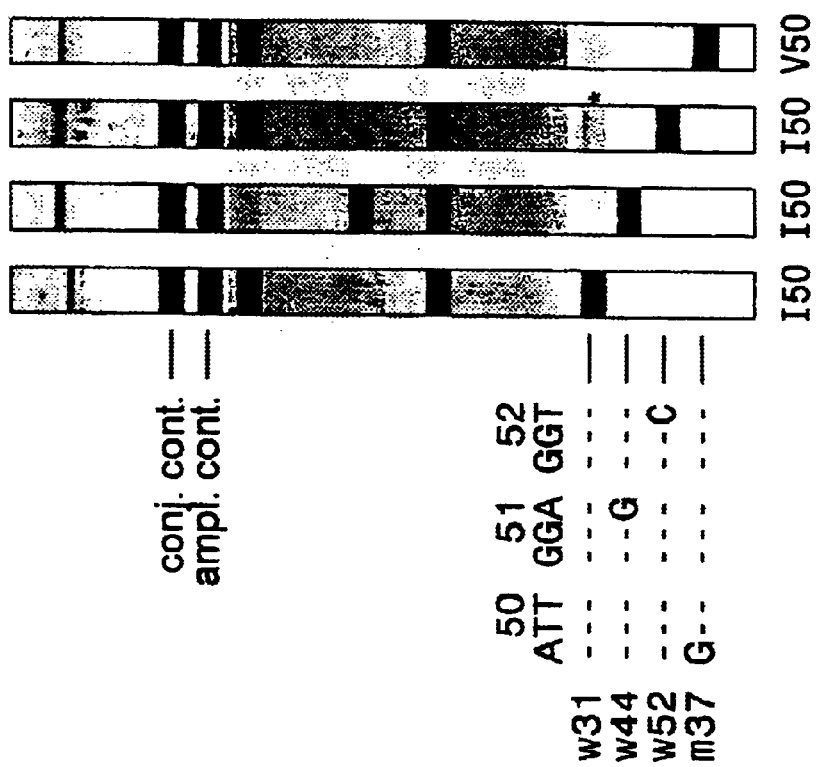

FIG. 2C: Reactivities of the selected probes for codon 50 immobilized on LiPA strips With reference material. The information in the boxed surface is not relevant for the discussion of probes for codon 50. The position of each selected probe on the membrane strip is shown at the left of each panel. The sequence of the relevant part of the selected probes is given in Table 1. Each strip is incubated with a biotinylated PCR fragment from the reference panel. The reference panel accession numbers are indicated in Table 1 (SEQ ID NO: 151 corresponds to w31, SEQ ID NO: 164 corresponds to w44, SEQ ID NO: 172 corresponds to w51, and SEQ ID NO: 157 corresponds to m37). For several probes multiple reference panel possibilities are available, but only one relevant accession number given each time. *: False positive reactivities. At the bottom of the strips, the amino acids at the relevant codon, as derived from the probe reactivity, is indicated.

Figure 2D:
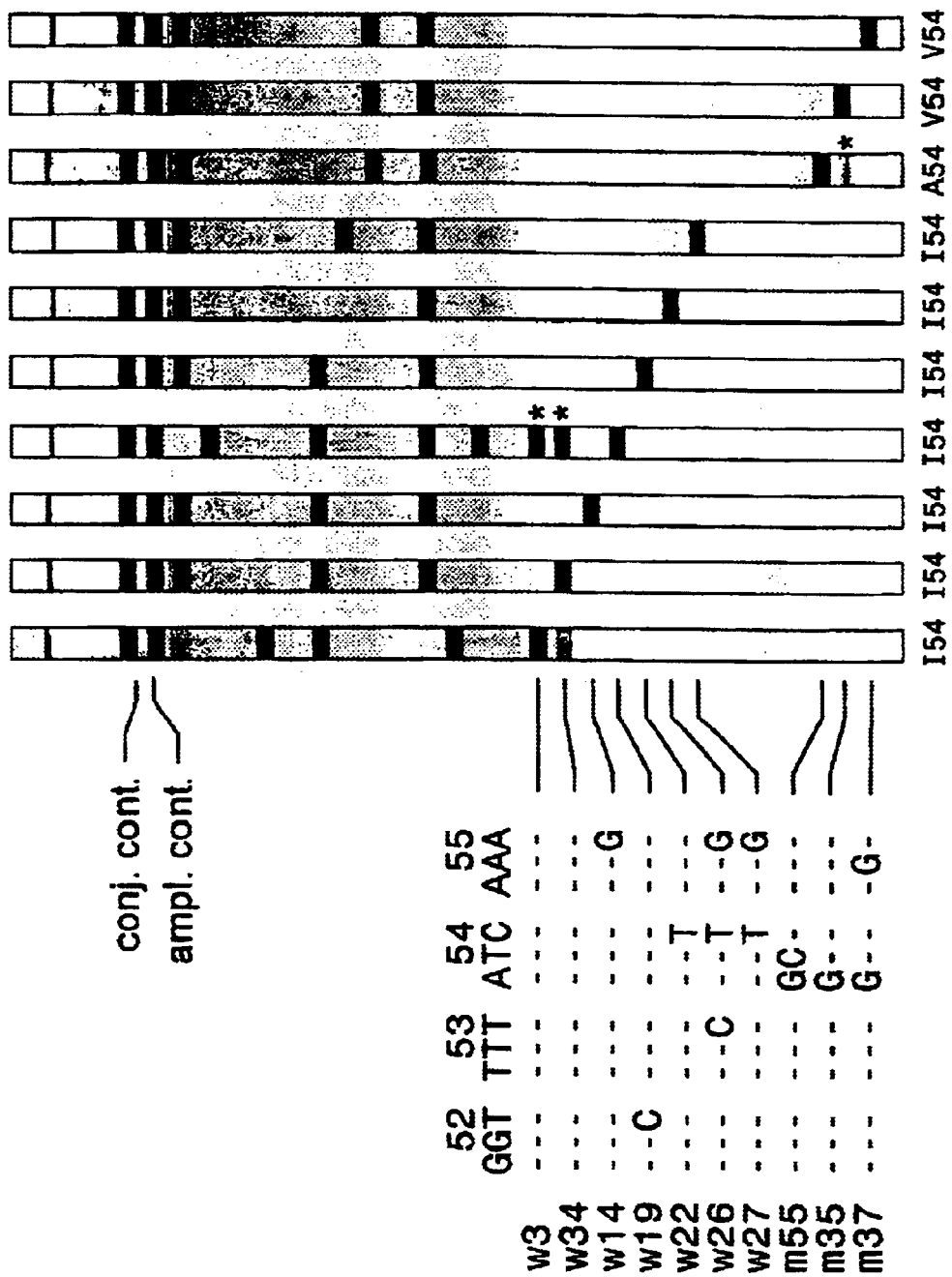

FIG. 2D: Reactivities of the selected probes for codon 54 immobilized on LiPA strips with reference material. The information in the boxed surface is not relevant for the discussion of probes for codon 54. The position of each selected probe on the membrane strip is shown at the left of each panel. The sequence of the relevant part of the selected probes is given in Table 1. Each strip is incubated with a biotinylated PCR fragment from the reference panel. The reference panel accession numbers are indicated in Table 1

(SEQ ID NO: 178 corresponds to w3, SEQ ID NO: 212 corresponds to w34, SEQ ID NO: 189 corresponds to w14, SEQ ID NO: 194 corresponds to w19, SEQ ID NO: 197 corresponds to w22, SEQ ID NO: 202 corresponds to w26, SEQ ID NO: 204 corresponds to w27, SEQ ID NO: 213 corresponds to m35, and SEQ ID NO: 215 corresponds to m37). For several probes multiple reference panel possibilities are available, but only one relevant accession number given each time. *: False positive reactivities. At the bottom of the strips, the amino acids at the relevant codon, as derived from the probe reactivity, is indicated.

Figure 2E:
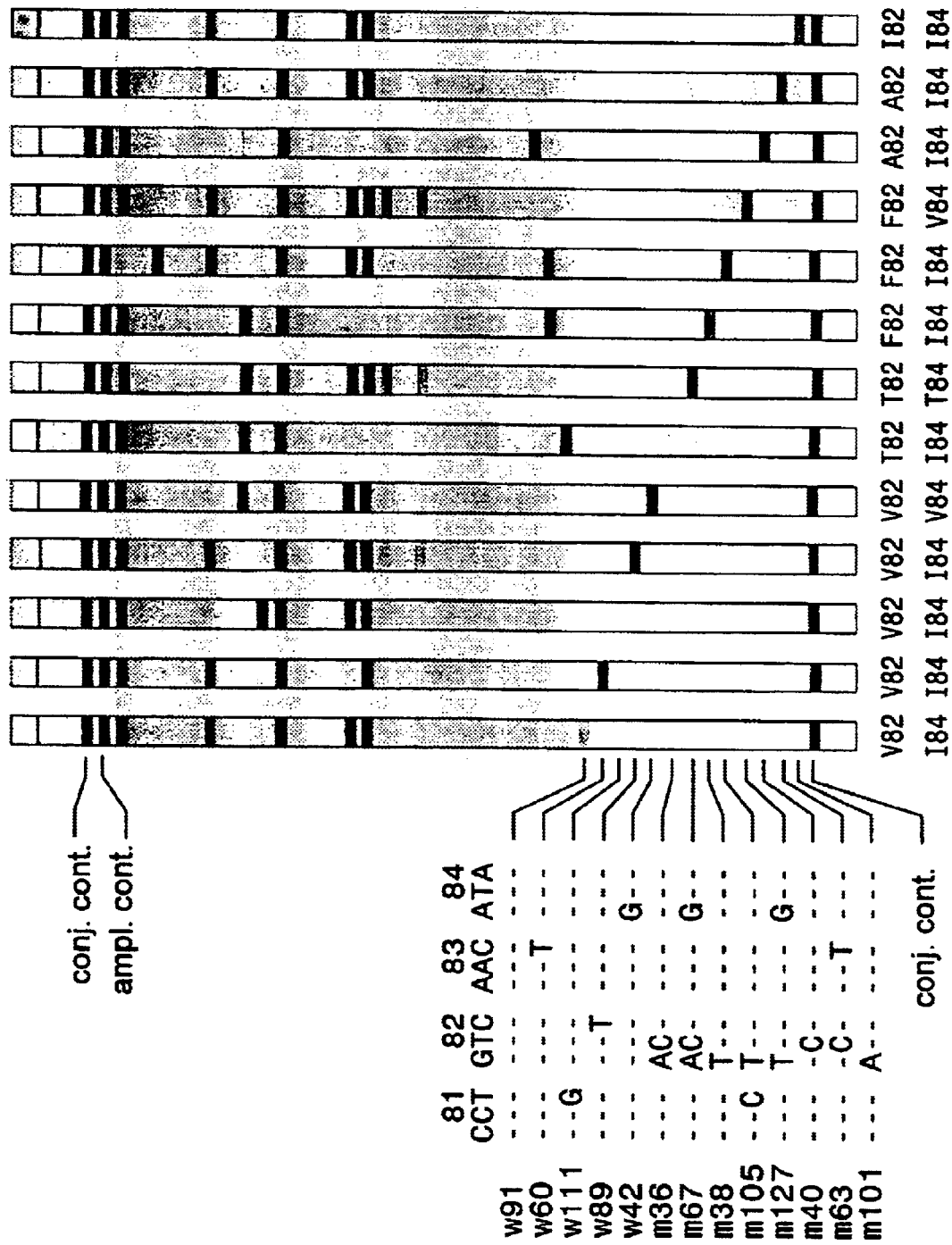

FIG. 2E: Reactivities of the selected probes for codons 82 and 84 immobilized on LiPA strips with reference material. The information in the boxed surface is not relevant for the discussion of probes for codons 82 and 84. The position of each selected probe on the membrane strip is shown at the left of each panel. The sequence of the relevant part of the selected probes is given in Table 1. Each strip is incubated with a biotinylated PCR fragment from the reference panel. The reference panel accession numbers are indicated in Table 1 (SEQ ID NO: 318 corresponds to w91, SEQ ID NO: 287 corresponds to w60, SEQ ID NO: 338 corresponds to w111, SEQ ID NO: 316 corresponds to w89, SEQ ID NO: 269 corresponds to w42 SEQ ID NO: 263 corresponds to m36, SEQ ID NO: 294 corresponds to m67. SEQ ID NO: 265 corresponds to m38, SEQ ID NO: 332 corresponds to m105, SEQ ID NO: 354 corresponds to m127, SEQ ID NO: 267 corresponds to m40, SEQ ID NO: 290 corresponds to m63, and SEQ ID NO: 328 corresponds to m101). For several probes multiple reference panel possibilities are available, but only one relevant accession number given each time. *: False positive reactivities. At the bottom of the strips, the amino acids at the relevant codon, as derived from the probe reactivity, is indicated.

Figure 2F:
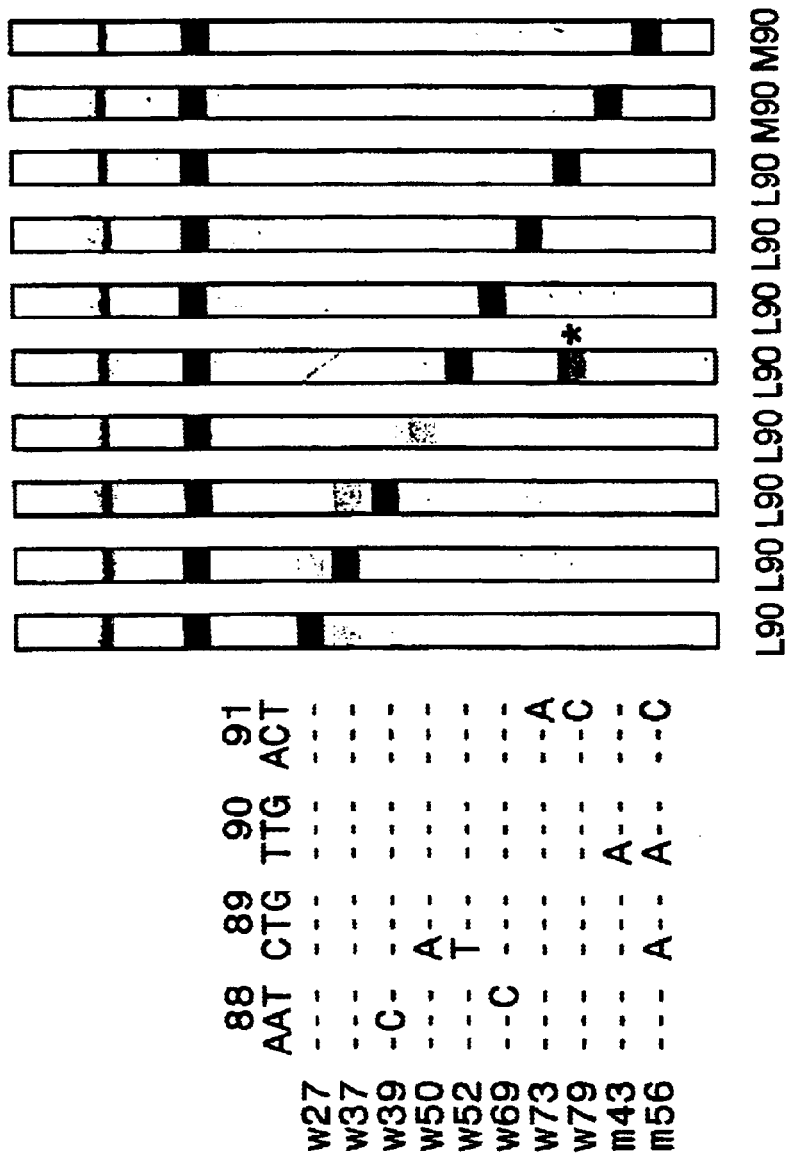

FIG. 2F: Reactivities of the selected probes for codon 90 immobilized on LiPA strips with reference material. The information in the boxed surface is not relevant for the discussion of probes for codon 90. The position of each selected probe on the membrane strip is shown at the left of each panel. The sequence of the relevant part of the selected probes is given in Table 1. Each strip is incubated with a biotinylated PCR fragment from the reference panel. The reference panel accession numbers are indicated in Table 1 (SEQ ID NO: 384 corresponds to w27, SEQ ID NO: 394 corresponds to w37, SEQ ID NO: 396 corresponds to w39, SEQ ID NO: 407 corresponds to w50, SEQ ID NO: 409 corresponds to w52, SEQ ID NO: 426 corresponds to w69, SEQ ID NO: 430 corresponds to w73, SEQ ID NO: 436 corresponds to w79, SEQ ID NO: 400 corresponds to m43, and SEQ ID NO: 413 corresponds to m56). For several probes multiple reference panel possibilities are available, but only one relevant accession number given each time. *: False positive reactivities. At the bottom of the strips, the amino acids at the relevant codon, as derived from the probe reactivity, is indicated.

Figure 3:
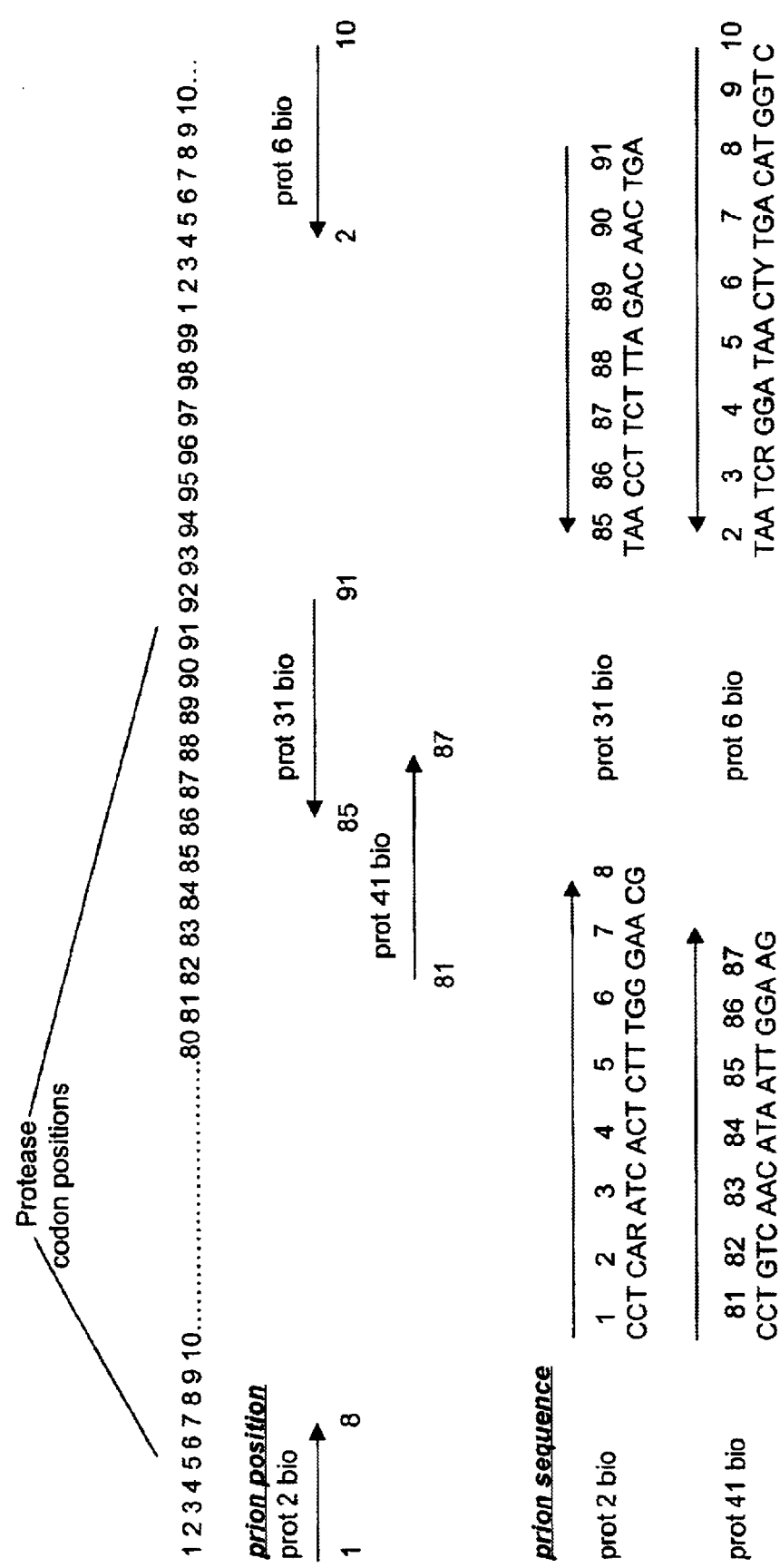

FIG. 3: Sequence and position of the HIV-1 protease amplification primers. To obtain the reactivity with probes selected to determine the susceptibility to antiviral drugs involving codons 30, 46, 48, 50, 54, 82, and 84, nested amplification primers prot2bio (5' primer, SEQ ID NO: 526) and Prot31bio (3' primer, SEQ ID NO: 527) were designed. To obtain the reactivity with probes selected to determine the susceptibility to antiviral drugs involving codon 90, nested amplification primers Prot41bio (5' primer, SEQ ID NO: 528) and Prot6bio (3' primer, SEQ ID NO: 529) were designed.

FIG. 4A: Phylogenetic analysis on 312 protease sequences allowed to separate genotype B strains from non-B strains. Reactivities of the selected probes for codon 30 immobilized on LiPA strips with a biotinylated PCR fragment of genotype B strains and non-B strains is shown, the exact percentages are indicated in table 5. The probes are indicated at the bottom. The sequence of the relevant part of the probes is given in Table 1.

Figure 4B:
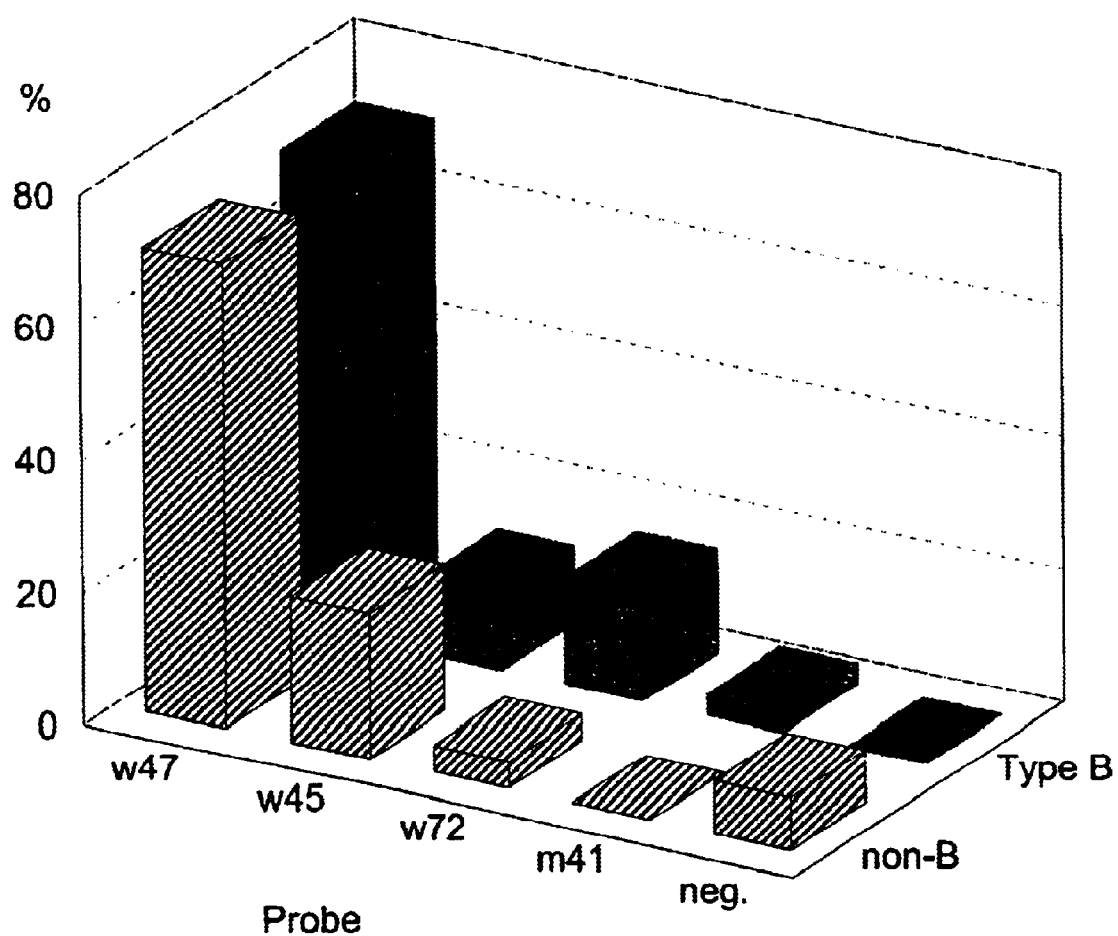

FIG. 4B: Phylogenetic analysis on 312 protease sequences allowed to separate genotype B strains from non-B strains. Reactivities of the selected probes for codons 46/48 immobilized on LiPA strips with a biotinylated PCR fragment of genotype B strains and non-B strains is shown, the exact percentages are indicated in table 5. The probes are indicated at the bottom. The sequence of the relevant part of the probes is given in Table 1.

Figure 4C:
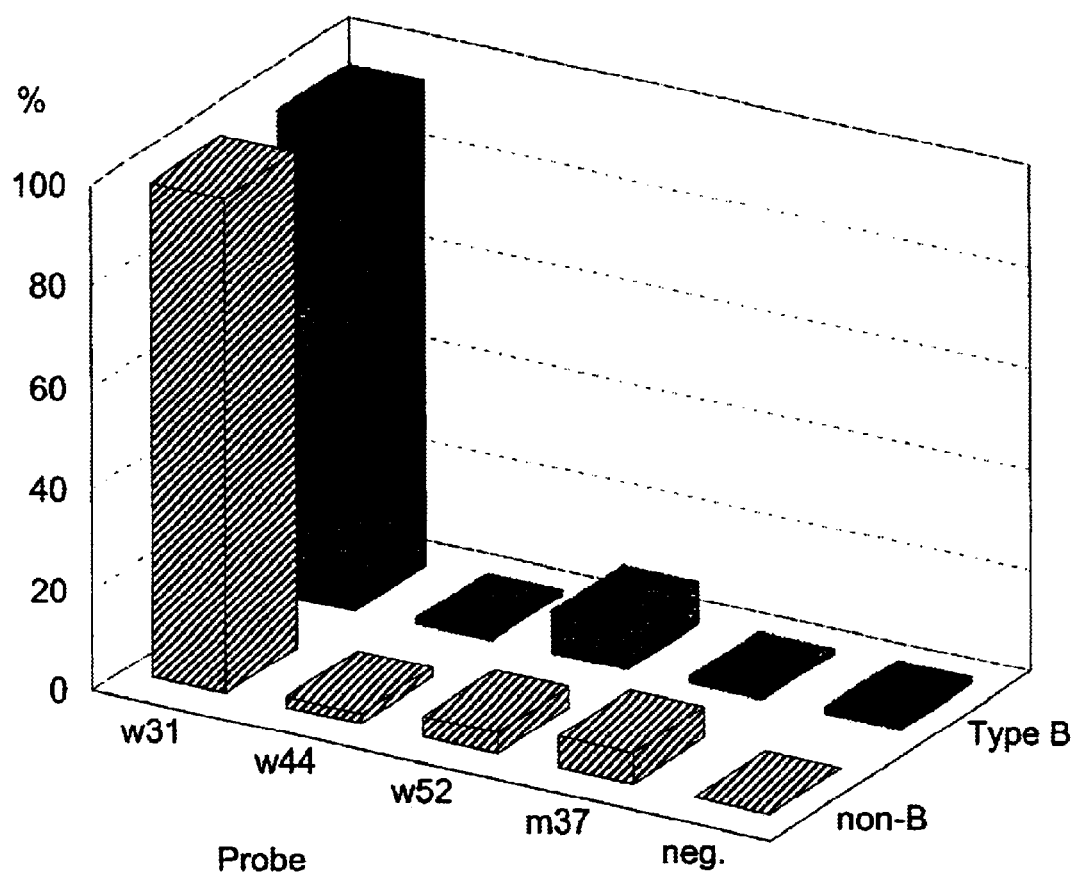

FIG. 4C: Phylogenetic analysis on 312 protease sequences allowed to separate genotype B strains from non-B strains. Reactivities of the selected probes for codon 50 immobilized on LiPA strips with a biotinylated PCR fragment of genotype B strains and non-B sons is shown, the exact percentages are indicated in table 5. The probes are indicated at the bottom. The sequence of the relevant part of the probes is given in Table 1.

Figure 4D:
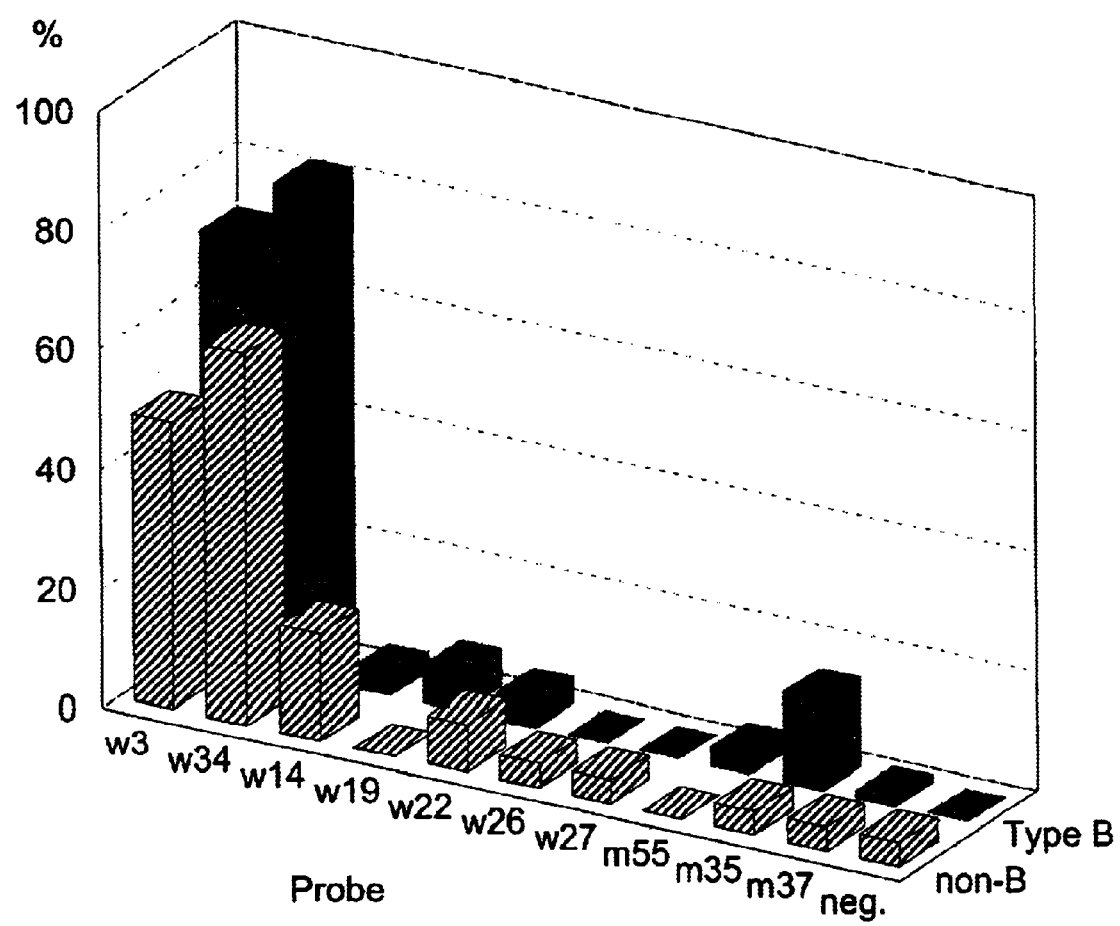

FIG. 4D: Phylogenetic analysis on 312 protease sequences allowed to separate genotype B strains from non-B strains. Reactivities of the selected probes for codon 54 immobilized on LiPA strips with a biotinylated PCR fragment of genotype B strains and non-B stains is shown, the exact percentages are indicated in table 5. The probes are indicated at the bottom. The sequence of the relevant part of the probes is given in Table 1.

Figure 4E:
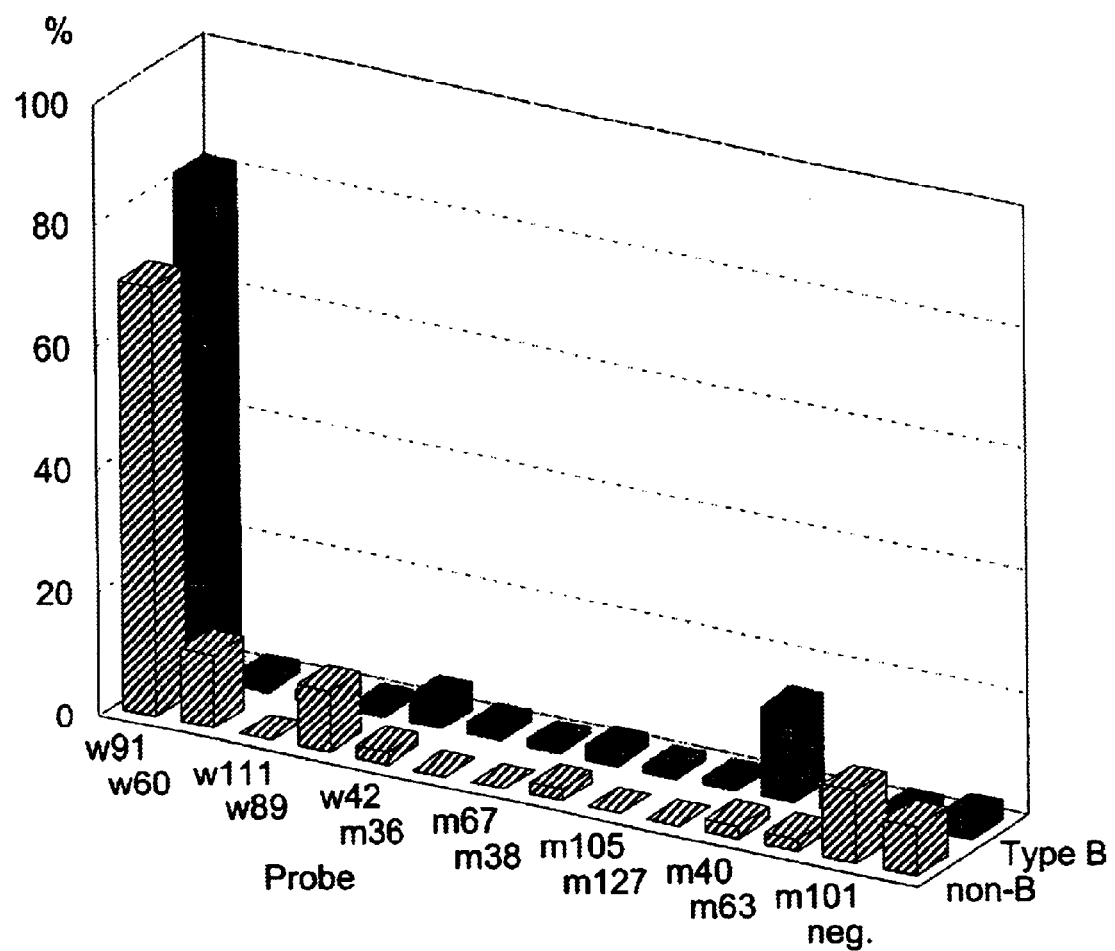

FIG. 4E: Phylogenetic analysis on 312 protease sequences allowed to separate genotype B strains from non-B strains. Reactivities of the selected probes for codons 82/84 immobilized an LiPA strips with a biotinylated PCR fragment of genotype B strains and non-B stains is shown, the exact percentages are indicated in table 5. The probes are indicated at the bottom. The sequence of the relevant part of the probes is given in Table 1.

Figure 4F:
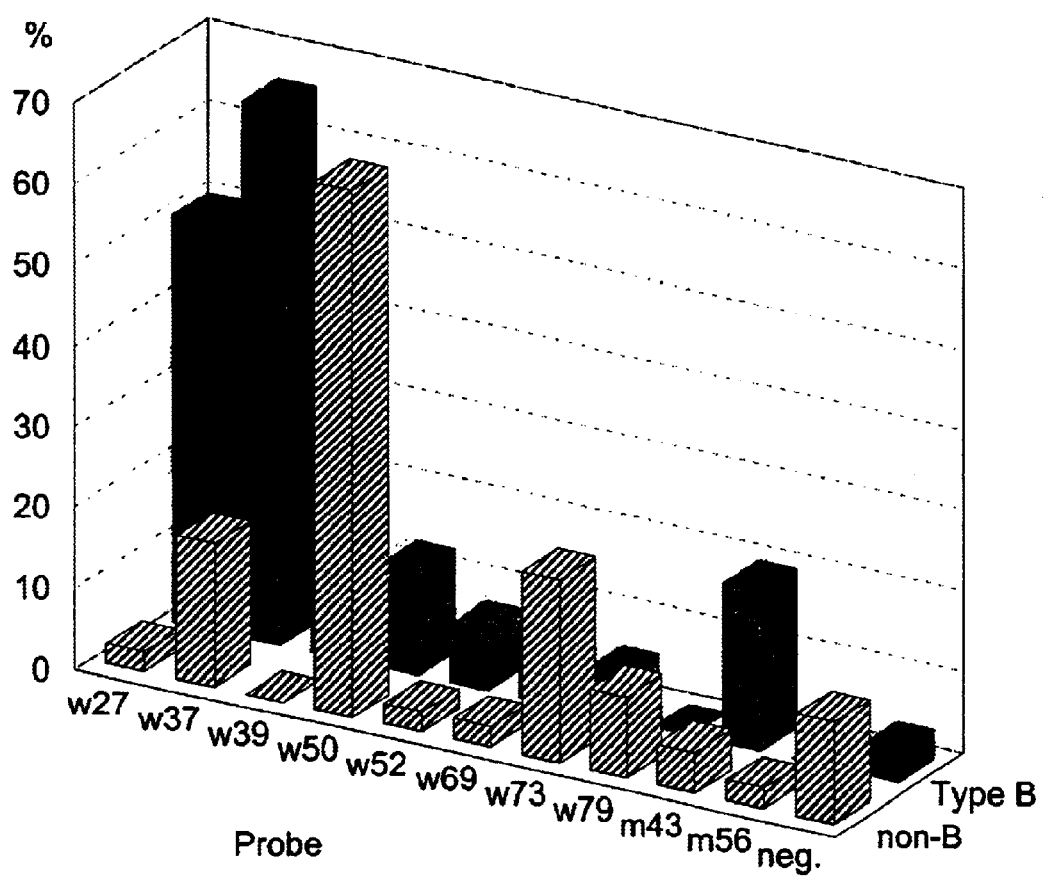

FIG. 4F: Phylogenetic analysis on 312 protease sequences allowed to separate genotype B strains from non-B strains. Reactivities of the selected probes for codon 90 immobilized on LiPA strips with a biotinylated PCR fragment of genotype B strains and non-B strains is shown, the exact percentages are indicated in table 5. The probes are indicated at the bottom. The sequence of the relevant part of the probes is given in Table 1.

Figure 5A:
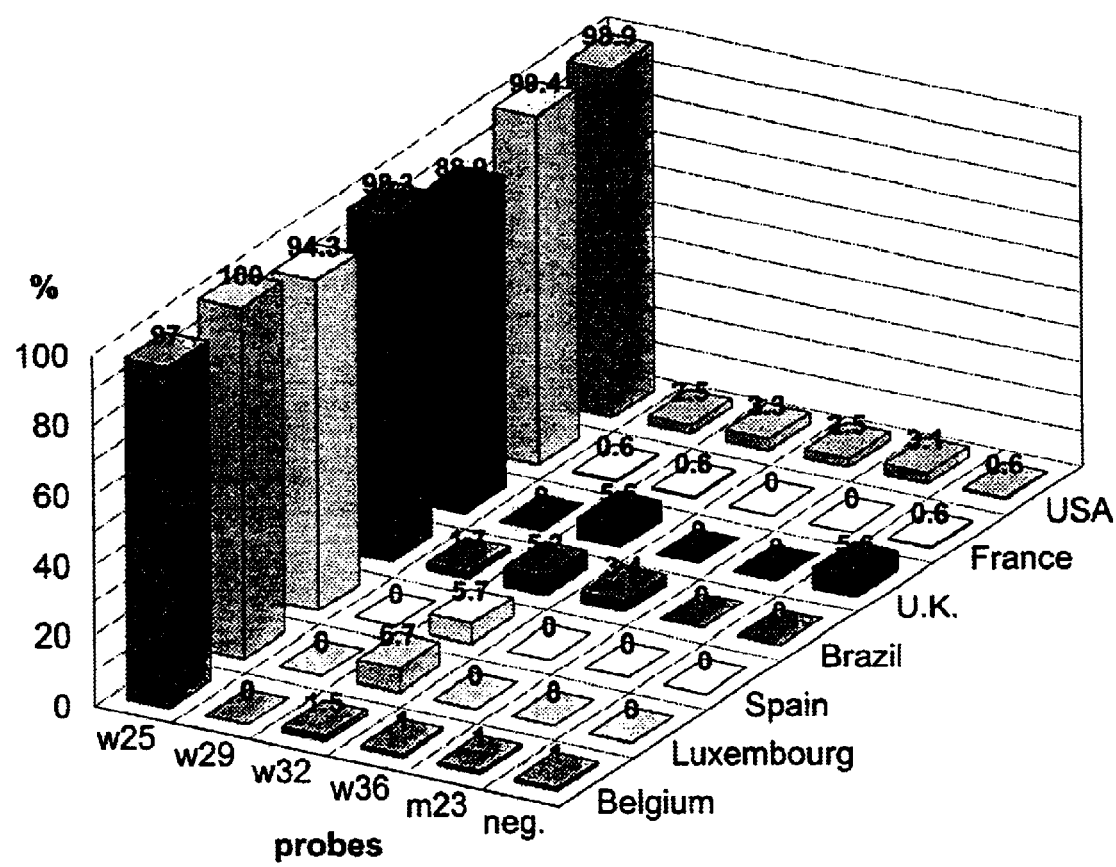

FIG. 5A: Geographical origin of 856 samples and reactivities with the different probes at codon position 30. The exact percentages are indicated in table 6. The probes are indicated at the bottom.

Figure 5B:
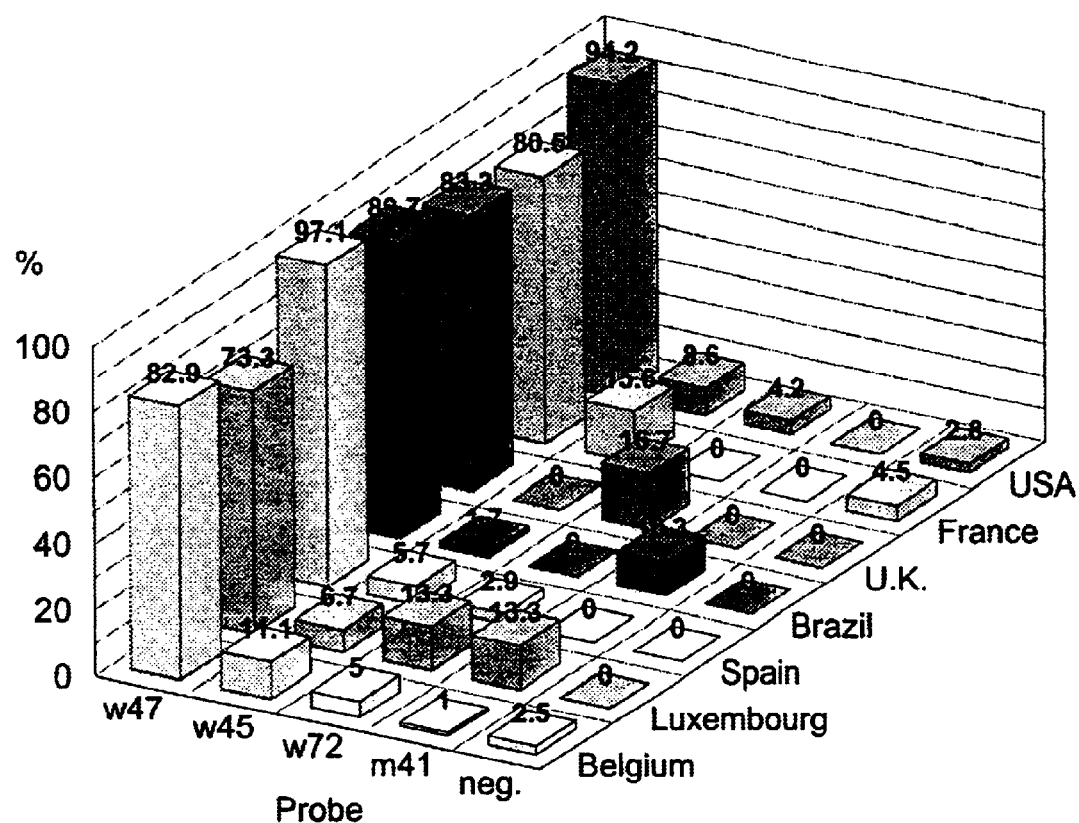

FIG. 5B: Geographical origin of 856 samples and reactivities with the different probes at codon positions 46/48. The exact percentages are indicated in table 6. The probes are indicated at the bottom.

Figure 5C:
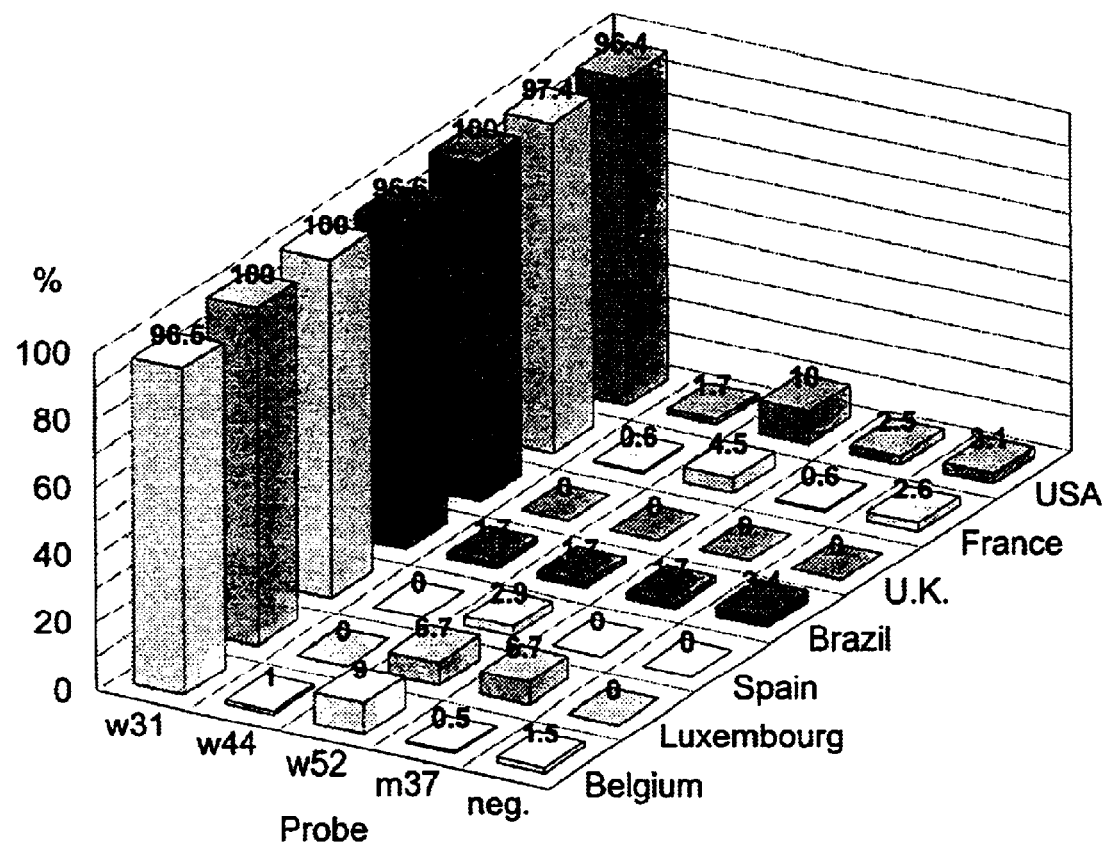

FIG. 5C: Geographical origin of 856 samples and reactivities with the different probes at codon position 50. The exact percentages arm indicated in table 6. The probes are indicated at the bottom.

Figure 5D:
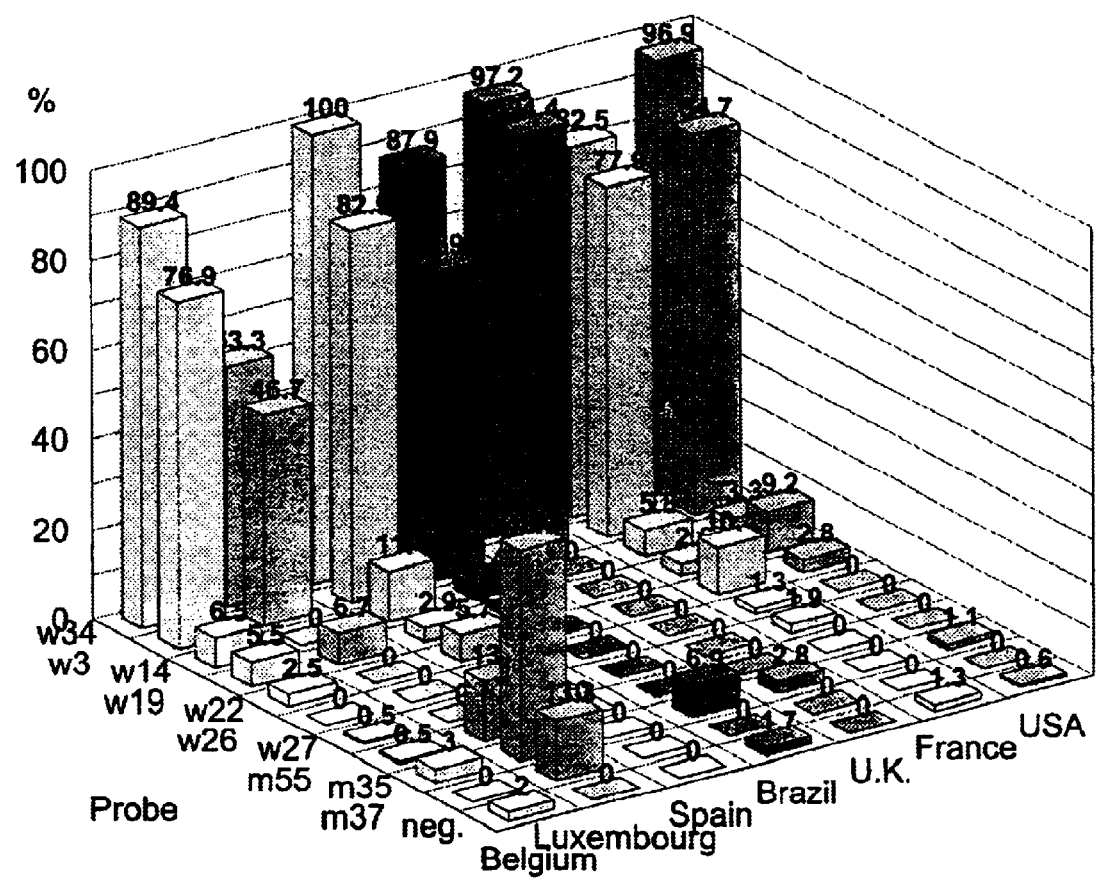

FIG. 5D: Geographical origin of 856 samples and reactivities with the different probes at codon position 54. The exact percentages arm indicated in table 6. The probes are indicated at the bottom.

Figure 5E:
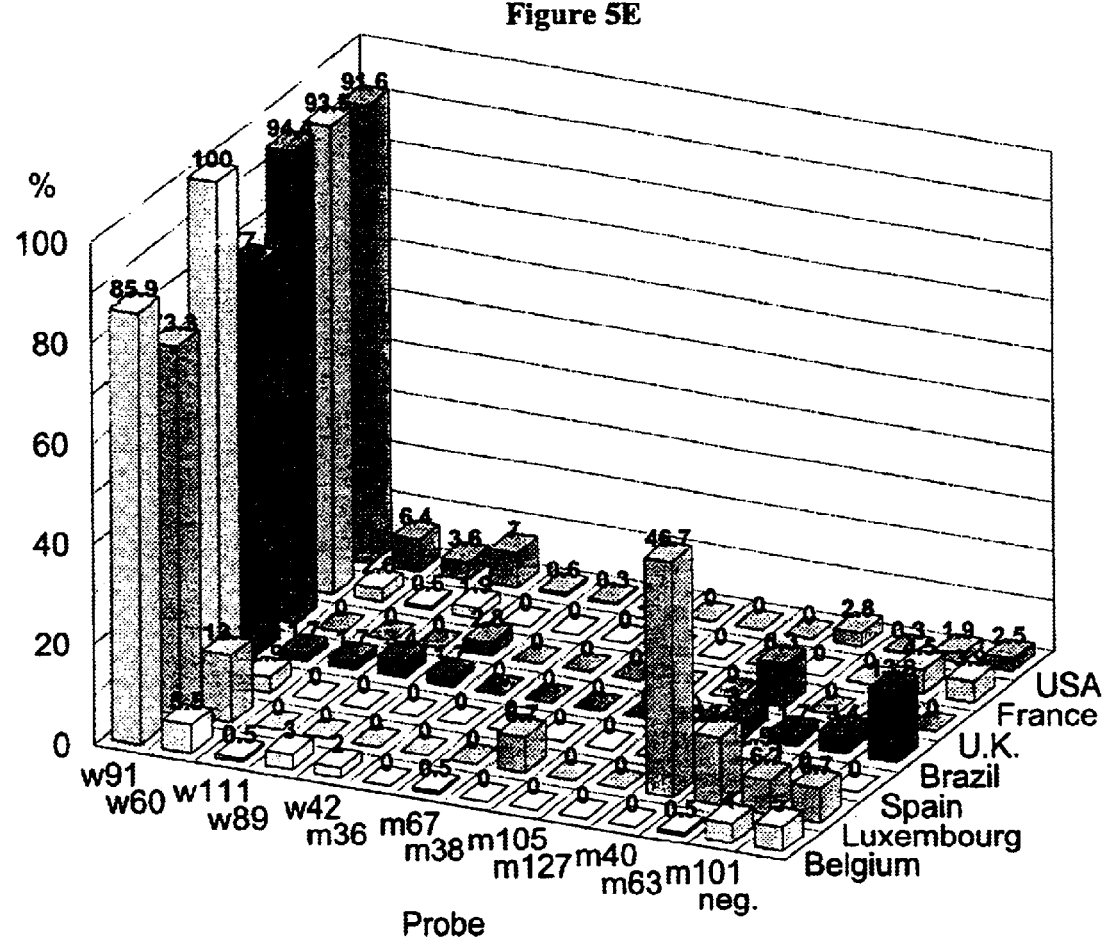

FIG. 5E: Geographical origin of 856 samples and reactivities with the different probes at codon positions 82/84. The exact percentages are indicated in table 6. The probes are indicated at the bottom.

Figure 5F:
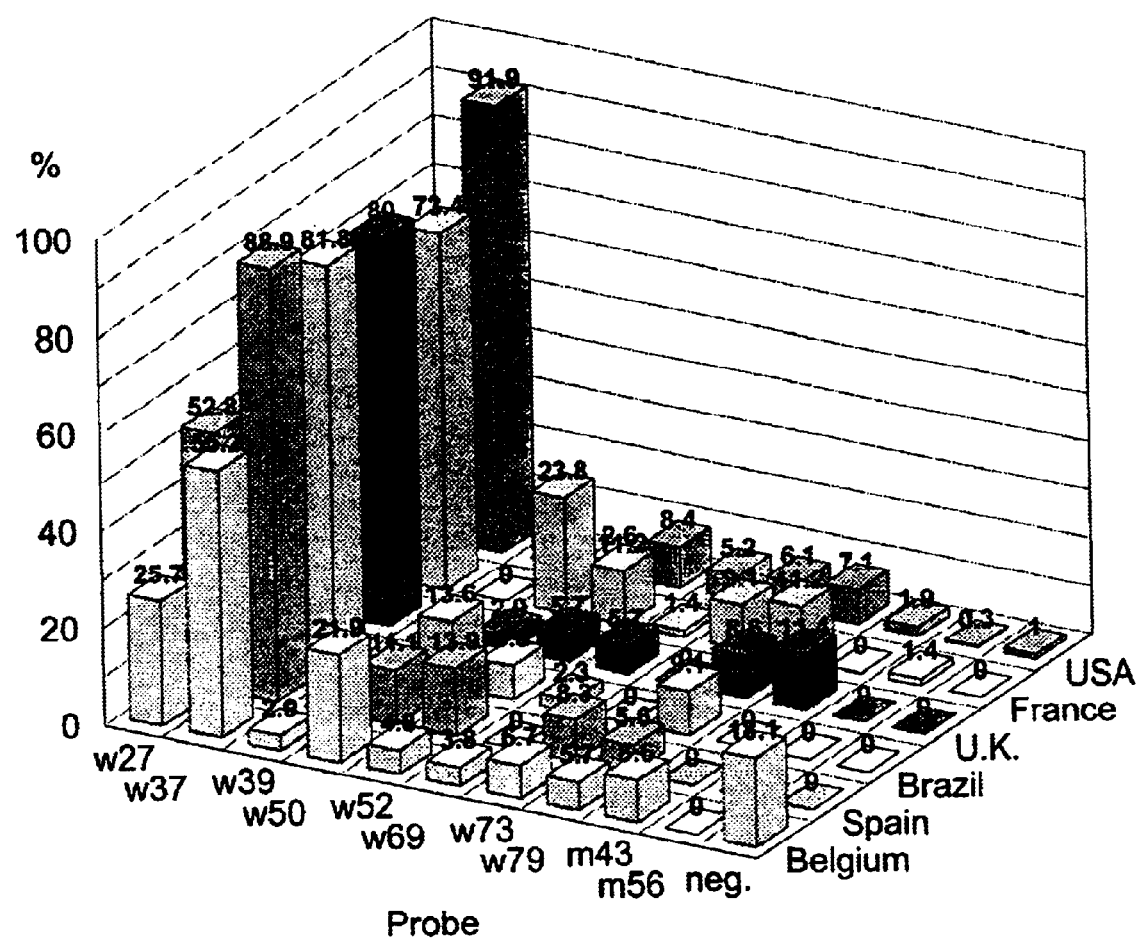

FIG. 5F: Geographical origin of 856 samples and reactivities with the different probes at codon position 90. The exact percentages are indicated in table 6. The probes are indicated at the bottom.

Table 1: HIV-1 protease wild-type and drug-selected mutation probes with their corresponding sequences as applied on the HIV-1 protease LiPA strip. The most frequently observed wild-type sequence is shown at the top line. Probe names corresponding to the selected motifs are indicated in the left column, the relevant part of each probe applied on the strip is shown under the consensus sequence.

Table 2: Protease Inhibitors.

Table 3: HIV-1 protease wild-type and drug-selected mutation probes with their corresponding sequences as synthesized, immobilized and tested on LiPA strips. The most frequently observed wild-type sequence is shown at the top line. Probe names corresponding to the selected motifs arc indicated in the left column, the relevant part of each probe applied on the strip is shown under the consensus sequence. The probes retained are indicated in table 1.

Table 4: Polymorphic nucleotide sequences.

Table 5: % Reactivities of the HIV-1 protease wild-type and drug-selected mutation probes applied on the HIV-1 protease LiPA strip with genotype B strains and non-B strains.

Table 6: % Reactivities of the HIV-1 protease wild-type and drug-selected mutation probes applied on the HIV-1 protease LiPA strip with samples of different geographical origin.

Table 7: HIV-1 protease wild-type and drug-selected mutation probes with their corresponding sequences as applied on the HIV-1 protease LiPA strip. The most frequently observed wild-type sequence is shown at the top line. Probe names corresponding to the selected motifs are indicated in the left column, the relevant part of each probe applied on the strip is shown under the consensus sequence.

EXAMPLES

Example 1

Selection of the Plasma Samples, PCR Amplification and Cloning of the PCR Products Plasma samples (n=557) were taken from HIV type-1 infected patients and stored at −20° C. until use. Plasma samples were obtained from naive and drug-treated patients. The drugs involved ritonavr, indinavir and saquinavir. The serum samples were collected from patients residing in Europe (Belgium, Luxembourg, France, Spain and UK), USA and Brazil.

HIV RNA was prepared from these samples using the guanidinium-phenol procedure. Fifty $\mu$l plasma was mixed with 150 $\mu$l Trizol®LS Reagent (Life Technologies, Gent, Belgium) at room temperature (volume ratio: 1 unit sample/3 units Trizol). Lysis and denaturation occurred by carefully pipetting up and down several times, followed by an incubation step at room temperature for at least 5 minutes. Fourthy $\mu$l CHCl$_3$ was added and the mixture was shaken vigorously by hand for at least 15 seconds, and incubated for 15 minutes at room temperature. The samples were centrifuged at maximum 12,000 g for 15 minutes at 4° C., and the colorless aqueous phase was collected and mixed with 100 $\mu$l isopropanol. To visualize the minute amounts of viral RNA, 20 $\mu$l of 1 $\mu$g/$\mu$l Dextran T500 (Pharmacia) was added, mixed and left at room temperature for 10 minutes. Following centrifugation at max. 12,000 g for 10 minutes at 4° C. and aspiration of the supernatant, the RNA pellet was washed with 200 $\mu$l ethanol, mixed by vortexing and collected by centrifugation at 7,500 g for 5 minutes at 4° C. Finally the RNA pellet was briefly air-dried and stored at −20° C. Alternatively, the High Pure Viral Nucleic Acid Kit (Boehringer Mannheim) was used to extract RNA from the samples.

For cDNA synthesis and PCR amplification, the RNA pellet was dissolved in 15 $\mu$l random primes (20 ng/$\mu$l, pdN$_6$, Pharmacia), prepared in DEPC-treated or HPLC grade water. After denaturation at 70° C. for 10 minutes, 5 $\mu$l cDNA mix was added, composed of 4 $\mu$l 5× AMV-RT buffer (250 mM Tris.HCl pH 8.5, 100 mM KCl, 30 mM MgCl$_2$, 25 mM DTT)), 0.4 $\mu$L 25 mM dXTPs, 0.2 $\mu$l or 25 U Ribonuclease Inhibitor (HPRI, Amersham), and 0.3 $\mu$l or 8 U AMV-RT (Stratagene). cDNA synthesis occurred during the 90 minutes incubation at 42° C. The HIV-1 protease gene was than amplified using the following reaction mixture: 5 $\mu$l cDNA, 4.5 $\mu$l 10× Taq buffer, 0.3 $\mu$l 25 mM dXTPs, 1 $\mu$l (10 pmol) of each PCR primer, 38 $\mu$l H$_2$O, and 0.2 $\mu$l (1 U) Taq. . Alternatively, the Titon One Tube RT-PCR system (Boehringer Mannheim) was used to perform RT-PCR. Codon positions involving resistance to saquinavir, ritonavir, indinavir, nelfinavir and VX-478 have been described (Shinazi et al) and PCR amplification primers were chosen outside these regions. The primer design was based on HIV-1 published sequences (mainly genotype B clade) (Myers et al.) and located in regions that showed a high degree of nucleotide conservation between the different HIV-1 clades. The final amplified region covered the HIV-1 protease gene from codon 9 to codon 99. The primers for amplification had the following sequence: outer sense primer Pr16: 5' bio-CAGAGCCAACAGCCCCACCAG 3' (SEQ ID NO 1); nested sense primer Prot2bio: 5' CCT CAR ATC ACT CTT TGG CAA CG 3' (SEQ ED NO 3); nested antisense primer Prot6bio: 3' TAA TCR GGA TAA CTY TGA CAT GGT C 5' (SEQ ID NO 4); and outer antisense primer RT12: 5' bioATCAGGATGGAGTTCATAAC-CCATCCA 3' (SEQ ID NO 2). Annealing occurred at 57° C., extension at 72° C. and denaturation at 94° C. Each step of the cycle took 1 minute, the outer PCR contained 40 cycles, the nested round 35. Nested round PCR products were analyzed on agarose gel and only clearly visible amplification products were used in the LiPA procedure. Quantification of viral RNA was obtained with the HIV Monitor™ test (Roche, Brussels, Belgium). Later on, new sets of primers for amplification were selected. For the amplification of HIV protease codon 30–84: outer sense primer prot16: 5'-CAGAGCCAACAGCCCCACCAG-3' (SEQ ID NO 501), outer antisense primer prot5: 5'-TTTTCTTCTGTCAATGGCCATTGTTT-3' (SEQ ID NO 502) were used. Annealing occurred at 50° C., extension at 68° C. and denaturation at 94° C. for 35 cycles for the outer PCR. For the nested PCR annealing occurred at 45° C., denaturation at 94° C. and extension at 92° C. with primers: nested sense primers prot2a-bio: 5'-bio-CCTCAAATCACTCTTTGGCAACG-3' (SEQ ID NO 503) and prot2b-bio: 5'-bio-CCTCSGSTCSCTCTTTGGCSSCG-3' (SEQ ED NO 504), and nested antisense primer prot31-bio: 5'-bio-AGTCAACAGATTTCTTTCCAAT-3' (SEQ ID NO 6). For the amplification of HIV protease codon 90, the outer PCR was as specified for HIV protease codon 30–84. For the nested PCR, nested sense primer prot41-bio: 5'-bio-CCTGTCAACATAATTGCAAG-3' (SEQ ID NO 505) and nested antisense primers prot6a: 5'-bio-CTGGTACAGTTTCAATAGGGCTAAT-3' (SEQ ID NO 506), prot6b: 5'-bio-CTGGTACAGTTTCAATA-GGACTAAT-3' (SEQ ID NO 507), prot6c: 5'-bio-CTGGTACAGTCTCAATAGGACTAAT-3' (SEQ ID NO 508), prot6d: 5'-bio-CTGGTACAGTCTCAA-TAGGGCTAAT-3' (SEQ ID NO 509) were used. For the nested PCR the annealing temperature occurred at 45° C. Primers were tested on a plasmid, which contained an HIV fragment of 1301 bp ligated in a pGEM-T vector. The fragment contains protease, reverse transcriptase and the primer sites of first and second round PCR. By restriction with SacI the plasmid is linearised.

Selected PCR products were cloned into the pretreated EcoRV site of the pGEMT vector (Promega). Recombinant clones were selected after α-complementation and restriction fragment length analysis, and sequenced using standard sequencing techniques with plasmid primers and internal HIV protease primers. Sometimes biotinylated fragments were directly sequenced with a dye-terminator protocol (Applied Biosystems) using the amplification primers. Alternatively, nested PCR was carried out with analogs of the nested primers, in which the biotin group was replaced with the T7- and SP6-primer sequence, respectively. These amplicons were than sequenced with an SP6- and T7-dye-primer procedure.

Example 2

Selection of a Reference Panel

Codon positions involving resistance to saquinavir, ritonavir, indinavir, nelfmiavir and VX-478 have been described (Shiazi et al. 1997). It was the aim to clone in plasmids those viral protease genes that are covering the different genetic motifs at those important codon positions conferring resistance against the described protease inhibitors.

After careful analysis of 312 protease gene sequences, obtained after direct sequencing of PCR fragments, a selection of 47 PCR fragments which covered the different target polymorphisms and mutations were retained and cloned in plasmids using described cloning techniques. The selection of samples originated from naive or drug-treated European, Brazilian or US patients. These 47 recombinant plasmids are used as a reference panel, a panel that was sequenced on both strands, and biotinylated PCR products from this panel were used to optimize probes for specificity and sensitivity.

Although this panel of 47 samples is a representative selection of clones at this moment, it is important to mention here that this selection is an fact only a temporally picture of the variability of the virus, and a continuous update of this panel will be mandatory. This includes on ongoing screening for the new variants of the virus, and recombinant cloning of these new motifs.

Probe Selection and LiPA Testing

To cover all the different genetic motifs in the reference panel, a total of 471 probes were designed (codon 30: 40 probes; codon 46/48: 72 probes; codon 50: 55 probes; codon 54: 54 probes, codon 82/84: 130 probes; codon 90: 120 probes). Table 3 shows the different probes that were selected for the different codon positions.

It was the aim to adapt all probes to react specifically under the same hybridization and wash conditions by carefully considering the % (G+C), the probe length, the final concentration of the buffer components, and hybridization temperature (Stuyver et al., 1997). Therefore, probes were provided enzymatically with a poly-T-tail using the TdT (Pharmacia) in a standard reaction condition, and purified via precipitation. For a limited number of probes with 3' T-ending sequences, an additional G was incorporated between the probe sequence and the poly-T-tail in order to limit the hybridizing part to the specific probe sequence and to exclude hybridization with the tail sequence. Probe pellets were dissolved in standard saline citrate (SSC) buffer and applied as horizontal parallel lines on a membrane strip. Control lines for amplification (probe 5' TAGGGGGAAT-TGGAGGTTTTAG 3' (SEQ ID NO: 125), HIV protease aa 47 to aa 54) and conjugate incubation (biotinylated DNA) were applied alongside. Probes were immobilized onto membranes by baking, and the membranes were sliced into 4 mm strips also called LiPA strips.

Selection of the amplification primers and PCR amplification was as described in example 1. In order to select specific reacting probes out of the 471 candidate probes, LiPA tests were performed with biotinylated PCR fragments from the reference panel. To perform LiPA tests, equal amounts (10 μl) of biotinylated amplification products and denaturation mixture (0.4 N NaOH/0.11% SDS) were mixed, followed by an incubation at room temperature for 5 minutes. Following this denaturation step, 2 ml hybridization buffer (2×SSC, 0.1% SDS, 50 mM Tris pH7.5) was added together with a membrane strip and hybridization was carried out at 39° C. for 30 min. Then, the hybridization mix was replaced by stringent washing buffer (same composition as hybridization buffer), and stringent washing occurred first at room temperature for 5 minutes and than at 39° C. for another 25 minutes. Buffers were than replaced to be suitable for the streptavidine alkaline phosphatase conjugate incubations. After 30 minutes incubation at room temperature, conjugate was rinsed away and replaced by the substrate components for alkaline phosphatase, Nitro-Blue-Tetrazolium and 5-Bromo-4-Chloro-3-Indolyl Phosphate. After 30 minutes incubation at room temperature, probes where hybridization occurred became visible because of the purple brown precipitate at these positions.

After careful analysis of the 471 probes, the most specific and sensitive probes (n=46) were finally selected, covering the natural and drug-selected variability in the vicinity of aa 30, 46, 48, 50, 54, 82, 84, and 90. FIG. 2 shows the reactivity of the finally selected probes with the reference panel.

Example 3

LiPA Testing on Clinical Samples

A total of 856 samples were tested on this selection of 46 specific probes. The geographical origin of these samples is as follows: USA:359; France: 154; UK:36; Brazil 58; Spain 35; Belgium 199; Luxembourg: 15.

From this population, a total of 144 samples were sequenced which allowed to separate the genotype B samples (94) from the non-B samples (50). After analysis of these genotyped samples on LiPA, the genotypic reactivity on the selected probes was scored. FIGS. 4A to 4F show these results for the different codon positions and for the genotype B versus non-B group. From these tables, it is clear that there is little difference in sequence usage for the different codon positions with resect to specific reactivities at the different probes.

The total collection of 856 samples was then tested on the available 46 probes. After dissection of those reactivities over the different probes and different geographical origin, the picture looks as is presented in FIGS. 5A to 5F. Again here, the majority of the sequences used at the different codon positions are restricted to some very abundant wild type motifs. It is important to mention here that the majority of these samples are taken from patients never treated with protease inhibitors, en therefore, the majority of the reactivities are found in wild type motifs. Nevertheless, it is clear from some codon positions that the variability at some codon positions in the mutant motif might be considerable, and again, a continuous update on heavily treated patients is mandatory. Another issue is the amount of double blank reactivities, which is in this approach reaching up to 5% in global; with some peak values for some countries for some codon positions: for example 13.8% for codon 82/85 in Brazil; and 18.1% for codon 90 in Belgium.

The continuous update resulted in a further selection of probes. This later configuration of the strip is indicated in table 7.

REFERENCES

Asseline U, Delarue M, Lancelot G, Toulme F, Thuong N (1984) Nucleic acid-binding molecules with high affinity and base sequence specificity: intercalating agents covalently linked to oligodeoxynucleotides. Proc. Natl. Acad. Sci. USA 81(11):3297–301.

Barany F. Genetic disease detection and DNA amplification using cloned thermostable ligase. Proc Natl Acad Sci USA 1991; 88: 189–193.

Bej A, Mahbubani M, Miller R, Di Cesare J, Haff L, Atlas R. Mutiplex PCR amplification and immobilized capture probes for detection of bacterial pathogens and indicators in water. Mol Cell Probes 1990; 4:353–365.

Compton J. Nucleic acid sequence-based amplification. Nature 1991; 350: 91–92.

Condra et al. 1995. In vivo emergence of HIV-1 variants resistant to multiple protease inhibitors. Nature 374: 569–571.

Condra et al. 1995. In vivo emergence of HIV-1 variants resistant to multiple protease inhibitors. Nature 374: 569–571.

Duck P. Probe amplifier s n based on chimeric cycling oligonucleotides. Biotechniques 1990; 9: 142–147.

Eberle et al. 1995. Resistance of HIV type 1 to proteinase inhibitor Ro 31-8959. AIDS Research and Human Retroviruses 11: 671–676.

Emini et al. 1994. Phenotypic and genotypic characterization of HIV-1 variants selected during treatment with the protease inhibitor L-735, L-524. Third International Workshop on HIV Drug Resistance, Kauai, Hi., USA.

Guatelli J, Whitfield K, Kwoh D, Barringer K, Richman D, Gengeras T. Isothermal, in vitro amplification of nucleic acids by a multienzyme reaction modeled after retroviral replication. Proc Natl Acad Sci USA 1990; 87: 1874–1878.

Huff et al. 1991. HIV protease: a novel chemotherapeutic target for AIDS. J. Med. Chem. 34: 2305–2314.

Hunter et al. 1994. Macromolecular interactions in the assembly of HIV and other retroviruses. Seminars in Virology 5: 71–83.

Kempf et al. 1994. Pharmacokinetic and in vitro selection studies with ABT-538, a potent inhibitor of HIV protease with high oral bioavailability. 34th Interscience Conference on Antimicrobial Agents and Chemotherapy, Orlando, Fla., USA.

Kohl et al. 1988. Active human immunodeficiency virus protease is required for viral infectivity. Proc. Natl. Acad. Sci. USA. 85:4686–4690.

Kwok S, Kellogg D, McKinney N, Spasic D, Goda L, Levenson C, Sinisky. Effects of primer-template mismatches on the polymerase chain reaction: Human immunodeficiency views type 1 model studies. Nucl. Acids Res. 1990; 18: 999.

Landgren U, Kaiser R, Sanders J, Hood L. A ligase-mediated gene detection technique. Science 1988; 241:1077–1080.

Lomeli H, Tyagi S, Printchard C, Lisardi P, Kramer F. Quantitative assays based on the use of replicatable hybridization probes. Clin Chem 1989; 35: 1826–1831.

Matsukura M, Shinozuka K, Zon G, Mitsuya H, Reitz M, Cohen J, Broder S (1987) Phosphorothioate analogs of oligodeoxynucleotides: inhibitors of replication and cytopathic effects of human immunodeficiency virus. Proc. Natl. Acad. Sci. USA 84(21):7706–10.

Meek et al. 1989. Proc. Natl. Acad. Sci. USA. 86: 1841–1845.

Miller P, Yano J, Yano E, Carroll C, Jayaram K, Ts'o P (1979) Nonionic nucleic acid analogues. Synthesis and characterization of dideoxyribonucleoside methylphosphonates. Biochemistry 18(23):5134–43.

Myers et al. 1996. Human retroviruses and AIDS 1996. Los Alamos Laboratory, Los Alamos, N.Mex. Navia et al. 1989. Three-dimensional structure of aspartyl protease from human immunodeficiency virus HIV-1. Nature 337: 615–620.

Nielsen P, Egholm M, Berg R. Buchardt O (1993) Sequence specific inhibition of DNA restriction enzyme cleavage by PNA. Nucleic-Acids-Res. 21(2): 197–200.

Nielsen P, Egholm M, Berg R, Buchardt O (1991) Sequence-selective recognition of DNA by strand displacement with a thymine-substituted polyamide. Science 254 (5037):1497–500.

Patick et al. 1996. Antiviral and resistance studies of AG1343, an orally bioavailable inhibitor of human immunodeficiency virus protease. Antimicrobial Agents and Chemotherapy 40: 292–297; 40: 1575 (erratum).

Peng et al. 1989. Role of human immunodeficiency virus type 1-specific protease in core protein maturation and viral infectivity. J. Virol. 63: 2550–2556.

Rao et al. 1996. Structural and modeling analysis of the basis of viral resistance to VX-478. Fifth International Workshop on HIV Drug Resistance, Whistler, Canada, abstract n°: 22.

Saiki R, Walsh P, Levenson C, Erlich H. Genetic analysis of amplified DNA with immobilized sequence-specific oligonucleotide probes Proc Natl Acad Sci USA 1989; 86:6230–6234.

Schmit et al. 1996. Resistance-related mutations in the HIV-1 protease gene of patients treated for 1 year with the protease inhibitor ritonavir (ABT-538). AIDS 10: 995–999.

Shinazi et al. 1997. Mutations in retroviral genes associated with drug resistance. International Antiviral News 5: 129–142.

Stuyver L, Rossau R, Wyseur A, et al. Typing of hepatitis C virus isolates and characterization of new subtypes using a line probe assay. J. Gen. Virol. 1993; 74: 1093–1102.

Tisdale et al. 1994. Comprehensive analysis of HIV-1 variants individually selected for resist to six HIV protease inhibitors. Third International Workshop on HIV Drug Resistance, Kauai, Hi., USA.

Wlodawer et al. 1993. Structure-based inhibitors of HIV-1 protease. Annu. Rev. Biochem. 62:543–585.

Wlodawer et al. 1989. Science 245: 616–621.

Wu D, Wallace B. The ligation amplification reaction (LAR)—amplification of specific DNA sequences using sequential rounds of template-dependent ligation. Genomics 1989; 4:560–569.

TABLE 1

| | 26 | 27 | 28 | 29 | 30 | 31 | 32 | 33 | 34 | 3 | Tm | lengte | Seq ID |
|---|---|---|---|---|---|---|---|---|---|---|---|---|---|
| | ACA | GGA | GCA | GAT | GAT | ACA | GTA | TTA | GAA | GAA | | | |
| pc30w25 | | | GCA | GAT | GAT | ACA | GT | | | | 40 | 14 | 31 |
| pc30w29 | | A | GCG | GAT | GAT | ACA | | | | | 36 | 13 | 35 |
| pc30w32 | | | GCA | GAT | GAC | ACA | GT | | | | 42 | 14 | 38 |
| pc30w36 | | | GCA | GAC | GAT | ACA | GG | | | | 40 | 14 | 42 |
| pc30m23 | | A | GCA | GAT | AAT | ACA | GT | | | | 40 | 15 | 29 |

| | 44 | 45 | 46 | 47 | 48 | 49 | 50 | 51 | 52 | | | | |
|---|---|---|---|---|---|---|---|---|---|---|---|---|---|
| | CCA | AAA | ATG | ATA | GGG | GGA | ATT | GGA | GGT | | | | |
| pc48w47 | | AAA | ATG | ATA | GGG | GGA | | | | | 42 | 15 | 93 |
| pc48w45 | | A | ATG | ATA | GGA | GGA | ATT | | | | 42 | 16 | 91 |
| pc48w72 | A | AAA | ATA | ATA | GGG | GGA | | | | | 42 | 16 | 120 |
| pc48m41 | | | ATG | ATA | GTG | GGA | ATT | | | | 40 | 15 | 87 |

| | 48 | 49 | 50 | 51 | 52 | 53 | 54 | | | | | | |
|---|---|---|---|---|---|---|---|---|---|---|---|---|---|
| | GGG | GGA | ATT | GGA | GGT | TTT | ATC | | | | | | |
| pc50w31 | | GGA | ATT | GGA | GGT | TTT | | | | | 42 | 15 | 151 |
| pc50w44 | | GGA | ATT | GGG | GGT | TTG | | | | | 42 | 15 | 164 |
| pc50w52 | | GA | ATT | GGA | GGC | TTG | | | | | | 14 | 172 |
| pc50m37 | GGG | GGA | GTT | GGA | | | | | | | 40 | 12 | 157 |

| | 51 | 52 | 53 | 54 | 55 | 56 | 57 | 58 | | | | | |
|---|---|---|---|---|---|---|---|---|---|---|---|---|---|
| | GGA | GGT | TTT | ATC | AAA | GTA | AGA | CAG | | | | | |
| pc54w3 | | GT | TTT | ATC | AAA | GTA | AGA | | | | 42 | 17 | 178 |
| pc54w34 | GA | GGT | TTT | ATC | AAA | GT | | | | | 42 | 16 | 212 |
| pc54w14 | | GGT | TTT | ATC | AAG | GTA | A | | | | 42 | 16 | 189 |
| pc54w19 | A | GGC | TTT | ATC | AAA | GTA | | | | | 42 | 16 | 194 |
| pc54w22 | GA | GGT | TTT | ATT | AAA | GTA | | | | | 42 | 17 | 197 |
| pc54w26 | A | GGT | TTC | ATT | AAG | GTA | | | | | 42 | 16 | 202 |
| pc54w27 | | GGT | TTT | ATT | AAG | GTA | A | | | | 40 | 16 | 204 |
| pc54m55 | A | GGT | TTT | GCC | AAA | GT | | | | | 38 | 15 | |
| pc54m35 | | GGT | TTT | GTC | AAA | GTA | | | | | 40 | 15 | 213 |
| pc54m37 | | GGT | TTT | GTC | AGA | GTA | | | | | 42 | 15 | 215 |

| | 78 | 79 | 80 | 81 | 82 | 83 | 84 | 85 | 86 | 87 | | | |
|---|---|---|---|---|---|---|---|---|---|---|---|---|---|
| | GGA | CCT | ACA | CCT | GTC | AAC | ATA | ATT | GGA | AGA | | | |
| pc82w91 | | | ACA | CCT | GTC | AAC | ATA | A | | | 44 | 16 | 318 |
| pc82w60 | | | CA | CCT | GTC | AAT | ATA | ATG | | | 42 | 17 | 287 |
| pc82w111 | | A | CCG | GTC | AAC | ATA | ATT | | | | 44 | 16 | 338 |
| pc82w89 | | | ACA | CCT | GTT | AAC | ATA | AG | | | 42 | 17 | 316 |
| pc82w42 | | | CA | CCT | GTC | AAC | GTA | | | | 42 | 14 | 269 |
| pc82m36 | | | ACA | CCT | ACC | AAC | ATA | | | | 42 | 15 | 263 |
| pc82m67 | | | ACA | CCT | ACC | AAC | GT | | | | 42 | 14 | 294 |
| pc82m38 | | | ACA | CCT | TTC | AAC | ATA | | | | 40 | 15 | 265 |
| pc82m105 | | | ACG | CCC | TTC | AAC | ATA | | | | 44 | 15 | 332 |
| pc82m127 | | | CA | CCT | TTC | AAC | GTA | ATG | | | 44 | 17 | 354 |
| pc82m40 | | | ACA | CCT | GCC | AAC | ATA | | | | 44 | 15 | 267 |
| pc82m63 | | | CA | CCT | GCC | AAT | ATA | AG | | | 42 | 16 | 290 |
| pc82m101 | | | ACA | CCT | ATC | AAC | ATA | ATG | | | 44 | 18 | 328 |

| | 86 | 87 | 88 | 89 | 90 | 91 | 92 | 93 | 94 | | | | |
|---|---|---|---|---|---|---|---|---|---|---|---|---|---|
| | GGA | AGA | AAT | CTG | TTG | ACT | CAG | ATT | GGT | | | | |
| pc90w27 | | | AAT | CTG | TTG | ACT | CA | | | | 38 | 14 | 384 |
| pc90w37 | | | AAT | CTG | TTG | ACT | CAG | ATG | | | 42 | 18 | 394 |
| pc90w39 | | GA | ACT | CTG | TTG | ACT | C | | | | 44 | 15 | 396 |
| pc90w50 | | | AAT | ATG | TTG | ACT | CAG | | | | 40 | 15 | 407 |
| pc90w52 | | | AAT | TTG | TTG | ACT | CAG | | | | 40 | 15 | 409 |
| pc90w69 | | GA | AAC | CTG | TTG | ACT | | | | | 40 | 14 | 426 |
| pc90w73 | | | | TG | TTG | ACA | CAG | CTT | G | | 44 | 15 | 430 |
| pc90w79 | | | | TG | TTG | ACC | CAG | ATT | G | | 44 | 15 | 436 |
| pc90m43 | | A | AAT | CTG | ATG | ACT | CA | | | | 40 | 15 | 400 |
| pc90m56 | | | AAT | ATG | ATG | ACC | CAG | | | | 42 | 15 | 413 |

TABLE 2

| Compound Protease Inhibitors | Amino acid change | Codon change |
|---|---|---|
| A-77003 | R8Q | CGA to CAA |
| | R8K | CGA to AAA |
| | V32I | GTA to ATA |
| | M46I | ATG to ATA |
| | M46L | ATG to TTC |
| | M46F | ATG to TTC |
| | M46V | ATG to GTG |
| | G48V | GGG to GTG |
| | A71V | GCT to GTT |
| | V82I | GTC to ATC |
| | V82A | GTC to GCC |
| | L63P | CTC to CCC |
| | A71T | GCT to ACT |
| | A71V | GCR to GTT |
| | G73S | GGT to GCT |
| | V82A | GTC to GCC |
| | V82F | GTC to TTC |
| | V82T | GTC to ACC |
| | I84V | ATA to GTA |
| | L90M | TTG to ATG |
| P9941 | V82A | GTC to GCC |
| Ro 31-8959 (saquinavir) | L10I | CTC to ATC |
| | G48V | GGG to GTG |
| | I54V | ATC to GTC |
| | I54V | ATA to GTA |
| | G73S | GGT to AGT |
| | V82A | GTC to GCC |
| | I84V | ATA to GTA |
| | L90M | TTG to ATG |
| RPI-312 | I84V | ATA to GTA |
| SC-52151 | L24V | TTA to GTA |
| | G48V | GGG to GTG |
| | A71V | GCT to GTT |
| | V75I | GTA to ATA |
| | P81T | CCT to ACT |
| | V82A | GTC to GCC |
| | N88D | AAT to GAT |
| SC-55389A | L10F | CTC to CGC |
| | N88S | AAT to AGT |
| SKF108842 | V82T | GTC to ACC |
| | I84V | ATA to GTA |
| SKF108922 | V82A | GTC to GCC |
| | V82T | GTC to ACC |
| VB 11,328 | L10F | CTC to GGC |
| | M46I | ATG to ATA |
| | I47V | ATA to CTA |
| | I50V | ATT to GTT |
| | I84V | ATA to GTA |
| VX-478 (141W94) | L10F | CTC to CGC |
| | M46I | ATG to ATA |
| | I47V | ATA to CTA |
| | I50V | ATT to GTT |
| | I84V | ATA to GTA |
| XM323 | L10F | CTC to CGC |
| | K45I | AAA to ATA |
| | M46L | ATG to CTG |
| | V82A | GTC to GCC |
| | V82I | GTC to ATC |
| | V82F | GTC to TTC |
| | I84V | ATA to GTA |
| | L97V | TTA to GTA |
| | I82T | ATC to ACC |
| A-75925 | V32I | GTA to ATA |
| ABT-538 (ritonavir) | K20R | AAG to AAA |
| | L33F | TTA to TTC |
| | M36I | ATG to ATA |
| | M46I | ATG to ATA |
| | I54L | ATC to ? |
| | I54V | ATC to GTC |
| | A71V | GTC to GTT |
| | V82F | GTC to TTC |
| | V82A | GTC to GCC |
| | V82T | GTC to ACC |
| | V82S | GTC to TCC |
| | I84V | ATA to GTA |
| | L90M | TTG to ATG |
| AG1343 (nelfinavir) | D30N | GAT to AAT |
| | M36I | |
| | M46I | ATG to ATA |
| | L63P | CTC to CCC |
| | A71V | GCT to GTT |
| | V77I | |
| | I84V | ATA to GTA |
| | N88D | |
| | L90M | TTG to ATG |
| BILA 1906 BS | V32I | GTA to ATA |
| | M46I | ATG to ATA |
| | M46L | ATG to TTG |
| | A71V | GCT to CTT |
| | I84A | ATA to GCA |
| | I84V | ATA to GTA |
| BILA 2011 (palinavir) | V32I | GTA to ATA |
| | A71V | GCT to GTT |
| | I84A | ATG to ATA |
| | L63P | CTC to CCC |
| BILA 2185 BS | L23I | CTA to ATA |
| BMS 186,318 | A71T | GCT to ACT |
| | V82A | GTC to GCC |
| DMP450 | L10F | CTC to TTC |
| | M46I | ATG to ATA |
| | D60E | GAT to GAA |
| | I84V | ATA to GTA |
| KNI-272 | V32I | GTA to ATA |
| MK-639 (L-735, 524, indinavir) | L10I | CTC to ATC |
| | L10R | CTC to CGC |
| | L10V | CTC to GTC |
| | K20M | AAG to ATG |
| | K20R | AAG to AAA |
| | L24I | TTA to ATA |
| | V32I | GTA to ATA |
| | M46I | ATG to ATA |
| | M46L | ATG to TTG |
| | I54V | ATC to GTC |

TABLE 3

| | 26 | 27 | 28 | 29 | 30 | 31 | 32 | 33 | 34 | 35 | length | Seq ID |
|---|---|---|---|---|---|---|---|---|---|---|---|---|
| | ACA | GGA | GCA | GAT | GAT | ACA | GTA | TTA | GAA | GAA | | |
| P30w1 | | A | GCA | GAT | GAT | ACA | GTA | TT | | | 18 | 7 |
| P30w2 | | GA | GCA | GAT | GAT | ACA | GTA | TT | | | 19 | 8 |
| P30w3 | | A | GCA | GAT | GAT | ACA | GTA | TTA | | | 19 | 9 |
| P30w4 | | GGA | GCA | GAT | GAT | ACA | GTA | TT | | | 20 | 10 |
| P30w5 | | GGA | GCA | GAT | GAT | ACA | GTA | TTA | | | 21 | 11 |
| P30w6 | ACA | GGA | GCA | GAT | GAT | ACA | | | | | 18 | 12 |
| P30w7 | CA | GGA | GCA | GAT | GAT | ACA | GT | | | | 19 | 13 |
| P30w8 | A | GGA | GCA | GAT | GAT | ACA | GTA | TG | | | 20 | 14 |
| P30w9 | | GGA | GCA | GAT | GAT | ACA | GTA | TG | | | 19 | 15 |
| P30w10 | ACA | GGA | GCA | GAT | GAT | ACA | GG | | | | 19 | 16 |
| P30m11 | | A | GCA | GAT | AAT | ACA | GTA | TT | | | 18 | 17 |
| P30m12 | | GA | GCA | GAT | AAT | ACA | GTA | TT | | | 19 | 18 |
| P30m13 | | A | GCA | GAT | AAT | ACA | GTA | TTA | | | 19 | 19 |
| P30m14 | | GGA | GCA | GAT | AAT | ACA | GTA | TT | | | 20 | 20 |
| P30m15 | | GGA | GCA | GAT | AAT | ACA | GTA | TTA | | | 21 | 21 |
| P30m15 | ACA | GGA | GCA | GAT | AAT | ACA | | | | | 18 | 22 |
| P30m17 | CA | GGA | GCA | GAT | AAT | ACA | GT | | | | 19 | 23 |
| P30m18 | A | GGA | GCA | GAT | AAT | ACA | GTA | TG | | | 20 | 24 |
| P30m19 | | GGA | GCA | GAT | AAT | ACA | GTA | TG | | | 19 | 25 |
| P30m20 | ACA | GGA | GCA | GAT | AAT | ACA | GG | | | | 19 | 26 |
| p30w21 | | A | GCA | GAT | GAT | ACA | GT | | | | 15 | 27 |
| p30w22 | | A | GCA | GAT | GAT | ACA | GTA | G | | | 16 | 28 |
| p30m23 | | A | GCA | GAT | AAT | ACA | GTA | | | | 15 | 29 |
| p30m24 | | A | GCA | GAT | AAT | ACA | GTA | G | | | 16 | 30 |
| p30w25 | | | GCA | GAT | GAT | ACA | GT | | | | 14 | 31 |
| p30w26 | | A | GCA | GAT | GAT | ACA | GG | | | | 14 | 32 |
| p30w27 | | | CA | GAT | GAT | ACA | GT | | | | 13 | 33 |
| p30w28 | | GA | GCG | GAT | GAT | ACA | | | | | 14 | 34 |
| p30w29 | | A | GCG | GAT | GAT | ACA | | | | | 13 | 35 |
| p30m30 | | | GCA | GAT | AAT | ACA | GTA | | | | 15 | 36 |
| p30m31 | | | GCA | GAT | AAT | ACA | GT | | | | 14 | 37 |
| p30w32 | | | GCA | GAT | GAC | ACA | GT | | | | 14 | 38 |
| p30w33 | | | CA | GAT | GAC | ACA | GTA | G | | | 14 | 39 |
| p30w34 | | | CA | GAT | GAT | ACA | ATA | TT | | | 16 | 40 |
| p30w35 | | | GCA | GAT | GAT | ACA | ATA | TG | | | 16 | 41 |
| p30w36 | | | GCA | GAC | GAT | ACA | GG | | | | 13 | 42 |
| p30w37 | | | GCA | GAC | GAT | ACA | GT | | | | 14 | 43 |
| p30w38 | | | A | GAT | GAT | ACA | ATA | TT | | | 15 | 44 |
| p30w39 | | | A | GAT | GAT | ACA | ATA | TTA | | | 16 | 45 |
| p30w40 | | | GCA | GAT | GAT | ACA | ATA | | | | 15 | 46 |

| | 44 | 45 | 46 | 47 | 48 | 49 | 50 | 51 | 52 | 53 | 54 | length | Seq ID |
|---|---|---|---|---|---|---|---|---|---|---|---|---|---|
| | CCA | AAA | ATG | ATA | GGG | GGA | ATT | GGA | GGT | TTT | ATC | | |
| P48w1 | | | | GTA | GGG | GGA | ATT | GGA | GGT | GG | | 18 | 47 |
| P48w2 | | | | GTA | GGG | GGA | ATT | GGA | GGT | TG | | 19 | 48 |
| P48w3 | | | | GTA | GGG | GGA | ATT | GGA | GGT | TTG | | 20 | 49 |
| P48w4 | | | | GTA | GGG | GGA | ATT | GGA | GGT | TTT | | 21 | 50 |
| P48w5 | | | G | GTA | GGG | GGA | ATT | GGA | GGT | TTG | | 21 | 51 |
| P48w6 | | | ATG | GTA | GGG | GGA | ATT | GGA | | | | 18 | 52 |
| P48w7 | | | ATG | GTA | GGG | GGA | ATT | GGA | G | | | 19 | 53 |
| P48w8 | | A | ATG | GTA | GGG | GGA | ATT | GGA | | | | 19 | 54 |
| P48w9 | | A | ATG | GTA | GGG | GGA | ATT | GGA | G | | | 20 | 55 |
| P48w10 | | A | ATG | GTA | GGG | GGA | ATT | GGA | GGG | GG | | 22 | 56 |
| P48w21 | | | ATA | ATA | GGG | GGA | ATT | GGA | | | | 18 | 57 |
| P48w22 | | | ATG | ATA | GGG | GGA | ATT | GGA | | | | 18 | 58 |
| P48w23 | | A | ATA | ATA | GGG | GGA | ATT | GGA | | | | 19 | 59 |
| P48w24 | | A | ATG | ATA | GGG | GGA | ATT | GGA | | | | 19 | 60 |
| P48w25 | | | | ATA | GGG | GGA | ATT | GGA | GGT | GG | | 18 | 61 |
| P48w26 | | | | ATA | GGG | GGA | ATT | GGA | GGT | TG | | 19 | 62 |
| P48w28 | | | | ATA | GGG | GGA | ATT | GGA | GGT | TTG | | 20 | 63 |
| P48w29 | | | | ATA | GGG | GGA | ATT | GGA | GGT | TTT | | 21 | 64 |
| P48m11 | | | | GTA | GTG | GGA | ATT | GGA | GGT | GG | | 18 | 65 |
| P48m12 | | | | GTA | GTG | GGA | ATT | GGA | GGT | TG | | 19 | 66 |
| P48m13 | | | | GTA | GTG | GGA | ATT | GGA | GGT | TTG | | 20 | 67 |
| P48m14 | | | | GTA | GTG | GGA | ATT | GGA | GGT | TTT | | 21 | 68 |
| P48m15 | | | G | GTA | GTG | GGA | ATT | GGA | GGT | TTG | | 21 | 69 |
| P48m16 | | | ATG | GTA | GTG | GGA | ATT | GGA | | | | 18 | 70 |
| P48m17 | | | ATG | GTA | GTG | GGA | ATT | GGA | G | | | 19 | 71 |
| P48m18 | | A | ATG | GTA | GTG | GGA | ATT | GGA | | | | 19 | 72 |
| P48m19 | | A | ATG | GTA | GTG | GGA | ATT | GGA | G | | | 20 | 73 |
| P48m20 | | A | ATG | GTA | GTG | GGA | ATT | GGA | GGG | GG | | 22 | 74 |
| P48m29 | | | | ATA | GTG | GGA | ATT | GGA | GGT | GG | | 18 | 75 |
| P48m30 | | | | ATA | GTG | GGA | ATT | GGA | GGT | TG | | 19 | 76 |
| P48m31 | | | ATG | ATA | GTG | GGA | ATT | GGA | | | | 18 | 77 |
| P48m32 | | | ATG | ATA | GTG | GGA | ATT | GGA | G | | | 19 | 78 |

TABLE 3-continued

| | | | | | | | length | Seq ID |
|---|---|---|---|---|---|---|---|---|
| p48m33 | A ATG ATA | GTG GGA | ATT GGA | | | | 19 | 79 |
| p48w34 | G ATA | GGG GGA | ATT G | | | | 14 | 80 |
| p48w35 | TG ATA | GGG GGA | ATT G | | | | 15 | 81 |
| p48w36 | TG ATA | GGG GGA | ATT GG | | | | 16 | 82 |
| p48w37 | ATG ATA | GGG GGA | ATT | | | | 15 | 83 |
| p48m38 | G ATA | GTG GGA | ATT G | | | | 14 | 84 |
| p48m39 | TG ATA | GTG GGA | ATT G | | | | 15 | 85 |
| p48m40 | TG ATA | GTG GGA | ATT GG | | | | 16 | 86 |
| p48m41 | ATG ATA | GTG GGA | ATT | | | | 15 | 87 |
| p48w42 | ATA ATA | GGG GGA | ATT | | | | 15 | 88 |
| p48w43 | TG ATA | GGG GGA | GTT | | | | 14 | 89 |
| p48w44 | G ATA | GGG GGA | GTT G | | | | 14 | 90 |
| p48w45 | A ATG ATA | GGA GGA | ATT | | | | 16 | 91 |
| p48w46 | ATG ATA | GGG GGA | ATT | | | | 15 | 92 |
| p48w47 | AAA ATG ATA | GGG GGA | | | | | 15 | 93 |
| p48w48 | A AAA ATG ATA | GGG GG | | | | | 15 | 94 |
| p48w49 | AA ATG ATA | GGG GGA | AG | | | | 15 | 95 |
| p48w50 | AAA ATA ATA | GGG GGA | AG | | | | 16 | 96 |
| p48w51 | AAA ATA AAA | AT | | | | | 15 | 97 |
| p48m52 | AAA ATG ATA | GTG GGA | AG | | | | 16 | 98 |
| p48w52b | AAA TTG ATA | GGG GG | | | | | 14 | 99 |
| p48m53 | AAA ATG ATA | GTG GGA | | | | | 15 | 100 |
| p48w53b | AAA TTG ATA | GGG GGA | | | | | 15 | 101 |
| p48w54 | CA AAA TTG ATA | G | | | | | 15 | 102 |
| p48w55 | ATG GTA | GGG GGA | ATT | | | | 15 | 103 |
| p48w56 | AA ATG GTA | GGG GGA | | | | | 14 | 104 |
| p48w57 | A AAA ATG GTA | GGG G | | | | | 14 | 105 |
| p48w58 | ATG ATA | GGG GAA | ATT | | | | 15 | 106 |
| p48w59 | ATA | GGG GAA | ATT GGA | | | | 15 | 107 |
| p48w60 | ATA | GGG GAA | ATT GGA G | | | | 16 | 108 |
| p48w61 | ATG ATA | GGG GGG | ATT | | | | 15 | 109 |
| p48w62 | ATA | GGG GGG | ATT GG | | | | 14 | 110 |
| p48w63 | A | GGG GGG | ATT GGA | | | | 13 | 111 |
| p48w64 | AAA ATA | GTG GGA | | | | | 15 | 112 |
| p48m65 | A AAA ATA | GTG GGA | | | | | 16 | 113 |
| p48m66 | CA AAA ATA ATA | GTG GG | | | | | 16 | 114 |
| p48m67 | AAA TTG ATA | GTG GGA | | | | | 15 | 115 |
| p48m68 | A AAA TTG ATA | GTG GGA | | | | | 16 | 116 |
| p48m69 | CA AAA TTG ATA | GTG G | | | | | 15 | 117 |
| p48w70 | AAA ATG ATA | GGG GG | | | | | 14 | 118 |
| p48w71 | A AAA ATG GGG | G | | | | | 14 | 119 |
| pc48w72 | A AAA ATA ATA | GGG GGA | | | | | 16 | 120 |

| | 45 | 46 | 47 | 48 | 49 | 50 | 51 | 52 | 53 | 54 | length | Seq ID |
|---|---|---|---|---|---|---|---|---|---|---|---|---|
| | AAA | ATG | GTA | GGG | GGA | ATT | GGA | GGT | TTT | ATC | | |
| P50w1 | | | | GGG | GGA | ATT | GGA | GGT | TTT | | 18 | 121 |
| P50w2 | | | A | GGG | GGA | ATT | GGA | GGT | TTT | | 19 | 122 |
| P50w3 | | | TA | GGG | GGA | ATT | GGA | GGT | TTT | | 20 | 123 |
| P50w4 | | | A | GGG | GGA | ATT | GGA | GGT | TTT | AG | 20 | 124 |
| P50w5 | | | TA | GGG | GGA | ATT | GGA | GGT | TTT | AG | 21 | 125 |
| P50w6 | | | GTA | GGG | GGA | ATT | GGA | GGT | TGG | | 19 | 126 |
| P50w7 | | G | GTA | GGG | GGA | ATT | GGA | GGT | TGG | | 20 | 127 |
| P50w8 | | | GTA | GGG | GGA | ATT | GGA | GGT | TTG | | 20 | 128 |
| P50w9 | | | GTA | GGG | GGA | ATT | GGA | GGT | TTT | | 20 | 129 |
| P50w10 | | TG | GTA | GGG | GGA | ATT | GGA | GGT | GG | | 20 | 130 |
| p50w21 | | | | GG | GGA | ATT | GGA | GGT | TTT | | 17 | 131 |
| P50w22 | | | | GG | GGA | ATT | GGA | GGT | TTG | | 16 | 132 |
| P50w23 | | | | GG | GGA | ATT | GGA | GGT | TTT | AG | 18 | 133 |
| P50w24 | | | | GG | GGA | ATT | GGA | GGT | TG | | 15 | 134 |
| P50w25 | | | | G | GGA | ATT | GGA | GGT | TTT | AT | 18 | 135 |
| P50w26 | | | | GG | GGA | ATT | GGA | GGT | TTT | | 17 | 136 |
| P50m11 | | | | GGG | GGA | GTT | GGA | GGT | TTT | | 18 | 137 |
| P50m12 | | | A | GGG | GGA | GTT | GGA | GGT | TTT | | 19 | 138 |
| P50m13 | | | TA | GGG | GGA | GTT | GGA | GGT | TTT | | 20 | 139 |
| P50m14 | | | A | GGG | GGA | GTT | GGA | GGT | TTT | AG | 20 | 140 |
| P50m15 | | | TA | GGG | GGA | GTT | GGA | GGT | TTT | AG | 21 | 141 |
| P50m16 | | | GTA | GGG | GGA | GTT | GGA | GGT | TGG | | 19 | 142 |
| P50m17 | | G | GTA | GGG | GGA | GTT | GGA | GGT | TGG | | 20 | 143 |
| P50m18 | | | GTA | GGG | GGA | GTT | GGA | GGT | TTG | | 20 | 144 |
| P50m19 | | | GTA | GGG | GGA | GTT | GGA | GGT | TTT | ATC | 21 | 145 |
| P50m20 | | TG | GTA | GGG | GGA | GTT | GGA | GGT | GG | | 20 | 146 |
| P50m27 | | | | GG | GGA | GTT | GGA | GGT | TTG | | 19 | 147 |
| P50m28 | | | | GG | GGA | GTT | GGA | GGT | TTT | AG | 18 | 148 |
| P50m29 | | | | GG | GGA | GTT | GGA | GGT | TG | | 15 | 149 |
| P50m30 | | | | G | GGA | GTT | GGA | GGT | TTT | AT | 18 | 150 |
| p50w31 | | | | | GGA | ATT | GGA | GGT | TTT | | 15 | 151 |
| p50w32 | | | | G | GGA | ATT | GGA | GGT | TGG | | 15 | 152 |
| p50m33 | | | | | GGA | GTT | GGA | GGT | TTT | | 15 | 153 |

TABLE 3-continued

|  |  |  |  |  |  |  |  | length | Seq ID |
|---|---|---|---|---|---|---|---|---|---|
| p50m34 |  | G | GGA | GTT | GGA | GGT | TGG | 14 | 154 |
| p50m35 |  | GGG | GGA | GTT | GGA | G |  | 13 | 155 |
| p50m36 |  | GG | GGA | GTT | GGA | G |  | 12 | 156 |
| p50m37 |  | GGG | GGA | GTT | GGA |  |  | 12 | 157 |
| p50w38 |  |  | GGA | ATT | GGG | GGT | TTG | 14 | 158 |
| p50w39 |  |  | GA | ATT | GGG | GGT | TTT | 14 | 159 |
| p50w40 |  |  | GA | ATT | GGG | GGT | TTT AG | 15 | 160 |
| p50w41 |  |  | GGA | ATT | GGG | GGT | TG | 13 | 161 |
| p50w42 |  |  | GGA | ATT | GGG | GGT | G | 12 | 162 |
| p50w43 |  |  | GA | ATT | GGG | GGT | TG | 12 | 163 |
| p50w44 |  |  | GA | ATT | GGG | GGT | TTG | 13 | 164 |
| p50w45 |  | GGG | GGA | ATT | GCA | G |  | 13 | 165 |
| p50w46 |  |  | GGA | ATT | GCA | GGT | TG | 14 | 166 |
| p50w47 |  |  | GGA | ATT | GCA | GGT | G | 13 | 167 |
| p50w48 |  |  | GGA | ATT | GGA | GGG | TTG | 14 | 168 |
| p50w49 |  |  | GA | ATT | GGA | GGG | TTG | 13 | 169 |
| p50w50 |  |  | GA | ATT | GGA | GGG | TTT | 14 | 170 |
| p50w51 |  |  | GGA | ATT | GGA | GGC | TTG | 14 | 171 |
| p50w52 |  |  | GA | ATT | GGA | GGC | TTG | 13 | 172 |
| p50w53 |  |  | GA | ATT | GGA | GGC | TTT | 14 | 173 |
| p50m54 |  |  | GGA | GTT | GGA | GGT | TTG | 15 | 174 |
| p50m55 |  |  | GA | GTT | GGA | GGT | TTT | 14 | 175 |

|  | 51 | 52 | 53 | 54 | 55 | 56 | 57 | 58 | length | Seq ID |
|---|---|---|---|---|---|---|---|---|---|---|
|  | GGA | GGT | TTT | ATC | AAA | GTA | AGA | CAG |  |  |
| p54w1 |  | GGT | TTT | ATC | AAA | GTA | A |  | 16 | 176 |
| p54w2 |  | GT | TTT | ATC | AAA | GTA | AG |  | 16 | 177 |
| p54w3 |  | GT | TTT | ATC | AAA | GTA | AGA |  | 17 | 178 |
| p54w4 |  | T | TTT | ATC | AAA | GTA | AGA |  | 16 | 179 |
| p54w5 |  | GGT | TTT | ATC | AAA | GTA |  |  | 15 | 180 |
| p54w6 |  | GT | TTT | ATC | AAA | GTA |  |  | 15 | 181 |
| p54m7 |  | GGT | TTT | GCC | AAA | GTA |  |  | 15 | 182 |
| p54m8 |  | GT | TTT | GCC | AAA | GTA | A |  | 15 | 183 |
| p54m9 |  | GT | TTT | GCC | AAA | GTA | AG |  | 16 | 184 |
| p54m10 |  | T | TTT | GCC | AAA | GTA | AGA |  | 16 | 185 |
| p54m11 |  | GGT | TTT | GCC | AAA | GT |  |  | 14 | 186 |
| p54m12 |  | GT | TTT | GCC | AAA | GTA |  |  | 14 | 187 |
| p54w13 |  | GT | TTT | ATC | AAG | GTA | AA |  | 16 | 188 |
| p54w14 |  | GGT | TTT | ATC | AAG | GTA | A |  | 16 | 189 |
| p54w15 | A | GGT | TTT | ATC | AAG | GTA |  |  | 16 | 190 |
| p54w16 |  | GT | TTT | ATC | AAA | GTC | AGA |  | 17 | 191 |
| p54w17 |  |  | TTT | ATC | AAA | GTC | AGA | C | 16 | 192 |
| p54w18 | A | GGC | TTT | ATC | AAA | GTA | A |  | 17 | 193 |
| p54w19 | A | GGC | TTT | ATC | AAA | GTA |  |  | 16 | 194 |
| p54w20 | A | GGT | TTT | ATT | AAA | GTA | A |  | 17 | 195 |
| p54m21 |  | GGT | TTT | ATT | AAA | GTA | AG |  | 17 | 196 |
| p54w22 | GA | GGT | TTT | ATT | AAA | GTA |  |  | 17 | 197 |
| p54m22 | GA | GGT | TTT | ATT | AAA | GTA |  |  | 17 | 198 |
| p54m23 |  | GGT | TTT | ATT | GGT | TTT | AT |  | 16 | 199 |
| p54m24 |  | GGT | TTC | ATT | AAG | GTA |  |  | 15 | 200 |
| p54m25 |  | GGT | TTC | ATT | AAG | GTA | A |  | 16 | 201 |
| p54w26 | A | GGT | TTC | ATT | AAG | GTA |  |  | 16 | 202 |
| p54m26 | A | GGT | TTC | ATT | AAG | GTA |  |  | 16 | 203 |
| p54w27 |  | GGT | TTT | ATT | AAG | GTA | A |  | 16 | 204 |
| p54m27 |  | GGT | TTT | ATT | AAG | GTA | A |  | 16 | 205 |
| p54m28 | A | GGT | TTT | ATT | AAG | GTA |  |  | 16 | 206 |
| p54m29 | GA | GGT | TTT | ATT | AAG | GT |  |  | 16 | 207 |
| p54m30 |  | GGT | TTT | ATT | AAG | GTA | AG |  | 17 | 208 |
| p54w31 |  | GGT | TTT | ATC | AAA | GTA | A |  | 16 | 209 |
| p54w32 | A | GGT | TTT | ATC | AAA | GTA | A |  | 17 | 210 |
| p54w33 | A | GGT | TTT | ATC | AAA | GTA |  |  | 16 | 211 |
| p54w34 | GA | GGT | TTT | ATC | AAA | GT |  |  | 16 | 212 |
| p54m35 |  | GGT | TTT | GTC | AAA | GTA |  |  | 15 | 213 |
| p54m36 |  | GGT | TTT | GTC | AAA | GTA | A |  | 16 | 214 |
| p54m37 |  | GGT | TTT | GTC | AGA | GTA |  |  | 15 | 215 |
| p54m38 |  | GGT | TTT | GTC | AGA | GTA | A |  | 16 | 216 |
| p54w39 |  | GGG | TTT | ATC | AAA | GTA |  |  | 15 | 217 |
| p54w40 |  | GGG | TTT | ATC | AAA | GTA | A |  | 16 | 218 |
| p54w41 |  | GGC | TTC | ATC | AAA | GT |  |  | 14 | 219 |
| p54w42 | GA | GGC | TTC | ATC | AAA |  |  |  | 14 | 220 |
| p54m48 |  | GGT | TTT | GTC | AAA | GT |  |  | 14 | 221 |
| p54m49 |  | GT | TTT | GTC | AGA | GTA |  |  | 14 | 222 |
| p54m50 |  | GGT | TTT | GTC | AGA | GT |  |  | 14 | 223 |
| p54w51 | A | GGT | TTA | ATC | AAA | GTA |  |  | 16 | 224 |
| p54w52 | GA | GGT | TTA | ATC | AAA | GT |  |  | 16 | 225 |
| p54m53 |  | GGT | TTT | ACC | AAA | GTA |  |  | 15 | 226 |
| p54m54 |  | GGT | TTT | ACC | AAA | GT |  |  | 14 | 227 |

TABLE 3-continued

|       | 78  | 79  | 80  | 81  | 82  | 83  | 84  | 85  | 86  | 87  | length | Seq ID |
|-------|-----|-----|-----|-----|-----|-----|-----|-----|-----|-----|--------|--------|
|       | GGA | CCT | ACA | CCT | GTC | AAC | ATA | ATT | GGA | AGA |        |        |
| P82w1 |     | CCT | ACA | CCT | GTC | AAC | ATA | AG  |     |     | 19     | 228    |
| P82w2 |     | CCT | ACA | CCT | GTC | AAC | ATA | ATG |     |     | 20     | 229    |
| P82w3 |     | CCT | ACA | CCT | GTC | AAC | ATA | ATT |     |     | 21     | 230    |
| P82w4 | A   | CCT | ACA | CCT | GTC | AAC | ATA | AG  |     |     | 20     | 231    |
| P82w5 | A   | CCT | ACA | CCT | GTC | AAC | ATA | ATG |     |     | 21     | 232    |
| P82w6 | A   | CCT | ACA | CCT | GTC | AAC | ATA |     |     |     | 19     | 233    |
| P82w7 | GA  | CCT | ACA | CCT | GTC | AAC | ATA |     |     |     | 20     | 234    |
| P82w8 |     |     | CA  | CCT | GTC | AAC | ATA | ATT | GGA |     | 20     | 235    |
| P82w9 |     |     | A   | CCT | GTC | AAC | ATA | ATT | GGA | A   | 20     | 236    |
| P82w10 |    |     | ACA | CCT | GTC | AAC | ATA | ATT | GG  |     | 20     | 237    |
| P82W21 |    |     | A   | CCT | GTC | AAC | ATA | ATT | GGA |     | 19     | 238    |
| P82m11 |    | CCT | ACA | CCT | ACC | AAC | ATA | AG  |     |     | 19     | 239    |
| P82m12 |    | CCT | ACA | CCT | ACC | AAC | ATA | ATG |     |     | 20     | 240    |
| P82m13 |    | CCT | ACA | CCT | ACC | AAC | ATA | ATT |     |     | 21     | 241    |
| P82m14 | A  | CCT | ACA | CCT | ACC | AAC | ATA | AG  |     |     | 20     | 242    |
| P82m15 | A  | CCT | ACA | CCT | ACC | AAC | ATA | ATG |     |     | 21     | 243    |
| P82m16 | A  | CCT | ACA | CCT | ACC | AAC | ATA |     |     |     | 19     | 244    |
| P82m17 | GA | CCT | ACA | CCT | ACC | AAC | ATA |     |     |     | 20     | 245    |
| P82m18 |    |     | CA  | CCT | ACC | AAC | ATA | ATT | GGA |     | 20     | 246    |
| P82m19 |    |     | A   | CCT | ACC | AAC | ATA | ATT | GGA | A   | 20     | 247    |
| P82m20 |    |     | ACA | CCT | ACC | AAC | ATA | ATT | G   |     | 19     | 248    |
| P82m22 |    | CCT | ACA | CCT | TTC | AAC | ATA | ATT |     |     | 21     | 249    |
| P82m23 |    | CCT | ACA | CCT | GCC | AAC | ATA | ATT |     |     | 21     | 250    |
| P82m24 |    | CCT | ACA | CCT | TCC | AAC | ATA | ATT |     |     | 21     | 251    |
| P82m25 |    |     | A   | CCT | TTC | AAC | ATA | ATT | GGA | A   | 20     | 252    |
| P82m26 |    |     | A   | CCT | GCC | AAC | ATA | ATT | GGA | A   | 20     | 253    |
| P82m27 |    |     | A   | CCT | TTC | AAC | ATA | ATT | GGA | A   | 20     | 254    |
| P82m28 |    |     | A   | CCT | ACC | AAC | ATA | ATT |     |     | 16     | 255    |
| P82m29 |    |     | A   | CCT | TTC | AAC | ATA | ATT | GGA |     | 19     | 256    |
| P82m30 |    |     | A   | CCT | GCC | AAC | ATA | ATT | GGA |     | 19     | 257    |
| P82m31 |    |     | A   | CCT | TCC | AAC | ATA | ATT | GGA |     | 19     | 258    |
| P82w32 |    |     | T   | ACA | CCT | GTC | AAC | AT  |     |     | 15     | 259    |
| P82w33 |    |     | T   | ACA | CCT | GTC | AAC | ATA |     |     | 16     | 260    |
| P82w34 |    |     |     | ACA | CCT | GTC | AAC | ATA |     |     | 15     | 261    |
| P82w35 |    |     |     | CA  | CCT | GTC | AAC | ATA |     |     | 14     | 262    |
| P82m36 |    |     |     | ACA | CCT | ACC | AAC | ATA |     |     | 15     | 263    |
| P82m37 |    |     |     | CA  | CCT | ACC | AAC | ATA |     |     | 14     | 264    |
| P82m38 |    |     |     | ACA | CCT | TTC | AAC | ATA |     |     | 15     | 265    |
| P82m39 |    |     |     | CA  | CCT | TTC | AAC | ATA |     |     | 14     | 266    |
| P82m40 |    |     |     | ACA | CCT | GCC | AAC | ATA |     |     | 15     | 267    |
| P82m41 |    |     |     | CA  | CCT | GCC | AAC | ATA |     |     | 14     | 268    |
| P82w42 |    |     |     | CA  | CCT | GTC | AAC | GTA |     |     | 14     | 269    |
| P82w43 |    |     |     | CA  | CCT | GTC | AAC | GT  |     |     | 13     | 270    |
| P82w44 |    | CCT | ACA | CCT | GTC | AAC |     |     |     |     | 15     | 271    |
| P82w45 |    |     | T   | ACG | CCT | GTC | AAC | AT  |     |     | 15     | 272    |
| P82w46 |    |     | CT  | ACG | CCT | GTC | AAC | AG  |     |     | 15     | 273    |
| P82m47 |    |     |     | ACA | CCT | TCC | AAC | ATA |     |     | 15     | 274    |
| P82m48 |    |     |     | CA  | CCT | TCC | AAC | ATA |     |     | 14     | 275    |
| P82m49 |    |     |     | ACA | CCT | TCC | AAC | AT  |     |     | 14     | 276    |
| P82m50 |    |     |     | ACA | CCT | ATC | AAC | ATA |     |     | 15     | 277    |
| P82m51 |    |     |     | CA  | CCT | ATC | AAC | ATA | AG  |     | 15     | 278    |
| P82m52 |    |     |     | CA  | CCT | ATC | AAC | ATA | ATG |     | 16     | 279    |
| P82m53 |    |     |     | A   | CCT | ATC | AAC | ATA | ATG |     | 15     | 280    |
| P82w54 |    |     |     |     | CCT | GTC | AAC | ATA | ATT |     | 15     | 281    |
| P82w55 |    |     |     |     | CCT | GTC | AAC | ATA | ATT | G   | 16     | 282    |
| P82w56 |    |     |     | A   | CCT | GTT | AAC | ATA | ATG |     | 15     | 283    |
| P82w57 |    |     |     |     | CCG | GTC | AAC | ATA | ATT |     | 15     | 284    |
| P82w58 |    |     |     | ACG | CCT | GTC | AAC | AT  |     |     | 14     | 285    |
| P82w59 |    |     |     |     | CCT | GTC | AAT | ATA | ATT |     | 15     | 286    |
| P82w60 |    |     |     | CA  | CCT | GTC | AAT | ATA | ATG |     | 16     | 287    |
| P82w61 |    |     |     | ACA | CCT | GTC | AAT | ATA | AG  |     | 16     | 288    |
| P82m62 |    |     |     |     | CCT | GCC | AAT | ATA | ATT |     | 15     | 289    |
| P82m63 |    |     |     | CA  | CCT | GCC | AAT | ATA | AG  |     | 15     | 290    |
| P82m64 |    |     |     |     | CCT | ACC | AAC | GTA | ATT |     | 15     | 291    |
| P82m65 |    |     |     |     | CCT | ACC | AAC | GTA | ATG |     | 14     | 292    |
| P82m66 |    |     |     | CA  | CCT | ACC | AAC | GTA |     |     | 14     | 293    |
| P82m67 |    |     |     | ACA | CCT | ACC | AAC | GT  |     |     | 14     | 294    |
| P82m68 |    |     |     |     | CCT | TTC | AAC | GTA | ATT |     | 15     | 295    |
| P82m69 |    |     |     | CA  | CCT | TTC | AAC | GTA | AG  |     | 15     | 296    |
| P82m70 |    |     |     | ACA | CCT | TTC | AAC | GTA |     |     | 15     | 297    |
| P82m71 |    |     |     | A   | CCT | TTC | AAC | GTA | ATG |     | 15     | 298    |
| p82w72 |    |     |     |     | CT  | GTC | AAT | ATA | ATT | G   | 15     | 299    |
| p82w73 |    |     |     |     | CCT | GTC | AAT | ATA | ATT | G   | 16     | 300    |
| p82w74 |    |     |     | A   | CCT | GTC | AAT | ATA | ATT |     | 16     | 301    |
| p82w75 |    |     |     |     | CT  | GTC | AAT | ATA | ATT | GG  | 16     | 302    |
| p82w76 |    | CCT | ACG | CCT | GTC | AA  |     |     |     |     | 14     | 303    |

TABLE 3-continued

| | | | | | | | | length | Seq ID |
|---|---|---|---|---|---|---|---|---|---|
| p82w77 | | CT ACG | CCT GTC | AAC | | | | 14 | 304 |
| p82w78 | A | CCT ACG | CCT GTC | AA | | | | 15 | 305 |
| p82w79 | A | CCT ACG | CCT GTC | A | | | | 14 | 306 |
| p82w80 | | T ACA | CCG GTC | AAC | A | | | 14 | 307 |
| p82w81 | | CT ACA | CCG GTC | AA | | | | 13 | 308 |
| p82w82 | | CCT ACA | CCG GTC | A | | | | 13 | 309 |
| p82w83 | | CA | CCT GTC | AAC | ATA | A | | 15 | 310 |
| p82w84 | | A | CCT GTC | AAC | ATA | AT | | 15 | 311 |
| p82w85 | | CT ACA | CCT GTC | AAC | A | | | 15 | 312 |
| p82w86 | | ACA | CCT GTC | AAC | AT | | | 14 | 313 |
| p82w87 | | A | CCT GTT | AAC | ATA | ATT | G | 17 | 314 |
| p82w88 | | CA | CCT GTT | AAC | ATA | AG | | 15 | 315 |
| p82w89 | | ACA | CCT GTT | AAC | ATA | AG | | 16 | 316 |
| p82w90 | | TCA | CCT GTC | AAC | ATA | | | 14 | 317 |
| p82w91 | | ACA | CCT GTC | AAC | ATA | A | | 16 | 318 |
| p82w92 | | CA | CCT GTC | AAC | ATA | AT | | 16 | 319 |
| p82w93 | | | CCT GTC | AAC | ATA | ATT | | 15 | 320 |
| p82w94 | | A | CCT GTC | AAC | ATA | ATT | | 16 | 321 |
| p82w95 | | | CCT GTC | AAC | ATA | ATT | G | 16 | 322 |
| p82w96 | CCT | ACA | CCT GTC | AA | | | | 14 | 323 |
| p82w97 | | T | GTC | AAC | ATA | ATT | GG | 15 | 324 |
| p82w98 | | T | GTC | AAC | ATA | ATT | GGA | 16 | 325 |
| p82m99 | | ACA | CCT TTC | AAC | ATA | A | | 16 | 326 |
| p82m100 | T | ACA | CCT TTC | AAC | ATA | | | 16 | 327 |
| p82m101 | | ACA | CCT ATC | AAC | ATA | ATG | | 17 | 328 |
| p82m102 | | ACA | CCT ATC | AAC | ATA | AG | | 16 | 329 |
| p82m103 | | CA | CCT GCC | AAT | ATA | ATG | | 16 | 330 |
| p82m104 | | ACA | CCT GCC | AAT | ATA | AG | | 16 | 331 |
| p82m105 | | ACG | CCC TTC | AAC | ATA | | | 15 | 332 |
| p82m106 | | CG | CCC TTC | AAC | ATA | AG | | 15 | 333 |
| p82m107 | T | ACG | CCC TTC | AAC | AT | | | 15 | 334 |
| p82w108 | | CT ACA | CCG GTC | AAC | | | | 14 | 335 |
| p82w109 | | CCT ACA | CCG GTC | AA | | | | 14 | 336 |
| p82w110 | | A | CCG GTC | AAC | ATA | ATG | | 15 | 337 |
| p82w111 | | A | CCG GTC | AAC | ATA | ATT | | 16 | 338 |
| p82w112 | | CT ACA | CCA GTC | AAC | | | | 14 | 339 |
| p82w113 | | CT ACA | CCA GTC | AAC | A | | | 15 | 340 |
| p82w114 | | ACA | CCA GTC | AAC | ATA | | | 15 | 341 |
| p82w115 | | ACA | CCA GTC | AAC | ATA | AG | | 16 | 342 |
| p82w116 | | T ACG | CCT GTC | AAC | AT | | | 15 | 343 |
| p82w117 | | ACG | CCT GTC | AAC | ATA | | | 15 | 344 |
| p82w118 | | T ACG | CCT GTC | AAC | A | | | 14 | 345 |
| p82m119 | | CCT ACA | CCT TTC | AAC | | | | 15 | 346 |
| p82m120 | | CT ACA | CCT TTC | AAC | | | | 14 | 347 |
| p82m121 | A | CCT ACA | CCT TTC | AA | | | | 15 | 348 |
| p82w122 | | ACG | CCT GTC | AAC | ATA | AGG | | 16 | 349 |
| p82w123 | | T ACG | CCT GTC | AAC | ATA | | | 16 | 350 |
| p82w124 | | CG | CCT GTC | AAC | ATA | AGG | | 15 | 351 |
| p82m125 | | T ACA | CCT TTC | AAC | GTA | | | 16 | 352 |
| p82m126 | | ACA | CCT TTC | AAC | GTA | AGG | | 16 | 353 |
| p82m127 | | CA | CCT TTC | AAC | GTA | ATG | | 16 | 354 |
| p82m128 | | A | CCT TTC | AAC | GTA | ATT | | 16 | 355 |
| p82o129 | | | C | AAC | GTA | ATT | GGA AGA | 16 | 356 |
| p82o130 | | | C | AAC | GTA | ATT | GGA AG | 15 | 357 |

| | 86 | 87 | 88 | 89 | 90 | 91 | 92 | 93 | 94 | length | Seq ID |
|---|---|---|---|---|---|---|---|---|---|---|---|
| | GGA | AGA | AAT | CTG | TTG | ACT | CAG | ATT | GGT | | |
| P90w1 | | A | AAT | CTG | TTG | ACT | CAG | | | 16 | 358 |
| P90w2 | | GA | AAT | CTG | TTG | ACT | CAG | | | 17 | 359 |
| P90w3 | | GA | AAT | CTG | TTG | ACT | CAG | AGG | | 18 | 360 |
| P90w4 | | A | AAT | CTG | TTG | ACT | CAG | AGG | | 17 | 361 |
| P90w5 | | AGA | AAT | CTG | TTG | ACT | CAG | AGG | | 19 | 362 |
| P90w6 | | AGA | AAT | CTG | TTG | ACT | CAG | ATG | | 20 | 363 |
| P90w7 | | AGA | AAT | CTG | TTG | ACT | CAG | ATT | | 21 | 364 |
| P90w8 | | AGA | AAT | CTG | TTG | ACT | CAG | ATT | GG | 20 | 365 |
| P90w9 | GA | AGA | AAT | CTG | TTG | ACT | CAG | AGG | | 21 | 366 |
| P90w10 | A | AGA | AAT | CTG | TTG | ACT | CAG | ATG | | 21 | 367 |
| P90m11 | | AGA | AAT | CTG | ATG | ACT | CAG | ATG | | 20 | 368 |
| P90m12 | | AGA | AAT | CTG | ATG | ACT | CAG | ATT | | 21 | 369 |
| P90m13 | A | AGA | AAT | CTG | ATG | ACT | CAG | AGG | | 20 | 370 |
| P90m14 | GA | AGA | AAT | CTG | ATG | ACT | CAG | AGG | | 21 | 371 |
| P90m15 | A | AGA | AAT | CTG | ATG | ACT | CAG | ATG | | 21 | 372 |
| P90m16 | GA | AGA | AAT | CTG | ATG | ACT | CAG | ATT | | 20 | 373 |
| P90m17 | GGA | AGA | AAT | CTG | ATG | ACT | CAG | | | 21 | 374 |
| P90m18 | A | AGA | AAT | CTG | ATG | ACT | CAG | | | 19 | 375 |
| P90m19 | | A | AAT | CTG | ATG | ACT | CAG | ATT | GG | 21 | 376 |
| P90m20 | | A | AAT | CTG | ATG | ACT | CAG | ATT | G | 20 | 377 |
| P90m21 | | A | AAT | CTG | ATG | ACT | CAG | CTT | G | 20 | 378 |

TABLE 3-continued

| | | | | | | | | | |
|---|---|---|---|---|---|---|---|---|---|
| P90m22 | A | AAT | CTG | ATG | ACT | CAG | CTT | | 19 | 379 |
| P90m23 | | AAT | CTG | ATG | ACT | CAG | CTT | G | 18 | 380 |
| P90w24 | A | AAT | CTG | TTG | ACT | CAG | CTT | G | 20 | 381 |
| P90w25 | A | AAT | CTG | TTG | ACT | CAG | CTT | | 19 | 382 |
| P90w26 | | AAT | CTG | TTG | ACT | CAG | CTT | G | 19 | 383 |
| P90w27 | | AAT | CTG | TTG | ACT | CA | | | 14 | 384 |
| P90w28 | | AAT | CTG | TTG | ACT | CAG | | | 15 | 385 |
| P90w29 | A | AAT | CTG | TTG | ACT | CA | | | 15 | 386 |
| P90w30 | A | AAT | CTG | TTG | ACT | CAG | | | 16 | 387 |
| P90m31 | | AAT | CTG | ATG | ACT | CA | | | 14 | 388 |
| P90m32 | | AAT | CTG | ATG | ACT | CAG | | | 15 | 389 |
| P90m33 | A | AAT | CTG | ATG | ACT | CA | | | 15 | 390 |
| P90m34 | A | AAT | CTG | ATG | ACT | CAG | | | 16 | 391 |
| P90w35 | GA | AAT | CTG | TTG | ACT | C | | | 15 | 392 |
| P90w36 | GA | ACT | CTG | TTG | ACT | C | | | 15 | 393 |
| P90w37 | | T | CTG | TTG | ACT | CAG | ATG | | 15 | 394 |
| P90w38 | GA | AAT | CTG | TTG | ACT | C | | | 15 | 395 |
| P90w39 | GA | ACT | CTG | TTG | ACT | C | | | 15 | 396 |
| P90w40 | A | AAT | CTG | TTG | ACT | CA | | | 15 | 397 |
| P90w41 | | AAT | CTG | TTG | ACT | CAG | | | 15 | 398 |
| P90w42 | | AAT | CTG | ATG | ACT | CAG | | | 15 | 399 |
| P90m43 | A | AAT | CTG | ATG | ACT | CA | | | 15 | 400 |
| P90w44 | | AT | CTG | TTG | ACT | CAG | AG | | 15 | 401 |
| P90w45 | | | CTG | TTG | ACT | CAG | ATT | | 15 | 402 |
| P90w46 | AGA | AAT | CTG | TTG | ACT | | | | 15 | 403 |
| P90m47 | | AT | CTG | ATG | ACT | CAG | AG | | 15 | 404 |
| P90m48 | | | CTG | ATG | ACT | CAG | ATT | | 15 | 405 |
| P90m49 | AGA | AAT | CTG | ATG | ACT | CA | | | 17 | 406 |
| P90w50 | | AAT | ATG | TTG | ACT | CAG | | | 15 | 407 |
| P90w51 | GA | AAT | ATG | TTG | ACT | CA | | | 16 | 408 |
| P90w52 | | AAT | TTG | TTG | ACT | CAG | | | 15 | 409 |
| P90w53 | GA | AAT | TTG | TTG | ACT | CA | | | 16 | 410 |
| P90w54 | | AAT | ATG | TTG | ACC | CAG | | | 15 | 411 |
| P90w55 | A | AAT | ATG | TTG | ACC | CA | | | 15 | 412 |
| P90m56 | | AAT | ATG | ATG | ACC | CAG | | | 15 | 413 |
| P90m57 | A | CAG | ATG | ATG | ACC | CA | | | 15 | 414 |
| P90w58 | | AAC | ATG | TTG | ACT | CAG | | | 15 | 415 |
| P90w59 | A | AAC | ATG | TTG | ACT | CAG | | | 15 | 416 |
| P90w60 | | | TG | TTG | ACT | CAG | CTT | | 14 | 417 |
| P90w61 | | | CTG | TTG | ACT | CAG | CTG | | 14 | 418 |
| P90m62 | | | CT | ATG | ACT | CAG | CTT | | 14 | 419 |
| P90w63 | | | CTG | ATG | ACT | CAG | C-G | | 14 | 420 |
| P90w64 | | | TG | ACT | ACA | CAG | CTT | | 14 | 421 |
| P90w65 | | | CTG | TTG | ACA | CAG | C-G | | 14 | 422 |
| P90w66 | | AAT | CTG | TTG | ACA | CAG | | | 15 | 423 |
| P90w67 | | AAC | CTG | TTG | ACT | CA | | | 13 | 424 |
| P90w68 | A | AAC | CTG | TTG | ACT | C | | | 13 | 425 |
| P90w69 | GA | AAC | CTG | TTG | ACT | | | | 13 | 426 |
| p90w70 | | | TG | TTG | ACT | CAG | ATT | G | 15 | 427 |
| p90w71 | | | TG | TTG | ACT | CAG | ATT | GGG | 16 | 428 |
| p90w72 | | | G | TTG | ACT | CAG | ATT | GGG | 15 | 429 |
| p90w73 | | | TG | TTG | ACA | CAG | CTT | G | 15 | 430 |
| p90w74 | | | CTG | TTG | ACA | CAG | CTT | | 15 | 431 |
| p90w75 | | | G | TTG | ACA | CAG | CTT | GGG | 15 | 432 |
| p90w76 | | | TG | TTG | ACT | CAG | CTT | G | 15 | 433 |
| p90w77 | | | G | TTG | ACT | CAG | ATG | | 15 | 434 |
| p90w78 | | | G | TTG | ACT | CAG | CTT | G | 14 | 435 |
| p90w79 | | | TG | TTG | ACC | CAG | ATT | G | 15 | 436 |
| p90w80 | | | G | TTG | ACC | CAG | ATT | G | 14 | 437 |
| p90w81 | | | G | TTG | ACC | CAG | ATT | GGG | 15 | 438 |
| p90m82 | | | TG | ATG | ACT | CAG | ATT | G | 15 | 439 |
| p90m83 | | | TG | ATG | ACT | CAG | ATT | GGG | 16 | 440 |
| p90m84 | | | G | ATG | ACT | CAG | ATT | GGG | 15 | 441 |
| p90m85 | | | G | ATG | ACT | CAG | ATT | GGT | 16 | 442 |
| p90m86 | | | CTG | ATG | ACT | CAG | CTT | | 15 | 443 |
| p90m87 | | | TG | ATG | ACT | CAG | CTT | G | 15 | 444 |
| P90w88 | A | AAT | CTG | TTG | ACT | CA | | | 15 | 445 |
| P90w89 | A | AAT | CTG | TTG | ACT | CA | | | 15 | 446 |
| p90w90 | A | AAT | CTG | TTG | ACT | CA | | | 15 | 447 |
| p90w100 | | AAT | CTG | ATG | ACT | CAG | | | 15 | 448 |
| p90w92 | A | AAT | CTG | ATG | ACT | CA | | | 16 | 449 |
| p90m93 | GA | AAT | CTG | ATG | ACT | C | | | 15 | 450 |
| p90m94 | | | CTG | ATG | ACT | CAG | ATG | | 15 | 451 |
| p90m95 | | AGA | AAT | ATG | ATG | | | | 15 | 452 |
| p90m96 | A | AGA | AAT | ATG | ATG | ACT | | | 16 | 453 |
| p90m97 | A | AGA | AAT | CTG | ATG | ACT | | | 16 | 454 |
| p90m98 | A | AGA | AAT | ATA | ATG | ACT | | | 16 | 455 |
| p90m99 | | A | AAT | ATA | ATG | ACT | CAG | | 16 | 456 |
| p90m100 | | | AAT | ATG | ATG | ACC | CAG | | 15 | 457 |

TABLE 3-continued

| | | | | | | | | | |
|---|---|---|---|---|---|---|---|---|---|
| p90m101 | | AAC | CTG | ATG | ACT | CAG | | 15 | 458 |
| p90m102 | AGA | AAT | TTG | ATG | ACT | C | | 16 | 459 |
| p90m103 | A | AAT | TTG | ATG | ACT | ATG | ACT | 16 | 460 |
| p90m104 | | AC | CTG | ATG | ACT | CAG | | 14 | 461 |
| p90m105 | | AAT | CTG | ATG | ACT | CAG | A | 16 | 462 |
| p90m106 | | AT | CTG | ATG | ACT | CAG | ATG | 16 | 463 |
| p90m107 | | AT | CTG | ATG | ACT | CAG | | 14 | 464 |
| p90m108 | | | CTG | ATG | ACT | CAG | ATT G | 16 | 465 |
| p90m109 | AGA | AAT | CTG | ATG | ACT | C | | 16 | 466 |
| p90m110 | AGA | AAT | CTG | ATG | ACT | | | 15 | 467 |
| p90m111 | GA | AGA | AAT | CTG | ATG | A | | 15 | 468 |
| p90m112 | GGA | AGA | AAT | CTG | ATG | A | | 16 | 469 |
| p90m113 | GA | AGA | AAT | CTG | ATG | AC | | 16 | 470 |
| p90m114 | | AGA | AAT | CTG | ATG | AC | | 14 | 471 |
| p90w115 | | AAT | CTG | TTA | ACT | CAG | | 15 | 472 |
| p90w116 | T | CTG | TTA | ACT | CAG | ATT | | 16 | 473 |
| p90w117 | AT | CTG | TTA | ACT | CAG | AG | | 15 | 474 |
| p90w118 | AGA | AAT | TTG | TTG | ACT | | | 16 | 475 |
| p90w119 | GA | AAT | TTG | TTG | ACT | C | | 15 | 476 |
| p90w120 | | AAT | TTG | TTG | ACT | CAG | | 15 | 477 |

TABLE 4

Polymorphic nucleotide sequences.

| 51 52 53 54 55 56 57 58 | codon position |
|---|---|
| gga ggt ttt atc aaa gta aga cag | consensus sequence |
| GGA GGT TTT ATC AAA GTC AGA CAA | SEQ ID NO 478 |
| GGA GGT TTC ATT AAG GTA AAA CAG | SEQ ID NO 479 |
| GGA GGT TTT ATT AAG GTA AGA CAG | SEQ ID NO 480 |
| GGA GGT TTT ATT AAA GTA AGA CAA | SEQ ID NO 481 |
| GGA GGC TTT ATC AAA GTA AGA CAA | SEQ ID NO 482 |
| GGA GGT TTT ATC AAA GTC AGA CAA | SEQ ID NO 483 |

| 78 79 80 81 82 83 84 85 | codon position |
|---|---|
| gga cct aca cct gtc aac ata att gg | consensus sequence |
| GGA CCT ACA CCG GTC AAC ATA ATT GG | SEQ ID NO 484 |
| GGA CCT ACA CCT GCC AAT ATA ATT GG | SEQ ID NO 485 |
| GGA CCT ACG CCC TTC AAC ATA ATT GG | SEQ ID NO 486 |
| GGA CCG ACA CCT GTC ACC ATA ATT GG | SEQ ID NO 487 |
| GGA CCT ATA CCT GTC AAC ATA ATT GG | SEQ ID NO 488 |

| 87 88 89 90 91 92 93 94 | codon position |
|---|---|
| a aga aat ctg ttg act cag att ggc | consensus sequence |
| A AAA AAT CTG ATG ACT CAG ATT GGC | SEQ ID NO 489 |
| A AGA ACT CTG TTG ACT CAG CTT GGA | SEQ ID NO 490 |
| A AGA AAT ATG ATG ACC CAG CTT GGC | SEQ ID NO 491 |
| A AGA AAT ATA ATG ACT CAG CTT GGA | SEQ ID NO 492 |
| A AGA AAT CTG CTG ACT CAG ATT GGG | SEQ ID NO 493 |
| A AGA AAT CTG TTG ACA CAG CTT GGC | SEQ ID NO 494 |
| A AGA AAT ATG TTG ACT CAG CTT GGT | SEQ ID NO 495 |
| A AGA AAT TTG TTG ACT CAG ATT GGG | SEQ ID NO 496 |
| A AGA AAT ATG TTG ACT CAG CTT GGT | SEQ ID NO 497 |
| A AGA AAT ATG TTG ACT CAG CTT GGA | SEQ ID NO 498 |
| A AGA AAT CTG TTG ACT CAG CTT GGA | SEQ ID NO 499 |
| A AGA AAC CTG TTG ACT CAA CTT GGT | SEQ ID NO 500 |

TABLE 5

| probes for codon p30 | Type B | non-B | probes for codon p48 | Type B | non-B | probes for codon p50 | Type B | non-B |
|---|---|---|---|---|---|---|---|---|
| w25 | 95.7 | 98 | w47 | 71.3 | 70 | w31 | 95.7 | 98 |
| w29 | 1.1 | 0 | w45 | 11.7 | 22 | w44 | 1.1 | 2 |
| w32 | 1.1 | 1 | w72 | 16 | 4 | w52 | 8.5 | 4 |
| w36 | 1.1 | 0 | m41 | 3.2 | 0 | m37 | 1.1 | 6 |
| m23 | 1.1 | 0 | neg. | 0 | 8 | neg. | 1.1 | 0 |
| neg. | 0 | 1 | | | | | | |

| probes for codon p54 | Type B | non-B | probes for codon p82/84 | Type B | non-B | probes for codon p90 | Type B | non-B |
|---|---|---|---|---|---|---|---|---|
| w3 | 71.3 | 48 | w91 | 81.9 | 70 | w27 | 50 | 2.5 |
| w34 | 81.9 | 62 | w60 | 2.1 | 12 | w37 | 66.1 | 17.5 |
| w14 | 3.2 | 18 | w111 | 1.1 | 0 | w39 | 7.1 | 0 |
| w19 | 6.4 | 0 | w89 | 1.1 | 10 | w50 | 12.5 | 65 |
| w22 | 4.3 | 8 | w42 | 4.3 | 2 | w52 | 7.1 | 2.5 |

TABLE 5-continued

| | | | | | | | | |
|---|---|---|---|---|---|---|---|---|
| w26 | 0 | 4 | m36 | 2.1 | 0 | w69 | 5.4 | 2.5 |
| w27 | 0 | 4 | m67 | 1.1 | 0 | w73 | 5.4 | 22.5 |
| m55 | 3.2 | 0 | m38 | 2.1 | 0 | w79 | 0 | 10 |
| m35 | 14.9 | 4 | m105 | 1.1 | 0 | m43 | 19.6 | 5 |
| m37 | 1.1 | 4 | m127 | 1.1 | 0 | m56 | 0 | 2.5 |
| neg. | 0 | 4 | m40 | 14.9 | 2 | neg. | 3.6 | 12.5 |
| | | | m63 | 3.2 | 2 | | | |
| | | | m101 | 2.1 | 12 | | | |
| | | | neg. | 3.2 | 8 | | | |

TABLE 6

| p30 | USA | France | U.K. | Brazil | Spain | Luxemb. | Belgium |
|---|---|---|---|---|---|---|---|
| w25 | 98.9 | 99.4 | 88.9 | 98.3 | 94.3 | 100.0 | 97.0 |
| w29 | 2.5 | 0.6 | 0.0 | 1.7 | 0.0 | 0.0 | 0.0 |
| w32 | 3.3 | 0.6 | 5.6 | 5.2 | 5.7 | 6.7 | 1.5 |
| w36 | 2.5 | 0.0 | 0.0 | 3.4 | 0.0 | 0.0 | 1.0 |
| m23 | 3.1 | 0.0 | 0.0 | 0.0 | 0.0 | 0.0 | 1.0 |
| neg. | 0.6 | 0.6 | 5.6 | 0.0 | 0.0 | 0.0 | 1.0 |
| p46/48 | USA | France | U.K. | Brazil | Spain | Luxemb. | Belgium |
| w47 | 94.2 | 80.5 | 83.3 | 89.7 | 97.1 | 73.3 | 82.9 |
| w45 | 8.6 | 15.6 | 0.0 | 1.7 | 5.7 | 6.7 | 11.1 |
| w72 | 4.2 | 0.0 | 16.7 | 0.0 | 2.9 | 13.3 | 5.0 |
| m41 | 0.0 | 0.0 | 0.0 | 10.3 | 0.0 | 13.3 | 1.0 |
| neg. | 2.8 | 4.5 | 0.0 | 0.0 | 0.0 | 0.0 | 2.5 |
| p50 | USA | France | U.K. | Brazil | Spain | Luxemb. | Belgium |
| w31 | 96.4 | 97.4 | 100.0 | 96.6 | 100.0 | 100.0 | 96.5 |
| w44 | 1.7 | 0.6 | 0.0 | 1.7 | 0.0 | 0.0 | 1.0 |
| w52 | 10.0 | 4.5 | 0.0 | 1.7 | 2.9 | 6.7 | 9.0 |
| m37 | 2.5 | 0.6 | 0.0 | 1.7 | 0.0 | 6.7 | 0.5 |
| neg. | 3.1 | 2.6 | 0.0 | 3.4 | 0.0 | 0.0 | 1.5 |
| p54 | USA | France | U.K. | Brazil | Spain | Luxemb. | Belgium |
| w34 | 96.9 | 82.5 | 97.2 | 87.9 | 100.0 | 53.3 | 89.4 |
| w3 | 84.7 | 77.9 | 94.4 | 69.0 | 82.9 | 46.7 | 76.9 |
| w14 | 3.3 | 5.8 | 0.0 | 3.4 | 11.4 | 0.0 | 6.5 |
| w19 | 9.2 | 2.6 | 0.0 | 1.7 | 2.9 | 6.7 | 5.5 |
| w22 | 2.8 | 10.4 | 0.0 | 0.0 | 5.7 | 0.0 | 2.5 |
| w26 | 0.0 | 1.3 | 0.0 | 0.0 | 0.0 | 0.0 | 0.0 |
| w27 | 0.0 | 1.9 | 0.0 | 0.0 | 0.0 | 0.0 | 0.5 |
| m55 | 0.0 | 0.0 | 0.0 | 0.0 | 0.0 | 13.3 | 0.5 |
| m35 | 1.1 | 0.0 | 2.8 | 6.9 | 0.0 | 46.7 | 3.0 |
| m37 | 0.0 | 0.0 | 0.0 | 0.0 | 0.0 | 13.3 | 0.0 |
| neg. | 0.6 | 1.3 | 0.0 | 1.7 | 0.0 | 0.0 | 2.0 |
| p82/84 | USA | France | U.K. | Brazil | Spain | Luxemb. | Belgium |
| w91 | 91.6 | 93.5 | 94.4 | 77.6 | 100.0 | 73.3 | 85.9 |
| w60 | 6.4 | 2.6 | 0.0 | 1.7 | 2.9 | 13.3 | 5.5 |
| w111 | 3.6 | 0.6 | 0.0 | 1.7 | 0.0 | 0.0 | 0.5 |
| w89 | 7.0 | 1.9 | 0.0 | 3.4 | 0.0 | 0.0 | 3.0 |
| w42 | 0.6 | 0.0 | 2.8 | 1.7 | 0.0 | 0.0 | 2.0 |
| m36 | 0.3 | 0.0 | 0.0 | 0.0 | 0.0 | 0.0 | 0.0 |
| m67 | 0.0 | 0.0 | 0.0 | 0.0 | 0.0 | 0.0 | 0.5 |
| m38 | 0.0 | 0.0 | 0.0 | 0.0 | 0.0 | 6.7 | 0.0 |
| m105 | 0.0 | 0.0 | 0.0 | 0.0 | 0.0 | 0.0 | 0.0 |
| m127 | 0.0 | 0.0 | 0.0 | 0.0 | 0.0 | 0.0 | 0.0 |
| m40 | 2.8 | 0.0 | 8.3 | 3.4 | 5.7 | 46.7 | 0.0 |
| m63 | 0.3 | 0.0 | 0.0 | 1.7 | 2.9 | 13.3 | 0.5 |
| m101 | 1.9 | 4.5 | 0.0 | 3.4 | 0.0 | 6.7 | 4.0 |
| neg. | 2.5 | 3.9 | 0.0 | 13.8 | 0.0 | 6.7 | 5.0 |

| p90 | USA | France | U.K. | Brazil | Spain | Belgium |
|---|---|---|---|---|---|---|
| w27 | 51.1 | 45.5 | 34.3 | 47.7 | 52.8 | 25.7 |
| w37 | 91.9 | 73.4 | 80.0 | 81.8 | 88.9 | 55.2 |
| w39 | 0.0 | 0.0 | 0.0 | 0.0 | 0.0 | 2.9 |
| w50 | 2.6 | 23.8 | 2.9 | 13.6 | 11.1 | 21.9 |
| w52 | 8.4 | 11.2 | 5.7 | 6.8 | 13.9 | 4.8 |
| w69 | 5.2 | 1.4 | 5.7 | 2.3 | 0.0 | 3.8 |
| w73 | 6.1 | 9.1 | 0.0 | 0.0 | 8.3 | 6.7 |
| w79 | 7.1 | 11.2 | 8.6 | 9.1 | 5.6 | 5.7 |
| m43 | 1.9 | 0.0 | 11.4 | 0.0 | 0.0 | 8.6 |
| m56 | 0.3 | 1.4 | 0.0 | 0.0 | 0.0 | 0.0 |
| neg. | 1.0 | 0.0 | 0.0 | 0.0 | 0.0 | 18.1 |

TABLE 7

| | | | | | | | | | | Tm | lengte | Seq ID |
|---|---|---|---|---|---|---|---|---|---|---|---|---|
| pc50w5 | AGG | GGG | AAT | TGG | AGG | TTT | TA | | | 20 | | 511 |
| | 26 | 27 | 28 | 29 | 30 | 31 | 32 | 33 | 34 | 35 | | |
| | ACA | GGA | GCA | GAT | GAT | ACA | GTA | TTA | GAA | GAA | | |
| pc30w25 | | | GCA | GAT | GAT | ACA | GT | | | | 40 | 14 | 31 |
| pc30w29 | | A | GCG | GAT | GAT | ACA | | | | | 36 | 13 | 35 |
| pc30w32 | | | GCA | GAT | GAC | ACA | GT | | | | 42 | 14 | 38 |
| pc30w36 | | | GCA | GAC | GAT | ACA | GG | | | | 40 | 14 | 42 |
| pc30m23 | | A | GCA | GAT | AAT | ACA | GT | | | | 40 | 15 | 29 |
| | 44 | 45 | 46 | 47 | 48 | 49 | 50 | 51 | 52 | | | |
| | CCA | AAA | ATG | ATA | GGG | GGA | ATT | GGA | GGT | | | |
| pc48w37 | | | ATG | ATA | GGG | GGA | ATT | | | | 15 | 512 |
| pc48w47 | | AAA | ATG | ATA | GGG | GGA | | | | 42 | 15 | 93 |
| pc48w73 | A | AGA | ATG | ATA | GGG | G | | | | | 14 | 513 |
| pc48w45 | | AAA | ATG | ATA | GGA | GGA | ATT | | | 42 | 18 | 91 |

TABLE 7-continued

| | | | | | | | | | | | |
|---|---|---|---|---|---|---|---|---|---|---|---|
| pc48w72 | A | AAA | ATA | ATA | GGG | GGA | | | 42 | 16 | 120 |
| pc48m41 | | | ATG | ATA | GTG | GGA | ATT | | 40 | 15 | 87 |

| | 48 | 49 | 50 | 51 | 52 | 53 | 54 | | | |
|---|---|---|---|---|---|---|---|---|---|---|
| | GGG | GGA | ATT | GGA | GGT | TTT | ATC | | | |
| pc50w31 | | GGA | ATT | GGA | GGT | TTT | | 42 | 15 | 151 |
| pc50w44 | | GGA | ATT | GGG | GGT | TT | | 42 | 14 | 164 |
| pc50w52 | | | GA | ATT | GGA | GGC | TTG | | 14 | 172 |
| pc50m37 | GGG | GGA | GTT | GGA | | | | 40 | 12 | 157 |

| | 51 | 52 | 53 | 54 | 55 | 56 | 57 | 58 | | | |
|---|---|---|---|---|---|---|---|---|---|---|---|
| | GGA | GGT | TTT | ATC | AAA | GTA | AGA | CAG | | | |
| pc54w34 | GA | GGT | TTT | ATC | AAA | GT | | | 42 | 16 | 212 |
| pc54w14 | | GGT | TTT | ATC | AAG | GTA | A | | 42 | 16 | 189 |
| pc54w19 | A | GGC | TTT | ATC | AAA | GTA | | | 42 | 16 | 194 |
| pc54w22 | GA | GGT | TTT | ATT | AAA | GTA | | | 42 | 17 | 197 |
| pc54w26 | A | GGT | TTC | ATT | AAG | GTA | | | 42 | 16 | 202 |
| pc54w27 | | GGT | TTT | ATT | AAG | GTA | A | | 40 | 16 | 204 |
| pc54m35 | | GGT | TTT | GTC | AAA | GTA | | | 40 | 15 | 213 |
| pc54m37 | | GGT | TTT | GTC | AGA | GTA | | | 42 | 15 | 215 |
| pc54m55 | A | GGT | TTT | GCC | AAA | GT | | | | 15 | 516 |

| | 78 | 79 | 80 | 81 | 82 | 83 | 84 | 85 | 86 | 87 | | | |
|---|---|---|---|---|---|---|---|---|---|---|---|---|---|
| | GGA | CCT | ACA | CCT | GTC | AAC | ATA | ATT | GGA | AGA | | | |
| pc82w91 | | ACA | CCT | GTC | AAC | ATA | A | | | | 44 | 16 | 318 |
| pc82w60 | | CA | CCT | GTC | AAT | ATA | ATG | | | | 42 | 17 | 287 |
| pc82w111 | | A | CCG | GTC | AAC | ATA | ATT | | | | 44 | 16 | 338 |
| pc82w89 | | ACA | CCT | GTT | AAC | ATA | AG | | | | 42 | 17 | 316 |
| pc82m101 | | ACA | CCT | ATC | AAC | ATA | AT | | | | | 17 | 517 |
| pc82w42 | | CA | CCT | GTC | AAC | GTA | | | | | 42 | 14 | 269 |
| pc82m38 | | ACA | CCT | TTC | AAC | ATA | | | | | 40 | 15 | 265 |
| pc82m105 | | ACG | CCC | TTC | AAC | ATA | | | | | 44 | 15 | 332 |
| pc82m127 | | CA | CCT | TTC | AAC | GTA | ATG | | | | 44 | 17 | 354 |
| pc82m40 | | ACA | CCT | GCC | AAC | ATA | | | | | 44 | 15 | 267 |
| pc82m63 | | CA | CCT | GCC | AAT | ATA | AG | | | | 42 | 16 | 290 |
| pc82m36 | | ACA | CCT | ACC | AAC | ATA | | | | | | 15 | 518 |
| pc82m67 | | ACA | CCT | ACC | AAC | GT | | | | | | 14 | 519 |

| | 86 | 87 | 88 | 89 | 90 | 91 | 92 | 93 | 94 | | | |
|---|---|---|---|---|---|---|---|---|---|---|---|---|
| | GGA | AGA | AAT | CTG | TTG | ACT | CAG | ATT | GGT | | | |
| pc90w27 | | | ATT | CTG | TTG | ACT | CA | | | 38 | 14 | 384 |
| pc90w37 | | T | | CTG | TTG | ACT | CAG | AT | | | 15 | 514 |
| pc90w39 | | GA | GTC | AAC | AGA | GTT | C | | | | 15 | 515 |
| pc90w50 | | | AAT | ATG | TTG | ACT | CAG | | | 40 | 15 | 407 |
| pc90w52 | | | AAT | TTG | TTG | ACT | CAG | | | 40 | 15 | 409 |
| pc90w69 | | GA | AAC | CTG | TTG | ACT | | | | 40 | 14 | 426 |
| pc90w73 | | | | TG | TTG | ACA | CAG | CTT | G | 44 | 15 | 430 |
| pc90w79 | | | | TG | TTG | ACC | CAG | ATT | G | 44 | 15 | 436 |
| pc90m138 | | GTC | ATC | AGA | TTT | CT | | | | | 14 | 510 |
| pc90m56 | | | AAT | ATG | ATG | ACC | CAG | | | 42 | 15 | 413 |

What is claimed is:

1. Method for determining the susceptibility to antiviral drugs of HIV viruses in a biological sample comprising polynucleic acids, with said method comprising:

a) releasing, isolating or concentrating the polynucleic, acids present in the sample;

b) amplifying part of a protease gene of HIV comprising codons 82 and 84 from the polynucleic acids with at least one suitable primer pair;

c) hybridizing the polynucleic acids of step a) or b) with probes having the sequence of SEQ ID NO:267 and SEQ ID NO:354, or probes having sequence complementary to SEQ ID NO:267 and SEQ ID NO:354;

wherein said probes are immobilized on a solid support; and d) inferring from the result of step c) whether or not a mutation giving rise to drug resistance is present in said polynucleic acids.

2. A method for determining the susceptibility to antiviral drugs of HIV viruses in a biological sample comprising polynucleic acids, with said method comprising:

a) releasing, isolating or concentrating the polynucleic acids present in the sample;

b) optionally, amplifying part of a protease gene of HIV comprising codons 82 and 84 with at least one suitable primer pair;

c) hybridizing the nucleic acids of step a) or b) with probes having the sequence of SEQ ID NO:267 and SEQ ID NO:354, or probes having sequences complementary to SEQ ID NO:267 and SEQ ID NO:354; wherein said probes are immobilized on a solid support; and d) inferring from the result of step c) whether or not a mutation giving rise to drug resistance is present in said polynucleic acids.

3. Method according to claim 2 further characterized in that said primer pair is chosen from the following primers: SEQ ID NO: 3, SEQ ID NO: 503, SEQ ID NO: 504, SEQ ID NO: 4, SEQ ID NO: 506, SEQ ID NO: 507, SEQ ID NO: 508 and SEQ ID NO: 509.

4. The method of claim 2 wherein step b) comprises amplifying a fragment of the protease gene with at least one 5'-primer specifically hybridizing to a target sequence located at nucleotide position 210 to 260 of the coding portion of the protease gene, in combination with at least one suitable 3'-primer.

5. The method of claim 2 wherein step b) comprises amplifying a fragment of the protease gene with at least one 3'-primer specifically hybridizing to a target sequence located at nucleotide position 253 (codon 85) to position 300 of the coding portion of the protease gene, in combination with at least one suitable 5'-primer.

6. Method according to claim 4, further characterized in that the 5'-primer is SEQ ID NO: 5 and the 3'-primer is one primer or a combination of primers chosen from the following primers: SEQ ID NO: 4, SEQ ID NO: 506, SEQ ID NO: 507, SEQ ID NO: 508 and SEQ ID NO: 509.

7. Method according to claim 5, further characterized in that the 5'-primer is one primer or a combination of primer chosen from the following primers: SEQ ID NO: 3, SEQ ID NO: 503, SEQ ID NO: 504 and the 3'-primer is SEQ ID NO: 6.

8. The method according to claim 1 wherein said primer pair is chosen from the following primers: SEQ ID NO: 3, SEQ ID NO: 503, SEQ ID NO: 504, SEQ ID NO: 4, SEQ ID NO: 506, SEQ ID NO: 507, SEQ ID NO: 508 and SEQ ID NO: 509.

9. The method of claim 1 wherein step b) comprises amplifying a fragment of the protease gene with at least one 5'-primer specifically hybridizing to a target sequence located at nucleotide position 210 to 260 of the coding portion of the protease gene, in combination with at least one suitable 3'-primer.

10. The method of claim 1 wherein step b) comprises amplifying a fragment of the protease gene with at least one 3'-primer specifically hybridizing to a target sequence located at nucleotide position 253 (codon 85) to position 300, in combination with at least one suitable 5'-primer.

11. The method of claim 1 wherein the target sequences for codon 82/84 are provided by SEQ ID NO: 228–357.

* * * * *

UNITED STATES PATENT AND TRADEMARK OFFICE
CERTIFICATE OF CORRECTION

PATENT NO.    : 6,803,187 B1
DATED         : October 12, 2004
INVENTOR(S)   : Lieven Stuyver It is certified that error appears in the above-identified patent and that said Letters Patent is hereby corrected as shown below:

Column 175,
Line 6, delete the comma after "polynucleic".

Column 177,
Line 14, delete "nucleic" and insert -- polynucleic -- therefor.

Column 178,
Line 11, delete "primer" and insert -- primers -- therefor.

Signed and Sealed this

Fifteenth Day of February, 2005

JON W. DUDAS
*Director of the United States Patent and Trademark Office*

SEQUENCE LISTING

<160> NUMBER OF SEQ ID NOS: 529

<210> SEQ ID NO 1
<211> LENGTH: 21
<212> TYPE: DNA
<213> ORGANISM: Aids-associated retrovirus

<400> SEQUENCE: 1
cagagccaac agccccacca g                                        21

<210> SEQ ID NO 2
<211> LENGTH: 27
<212> TYPE: DNA
<213> ORGANISM: Aids-associated retrovirus

```
<400> SEQUENCE: 2
atcaggatgg agttcataac ccatcca                                              27

<210> SEQ ID NO 3
<211> LENGTH: 23
<212> TYPE: DNA
<213> ORGANISM: Aids-associated retrovirus

<400> SEQUENCE: 3
cctcaratca ctctttggca acg                                                  23

<210> SEQ ID NO 4
<211> LENGTH: 25
<212> TYPE: DNA
<213> ORGANISM: Aids-associated retrovirus

<400> SEQUENCE: 4
taatcrggat aactytgaca tggtc                                                25

<210> SEQ ID NO 5
<211> LENGTH: 20
<212> TYPE: DNA
<213> ORGANISM: Aids-associated retrovirus

<400> SEQUENCE: 5
cctgtcaaca taattggaag                                                      20

<210> SEQ ID NO 6
<211> LENGTH: 21
<212> TYPE: DNA
<213> ORGANISM: Aids-associated retrovirus

<400> SEQUENCE: 6
agtcaacaga tttcttccaa t                                                    21

<210> SEQ ID NO 7
<211> LENGTH: 18
<212> TYPE: DNA
<213> ORGANISM: Aids-associated retrovirus

<400> SEQUENCE: 7
agcagatgat acagtatt                                                        18

<210> SEQ ID NO 8
<211> LENGTH: 19
<212> TYPE: DNA
<213> ORGANISM: Aids-associated retrovirus

<400> SEQUENCE: 8
gagcagatga tacagtatt                                                       19

<210> SEQ ID NO 9
<211> LENGTH: 19
<212> TYPE: DNA
<213> ORGANISM: Aids-associated retrovirus

<400> SEQUENCE: 9
agcagatgat acagtatta                                                       19

<210> SEQ ID NO 10
<211> LENGTH: 20
<212> TYPE: DNA
```

```
<213> ORGANISM: Aids-associated retrovirus

<400> SEQUENCE: 10
ggagcagatg atacagtatt                                              20

<210> SEQ ID NO 11
<211> LENGTH: 21
<212> TYPE: DNA
<213> ORGANISM: Aids-associated retrovirus

<400> SEQUENCE: 11
ggagcagatg atacagtatt a                                            21

<210> SEQ ID NO 12
<211> LENGTH: 18
<212> TYPE: DNA
<213> ORGANISM: Aids-associated retrovirus

<400> SEQUENCE: 12
acaggagcag atgataca                                                18

<210> SEQ ID NO 13
<211> LENGTH: 19
<212> TYPE: DNA
<213> ORGANISM: Aids-associated retrovirus

<400> SEQUENCE: 13
caggagcaga tgatacagt                                               19

<210> SEQ ID NO 14
<211> LENGTH: 21
<212> TYPE: DNA
<213> ORGANISM: Aids-associated retrovirus

<400> SEQUENCE: 14
aggagcagat gatacagtat g                                            21

<210> SEQ ID NO 15
<211> LENGTH: 20
<212> TYPE: DNA
<213> ORGANISM: Aids-associated retrovirus

<400> SEQUENCE: 15
ggagcagatg atacagtatg                                              20

<210> SEQ ID NO 16
<211> LENGTH: 20
<212> TYPE: DNA
<213> ORGANISM: Aids-associated retrovirus

<400> SEQUENCE: 16
acaggagcag atgatacagg                                              20

<210> SEQ ID NO 17
<211> LENGTH: 18
<212> TYPE: DNA
<213> ORGANISM: Aids-associated retrovirus

<400> SEQUENCE: 17
agcagataat acagtatt                                                18

<210> SEQ ID NO 18
<211> LENGTH: 19
```

```
<212> TYPE: DNA
<213> ORGANISM: Aids-associated retrovirus

<400> SEQUENCE: 18
gagcagataa tacagtatt                                                 19

<210> SEQ ID NO 19
<211> LENGTH: 19
<212> TYPE: DNA
<213> ORGANISM: Aids-associated retrovirus

<400> SEQUENCE: 19
agcagataat acagtatta                                                 19

<210> SEQ ID NO 20
<211> LENGTH: 20
<212> TYPE: DNA
<213> ORGANISM: Aids-associated retrovirus

<400> SEQUENCE: 20
ggagcagata atacagtatt                                                20

<210> SEQ ID NO 21
<211> LENGTH: 21
<212> TYPE: DNA
<213> ORGANISM: Aids-associated retrovirus

<400> SEQUENCE: 21
ggagcagata atacagtatt a                                              21

<210> SEQ ID NO 22
<211> LENGTH: 18
<212> TYPE: DNA
<213> ORGANISM: Aids-associated retrovirus

<400> SEQUENCE: 22
acaggagcag ataataca                                                  18

<210> SEQ ID NO 23
<211> LENGTH: 19
<212> TYPE: DNA
<213> ORGANISM: Aids-associated retrovirus

<400> SEQUENCE: 23
caggagcaga taatacagt                                                 19

<210> SEQ ID NO 24
<211> LENGTH: 21
<212> TYPE: DNA
<213> ORGANISM: Aids-associated retrovirus

<400> SEQUENCE: 24
aggagcagat aatacagtat g                                              21

<210> SEQ ID NO 25
<211> LENGTH: 20
<212> TYPE: DNA
<213> ORGANISM: Aids-associated retrovirus

<400> SEQUENCE: 25
ggagcagata atacagtatg                                                20

<210> SEQ ID NO 26
```

```
<211> LENGTH: 20
<212> TYPE: DNA
<213> ORGANISM: Aids-associated retrovirus

<400> SEQUENCE: 26
acaggagcag ataatacagg                                                20

<210> SEQ ID NO 27
<211> LENGTH: 15
<212> TYPE: DNA
<213> ORGANISM: Aids-associated retrovirus

<400> SEQUENCE: 27
agcagatgat acagt                                                     15

<210> SEQ ID NO 28
<211> LENGTH: 17
<212> TYPE: DNA
<213> ORGANISM: Aids-associated retrovirus

<400> SEQUENCE: 28
agcagatgat acagtag                                                   17

<210> SEQ ID NO 29
<211> LENGTH: 15
<212> TYPE: DNA
<213> ORGANISM: Aids-associated retrovirus

<400> SEQUENCE: 29
agcagataat acagt                                                     15

<210> SEQ ID NO 30
<211> LENGTH: 17
<212> TYPE: DNA
<213> ORGANISM: Aids-associated retrovirus

<400> SEQUENCE: 30
agcagataat acagtag                                                   17

<210> SEQ ID NO 31
<211> LENGTH: 14
<212> TYPE: DNA
<213> ORGANISM: Aids-associated retrovirus

<400> SEQUENCE: 31
gcagatgata cagt                                                      14

<210> SEQ ID NO 32
<211> LENGTH: 15
<212> TYPE: DNA
<213> ORGANISM: Aids-associated retrovirus

<400> SEQUENCE: 32
agcagatgat acagg                                                     15

<210> SEQ ID NO 33
<211> LENGTH: 13
<212> TYPE: DNA
<213> ORGANISM: Aids-associated retrovirus

<400> SEQUENCE: 33
cagatgatac agt                                                       13
```

```
<210> SEQ ID NO 34
<211> LENGTH: 14
<212> TYPE: DNA
<213> ORGANISM: Aids-associated retrovirus

<400> SEQUENCE: 34
gagcggatga taca                                                      14

<210> SEQ ID NO 35
<211> LENGTH: 13
<212> TYPE: DNA
<213> ORGANISM: Aids-associated retrovirus

<400> SEQUENCE: 35
agcggatgat aca                                                       13

<210> SEQ ID NO 36
<211> LENGTH: 15
<212> TYPE: DNA
<213> ORGANISM: Aids-associated retrovirus

<400> SEQUENCE: 36
gcagataata cagta                                                     15

<210> SEQ ID NO 37
<211> LENGTH: 14
<212> TYPE: DNA
<213> ORGANISM: Aids-associated retrovirus

<400> SEQUENCE: 37
gcagataata cagt                                                      14

<210> SEQ ID NO 38
<211> LENGTH: 14
<212> TYPE: DNA
<213> ORGANISM: Aids-associated retrovirus

<400> SEQUENCE: 38
gcagatgaca cagt                                                      14

<210> SEQ ID NO 39
<211> LENGTH: 15
<212> TYPE: DNA
<213> ORGANISM: Aids-associated retrovirus

<400> SEQUENCE: 39
cagatgacac agtag                                                     15

<210> SEQ ID NO 40
<211> LENGTH: 16
<212> TYPE: DNA
<213> ORGANISM: Aids-associated retrovirus

<400> SEQUENCE: 40
cagatgatac aatatt                                                    16

<210> SEQ ID NO 41
<211> LENGTH: 17
<212> TYPE: DNA
<213> ORGANISM: Aids-associated retrovirus

<400> SEQUENCE: 41
gcagatgata caatatg                                                   17
```

```
<210> SEQ ID NO 42
<211> LENGTH: 14
<212> TYPE: DNA
<213> ORGANISM: Aids-associated retrovirus

<400> SEQUENCE: 42
gcagacgata cagg                                                         14

<210> SEQ ID NO 43
<211> LENGTH: 14
<212> TYPE: DNA
<213> ORGANISM: Aids-associated retrovirus

<400> SEQUENCE: 43
gcagacgata cagt                                                         14

<210> SEQ ID NO 44
<211> LENGTH: 15
<212> TYPE: DNA
<213> ORGANISM: Aids-associated retrovirus

<400> SEQUENCE: 44
agatgataca atatt                                                        15

<210> SEQ ID NO 45
<211> LENGTH: 16
<212> TYPE: DNA
<213> ORGANISM: Aids-associated retrovirus

<400> SEQUENCE: 45
agatgataca atatta                                                       16

<210> SEQ ID NO 46
<211> LENGTH: 15
<212> TYPE: DNA
<213> ORGANISM: Aids-associated retrovirus

<400> SEQUENCE: 46
gcagatgata caata                                                        15

<210> SEQ ID NO 47
<211> LENGTH: 20
<212> TYPE: DNA
<213> ORGANISM: Aids-associated retrovirus

<400> SEQUENCE: 47 gtaggggaa ttggaggtgg                                                    20

<210> SEQ ID NO 48
<211> LENGTH: 20
<212> TYPE: DNA
<213> ORGANISM: Aids-associated retrovirus

<400> SEQUENCE: 48 gtaggggaa ttggaggttg                                                    20

<210> SEQ ID NO 49
<211> LENGTH: 21
<212> TYPE: DNA
<213> ORGANISM: Aids-associated retrovirus

<400> SEQUENCE: 49 gtaggggaa ttggaggttt g                                                  21
```

```
<210> SEQ ID NO 50
<211> LENGTH: 21
<212> TYPE: DNA
<213> ORGANISM: Aids-associated retrovirus

<400> SEQUENCE: 50
gtagggggaa ttggaggttt t                                       21

<210> SEQ ID NO 51
<211> LENGTH: 22
<212> TYPE: DNA
<213> ORGANISM: Aids-associated retrovirus

<400> SEQUENCE: 51
ggtaggggga attggaggtt tg                                      22

<210> SEQ ID NO 52
<211> LENGTH: 18
<212> TYPE: DNA
<213> ORGANISM: Aids-associated retrovirus

<400> SEQUENCE: 52
atggtagggg gaattgga                                           18

<210> SEQ ID NO 53
<211> LENGTH: 19
<212> TYPE: DNA
<213> ORGANISM: Aids-associated retrovirus

<400> SEQUENCE: 53
atggtagggg gaattggag                                          19

<210> SEQ ID NO 54
<211> LENGTH: 19
<212> TYPE: DNA
<213> ORGANISM: Aids-associated retrovirus

<400> SEQUENCE: 54
aatggtaggg ggaattgga                                          19

<210> SEQ ID NO 55
<211> LENGTH: 20
<212> TYPE: DNA
<213> ORGANISM: Aids-associated retrovirus

<400> SEQUENCE: 55
aatggtaggg ggaattggag                                         20

<210> SEQ ID NO 56
<211> LENGTH: 24
<212> TYPE: DNA
<213> ORGANISM: Aids-associated retrovirus

<400> SEQUENCE: 56
aatggtaggg ggaattggag gggg                                    24

<210> SEQ ID NO 57
<211> LENGTH: 18
<212> TYPE: DNA
<213> ORGANISM: Aids-associated retrovirus

<400> SEQUENCE: 57
```

-continued

| | |
|---|---|
| ataataggg gaattgga | 18 |

<210> SEQ ID NO 58
<211> LENGTH: 18
<212> TYPE: DNA
<213> ORGANISM: Aids-associated retrovirus

<400> SEQUENCE: 58

| | |
|---|---|
| atgatagggg gaattgga | 18 |

<210> SEQ ID NO 59
<211> LENGTH: 19
<212> TYPE: DNA
<213> ORGANISM: Aids-associated retrovirus

<400> SEQUENCE: 59

| | |
|---|---|
| aataataggg ggaattgga | 19 |

<210> SEQ ID NO 60
<211> LENGTH: 19
<212> TYPE: DNA
<213> ORGANISM: Aids-associated retrovirus

<400> SEQUENCE: 60

| | |
|---|---|
| aatgataggg ggaattgga | 19 |

<210> SEQ ID NO 61
<211> LENGTH: 20
<212> TYPE: DNA
<213> ORGANISM: Aids-associated retrovirus

<400> SEQUENCE: 61

| | |
|---|---|
| ataggggggaa ttggaggtgg | 20 |

<210> SEQ ID NO 62
<211> LENGTH: 20
<212> TYPE: DNA
<213> ORGANISM: Aids-associated retrovirus

<400> SEQUENCE: 62

| | |
|---|---|
| ataggggaa ttggaggttg | 20 |

<210> SEQ ID NO 63
<211> LENGTH: 21
<212> TYPE: DNA
<213> ORGANISM: Aids-associated retrovirus

<400> SEQUENCE: 63

| | |
|---|---|
| ataggggaa ttggaggttt g | 21 |

<210> SEQ ID NO 64
<211> LENGTH: 21
<212> TYPE: DNA
<213> ORGANISM: Aids-associated retrovirus

<400> SEQUENCE: 64

| | |
|---|---|
| ataggggaa ttggaggttt t | 21 |

<210> SEQ ID NO 65
<211> LENGTH: 20
<212> TYPE: DNA
<213> ORGANISM: Aids-associated retrovirus

<400> SEQUENCE: 65

```
gtagtgggaa ttggaggtgg                                              20

<210> SEQ ID NO 66
<211> LENGTH: 20
<212> TYPE: DNA
<213> ORGANISM: Aids-associated retrovirus

<400> SEQUENCE: 66
gtagtgggaa ttggaggttg                                              20

<210> SEQ ID NO 67
<211> LENGTH: 21
<212> TYPE: DNA
<213> ORGANISM: Aids-associated retrovirus

<400> SEQUENCE: 67
gtagtgggaa ttggaggttt g                                            21

<210> SEQ ID NO 68
<211> LENGTH: 21
<212> TYPE: DNA
<213> ORGANISM: Aids-associated retrovirus

<400> SEQUENCE: 68
gtagtgggaa ttggaggttt t                                            21

<210> SEQ ID NO 69
<211> LENGTH: 22
<212> TYPE: DNA
<213> ORGANISM: Aids-associated retrovirus

<400> SEQUENCE: 69
ggtagtggga attggaggtt tg                                           22

<210> SEQ ID NO 70
<211> LENGTH: 18
<212> TYPE: DNA
<213> ORGANISM: Aids-associated retrovirus

<400> SEQUENCE: 70
atggtagtgg gaattgga                                                18

<210> SEQ ID NO 71
<211> LENGTH: 19
<212> TYPE: DNA
<213> ORGANISM: Aids-associated retrovirus

<400> SEQUENCE: 71
atggtagtgg gaattggag                                               19

<210> SEQ ID NO 72
<211> LENGTH: 19
<212> TYPE: DNA
<213> ORGANISM: Aids-associated retrovirus

<400> SEQUENCE: 72
aatggtagtg ggaattgga                                               19

<210> SEQ ID NO 73
<211> LENGTH: 20
<212> TYPE: DNA
<213> ORGANISM: Aids-associated retrovirus
```

```
<400> SEQUENCE: 73
aatggtagtg ggaattggag                                              20

<210> SEQ ID NO 74
<211> LENGTH: 24
<212> TYPE: DNA
<213> ORGANISM: Aids-associated retrovirus

<400> SEQUENCE: 74
aatggtagtg ggaattggag gggg                                         24

<210> SEQ ID NO 75
<211> LENGTH: 20
<212> TYPE: DNA
<213> ORGANISM: Aids-associated retrovirus

<400> SEQUENCE: 75
atagtgggaa ttggaggtgg                                              20

<210> SEQ ID NO 76
<211> LENGTH: 20
<212> TYPE: DNA
<213> ORGANISM: Aids-associated retrovirus

<400> SEQUENCE: 76
atagtgggaa ttggaggttg                                              20

<210> SEQ ID NO 77
<211> LENGTH: 18
<212> TYPE: DNA
<213> ORGANISM: Aids-associated retrovirus

<400> SEQUENCE: 77
atgatagtgg gaattgga                                                18

<210> SEQ ID NO 78
<211> LENGTH: 19
<212> TYPE: DNA
<213> ORGANISM: Aids-associated retrovirus

<400> SEQUENCE: 78
atgatagtgg gaattggag                                               19

<210> SEQ ID NO 79
<211> LENGTH: 19
<212> TYPE: DNA
<213> ORGANISM: Aids-associated retrovirus

<400> SEQUENCE: 79
aatgatagtg ggaattgga                                               19

<210> SEQ ID NO 80
<211> LENGTH: 14
<212> TYPE: DNA
<213> ORGANISM: Aids-associated retrovirus

<400> SEQUENCE: 80
gataggggga attg                                                    14

<210> SEQ ID NO 81
<211> LENGTH: 15
<212> TYPE: DNA
<213> ORGANISM: Aids-associated retrovirus
```

```
<400> SEQUENCE: 81
tgataggggg aattg                                                    15

<210> SEQ ID NO 82
<211> LENGTH: 16
<212> TYPE: DNA
<213> ORGANISM: Aids-associated retrovirus

<400> SEQUENCE: 82
tgataggggg aattgg                                                   16

<210> SEQ ID NO 83
<211> LENGTH: 15
<212> TYPE: DNA
<213> ORGANISM: Aids-associated retrovirus

<400> SEQUENCE: 83 atgataggggg gaatt                                                   15

<210> SEQ ID NO 84
<211> LENGTH: 14
<212> TYPE: DNA
<213> ORGANISM: Aids-associated retrovirus

<400> SEQUENCE: 84
gatagtggga attg                                                     14

<210> SEQ ID NO 85
<211> LENGTH: 15
<212> TYPE: DNA
<213> ORGANISM: Aids-associated retrovirus

<400> SEQUENCE: 85
tgatagtggg aattg                                                    15

<210> SEQ ID NO 86
<211> LENGTH: 16
<212> TYPE: DNA
<213> ORGANISM: Aids-associated retrovirus

<400> SEQUENCE: 86
tgatagtggg aattgg                                                   16

<210> SEQ ID NO 87
<211> LENGTH: 15
<212> TYPE: DNA
<213> ORGANISM: Aids-associated retrovirus

<400> SEQUENCE: 87
atgatagtgg gaatt                                                    15

<210> SEQ ID NO 88
<211> LENGTH: 15
<212> TYPE: DNA
<213> ORGANISM: Aids-associated retrovirus

<400> SEQUENCE: 88
ataatagggg gaatt                                                    15

<210> SEQ ID NO 89
<211> LENGTH: 14
<212> TYPE: DNA
```

-continued

<213> ORGANISM: Aids-associated retrovirus

<400> SEQUENCE: 89 tgatagggg agtt                                                  14

<210> SEQ ID NO 90
<211> LENGTH: 14
<212> TYPE: DNA
<213> ORGANISM: Aids-associated retrovirus

<400> SEQUENCE: 90
gataggggga gttg                                                 14

<210> SEQ ID NO 91
<211> LENGTH: 18
<212> TYPE: DNA
<213> ORGANISM: Aids-associated retrovirus

<400> SEQUENCE: 91
aaaatgatag gaggaatt                                             18

<210> SEQ ID NO 92
<211> LENGTH: 15
<212> TYPE: DNA
<213> ORGANISM: Aids-associated retrovirus

<400> SEQUENCE: 92
atgatagggg gaatt                                                15

<210> SEQ ID NO 93
<211> LENGTH: 15
<212> TYPE: DNA
<213> ORGANISM: Aids-associated retrovirus

<400> SEQUENCE: 93
aaaatgatag gggga                                                15

<210> SEQ ID NO 94
<211> LENGTH: 15
<212> TYPE: DNA
<213> ORGANISM: Aids-associated retrovirus

<400> SEQUENCE: 94
aaaaatgata ggggg                                                15

<210> SEQ ID NO 95
<211> LENGTH: 16
<212> TYPE: DNA
<213> ORGANISM: Aids-associated retrovirus

<400> SEQUENCE: 95
aaatgatagg gggaag                                               16

<210> SEQ ID NO 96
<211> LENGTH: 17
<212> TYPE: DNA
<213> ORGANISM: Aids-associated retrovirus

<400> SEQUENCE: 96
aaaataatag ggggaag                                              17

<210> SEQ ID NO 97
<211> LENGTH: 11

```
<212> TYPE: DNA
<213> ORGANISM: Aids-associated retrovirus

<400> SEQUENCE: 97
aaaataaaaa t                                                            11

<210> SEQ ID NO 98
<211> LENGTH: 17
<212> TYPE: DNA
<213> ORGANISM: Aids-associated retrovirus

<400> SEQUENCE: 98
aaaatgatag tgggaag                                                      17

<210> SEQ ID NO 99
<211> LENGTH: 14
<212> TYPE: DNA
<213> ORGANISM: Aids-associated retrovirus

<400> SEQUENCE: 99
aaattgatag gggg                                                         14

<210> SEQ ID NO 100
<211> LENGTH: 15
<212> TYPE: DNA
<213> ORGANISM: Aids-associated retrovirus

<400> SEQUENCE: 100
aaaatgatag tggga                                                        15

<210> SEQ ID NO 101
<211> LENGTH: 15
<212> TYPE: DNA
<213> ORGANISM: Aids-associated retrovirus

<400> SEQUENCE: 101
aaattgatag gggga                                                        15

<210> SEQ ID NO 102
<211> LENGTH: 12
<212> TYPE: DNA
<213> ORGANISM: Aids-associated retrovirus

<400> SEQUENCE: 102
caaaattgat ag                                                           12

<210> SEQ ID NO 103
<211> LENGTH: 15
<212> TYPE: DNA
<213> ORGANISM: Aids-associated retrovirus

<400> SEQUENCE: 103
atggtagggg gaatt                                                        15

<210> SEQ ID NO 104
<211> LENGTH: 14
<212> TYPE: DNA
<213> ORGANISM: Aids-associated retrovirus

<400> SEQUENCE: 104
aaatggtagg ggga                                                         14

<210> SEQ ID NO 105
```

-continued

```
<211> LENGTH: 14
<212> TYPE: DNA
<213> ORGANISM: Aids-associated retrovirus

<400> SEQUENCE: 105
aaaaatggta gggg                                                          14

<210> SEQ ID NO 106
<211> LENGTH: 15
<212> TYPE: DNA
<213> ORGANISM: Aids-associated retrovirus

<400> SEQUENCE: 106
atgatagggg aaatt                                                         15

<210> SEQ ID NO 107
<211> LENGTH: 15
<212> TYPE: DNA
<213> ORGANISM: Aids-associated retrovirus

<400> SEQUENCE: 107 atagggaaa ttgga                                                          15

<210> SEQ ID NO 108
<211> LENGTH: 16
<212> TYPE: DNA
<213> ORGANISM: Aids-associated retrovirus

<400> SEQUENCE: 108 atagggaaa ttggag                                                         16

<210> SEQ ID NO 109
<211> LENGTH: 15
<212> TYPE: DNA
<213> ORGANISM: Aids-associated retrovirus

<400> SEQUENCE: 109
atgatagggg ggatt                                                         15

<210> SEQ ID NO 110
<211> LENGTH: 14
<212> TYPE: DNA
<213> ORGANISM: Aids-associated retrovirus

<400> SEQUENCE: 110 ataggggga ttgg                                                           14

<210> SEQ ID NO 111
<211> LENGTH: 13
<212> TYPE: DNA
<213> ORGANISM: Aids-associated retrovirus

<400> SEQUENCE: 111
aggggggatt gga                                                           13

<210> SEQ ID NO 112
<211> LENGTH: 15
<212> TYPE: DNA
<213> ORGANISM: Aids-associated retrovirus

<400> SEQUENCE: 112
aaaataatag tggga                                                         15
```

```
<210> SEQ ID NO 113
<211> LENGTH: 16
<212> TYPE: DNA
<213> ORGANISM: Aids-associated retrovirus

<400> SEQUENCE: 113
aaaaataata gtggga                                                    16

<210> SEQ ID NO 114
<211> LENGTH: 16
<212> TYPE: DNA
<213> ORGANISM: Aids-associated retrovirus

<400> SEQUENCE: 114
caaaaataat agtggg                                                    16

<210> SEQ ID NO 115
<211> LENGTH: 15
<212> TYPE: DNA
<213> ORGANISM: Aids-associated retrovirus

<400> SEQUENCE: 115
aaattgatag tggga                                                     15

<210> SEQ ID NO 116
<211> LENGTH: 16
<212> TYPE: DNA
<213> ORGANISM: Aids-associated retrovirus

<400> SEQUENCE: 116
aaaattgata gtggga                                                    16

<210> SEQ ID NO 117
<211> LENGTH: 15
<212> TYPE: DNA
<213> ORGANISM: Aids-associated retrovirus

<400> SEQUENCE: 117
caaaattgat agtgg                                                     15

<210> SEQ ID NO 118
<211> LENGTH: 14
<212> TYPE: DNA
<213> ORGANISM: Aids-associated retrovirus

<400> SEQUENCE: 118
aaaatgatag gggg                                                      14

<210> SEQ ID NO 119
<211> LENGTH: 14
<212> TYPE: DNA
<213> ORGANISM: Aids-associated retrovirus

<400> SEQUENCE: 119
aaaaatgata gggg                                                      14

<210> SEQ ID NO 120
<211> LENGTH: 16
<212> TYPE: DNA
<213> ORGANISM: Aids-associated retrovirus

<400> SEQUENCE: 120
aaaaataata ggggga                                                    16
```

-continued

```
<210> SEQ ID NO 121
<211> LENGTH: 18
<212> TYPE: DNA
<213> ORGANISM: Aids-associated retrovirus

<400> SEQUENCE: 121
gggggaattg gaggtttt                                                 18

<210> SEQ ID NO 122
<211> LENGTH: 19
<212> TYPE: DNA
<213> ORGANISM: Aids-associated retrovirus

<400> SEQUENCE: 122 aggggggaatt ggaggtttt                                               19

<210> SEQ ID NO 123
<211> LENGTH: 20
<212> TYPE: DNA
<213> ORGANISM: Aids-associated retrovirus

<400> SEQUENCE: 123 taggggggaat tggaggtttt                                              20

<210> SEQ ID NO 124
<211> LENGTH: 21
<212> TYPE: DNA
<213> ORGANISM: Aids-associated retrovirus

<400> SEQUENCE: 124 aggggggaatt ggaggttttta g                                           21

<210> SEQ ID NO 125
<211> LENGTH: 22
<212> TYPE: DNA
<213> ORGANISM: Aids-associated retrovirus

<400> SEQUENCE: 125 taggggggaat tggaggtttt ag                                           22

<210> SEQ ID NO 126
<211> LENGTH: 21
<212> TYPE: DNA
<213> ORGANISM: Aids-associated retrovirus

<400> SEQUENCE: 126 gtaggggggaa ttggaggttg g                                            21

<210> SEQ ID NO 127
<211> LENGTH: 22
<212> TYPE: DNA
<213> ORGANISM: Aids-associated retrovirus

<400> SEQUENCE: 127
ggtaggggga attggaggtt gg                                            22

<210> SEQ ID NO 128
<211> LENGTH: 21
<212> TYPE: DNA
<213> ORGANISM: Aids-associated retrovirus

<400> SEQUENCE: 128 gtaggggggaa ttggaggttt g                                            21
```

<210> SEQ ID NO 129
<211> LENGTH: 21
<212> TYPE: DNA
<213> ORGANISM: Aids-associated retrovirus

<400> SEQUENCE: 129
gtagggggaa ttggaggttt t                                    21

<210> SEQ ID NO 130
<211> LENGTH: 22
<212> TYPE: DNA
<213> ORGANISM: Aids-associated retrovirus

<400> SEQUENCE: 130
tggtaggggg aattggaggt gg                                   22

<210> SEQ ID NO 131
<211> LENGTH: 17
<212> TYPE: DNA
<213> ORGANISM: Aids-associated retrovirus

<400> SEQUENCE: 131
ggggaattgg aggtttt                                         17

<210> SEQ ID NO 132
<211> LENGTH: 17
<212> TYPE: DNA
<213> ORGANISM: Aids-associated retrovirus

<400> SEQUENCE: 132
ggggaattgg aggtttg                                         17

<210> SEQ ID NO 133
<211> LENGTH: 19
<212> TYPE: DNA
<213> ORGANISM: Aids-associated retrovirus

<400> SEQUENCE: 133
ggggaattgg aggttttag                                       19

<210> SEQ ID NO 134
<211> LENGTH: 16
<212> TYPE: DNA
<213> ORGANISM: Aids-associated retrovirus

<400> SEQUENCE: 134
ggggaattgg aggttg                                          16

<210> SEQ ID NO 135
<211> LENGTH: 18
<212> TYPE: DNA
<213> ORGANISM: Aids-associated retrovirus

<400> SEQUENCE: 135
gggaattgga ggttttat                                        18

<210> SEQ ID NO 136
<211> LENGTH: 17
<212> TYPE: DNA
<213> ORGANISM: Aids-associated retrovirus

<400> SEQUENCE: 136

-continued

| | |
|---|---|
| ggggaattgg aggtttt | 17 |

<210> SEQ ID NO 137
<211> LENGTH: 18
<212> TYPE: DNA
<213> ORGANISM: Aids-associated retrovirus

<400> SEQUENCE: 137

| | |
|---|---|
| gggggagttg gaggtttt | 18 |

<210> SEQ ID NO 138
<211> LENGTH: 19
<212> TYPE: DNA
<213> ORGANISM: Aids-associated retrovirus

<400> SEQUENCE: 138

| | |
|---|---|
| aggggagtt ggaggtttt | 19 |

<210> SEQ ID NO 139
<211> LENGTH: 20
<212> TYPE: DNA
<213> ORGANISM: Aids-associated retrovirus

<400> SEQUENCE: 139

| | |
|---|---|
| taggggagt tggaggtttt | 20 |

<210> SEQ ID NO 140
<211> LENGTH: 21
<212> TYPE: DNA
<213> ORGANISM: Aids-associated retrovirus

<400> SEQUENCE: 140

| | |
|---|---|
| aggggagtt ggaggtttta g | 21 |

<210> SEQ ID NO 141
<211> LENGTH: 22
<212> TYPE: DNA
<213> ORGANISM: Aids-associated retrovirus

<400> SEQUENCE: 141

| | |
|---|---|
| taggggagt tggaggtttt ag | 22 |

<210> SEQ ID NO 142
<211> LENGTH: 21
<212> TYPE: DNA
<213> ORGANISM: Aids-associated retrovirus

<400> SEQUENCE: 142

| | |
|---|---|
| gtaggggag ttggaggttg g | 21 |

<210> SEQ ID NO 143
<211> LENGTH: 22
<212> TYPE: DNA
<213> ORGANISM: Aids-associated retrovirus

<400> SEQUENCE: 143

| | |
|---|---|
| ggtaggggga gttggaggtt gg | 22 |

<210> SEQ ID NO 144
<211> LENGTH: 21
<212> TYPE: DNA
<213> ORGANISM: Aids-associated retrovirus

<400> SEQUENCE: 144

```
gtaggggag ttggaggttt g                                            21

<210> SEQ ID NO 145
<211> LENGTH: 24
<212> TYPE: DNA
<213> ORGANISM: Aids-associated retrovirus

<400> SEQUENCE: 145 gtaggggag ttggaggttt tatc                                         24

<210> SEQ ID NO 146
<211> LENGTH: 22
<212> TYPE: DNA
<213> ORGANISM: Aids-associated retrovirus

<400> SEQUENCE: 146 tggtagggg agttggaggt gg                                           22

<210> SEQ ID NO 147
<211> LENGTH: 17
<212> TYPE: DNA
<213> ORGANISM: Aids-associated retrovirus

<400> SEQUENCE: 147
ggggagttgg aggtttg                                                17

<210> SEQ ID NO 148
<211> LENGTH: 19
<212> TYPE: DNA
<213> ORGANISM: Aids-associated retrovirus

<400> SEQUENCE: 148
ggggagttgg aggttttag                                              19

<210> SEQ ID NO 149
<211> LENGTH: 16
<212> TYPE: DNA
<213> ORGANISM: Aids-associated retrovirus

<400> SEQUENCE: 149
ggggagttgg aggttg                                                 16

<210> SEQ ID NO 150
<211> LENGTH: 18
<212> TYPE: DNA
<213> ORGANISM: Aids-associated retrovirus

<400> SEQUENCE: 150
gggagttgga ggttttat                                               18

<210> SEQ ID NO 151
<211> LENGTH: 15
<212> TYPE: DNA
<213> ORGANISM: Aids-associated retrovirus

<400> SEQUENCE: 151
ggaattggag gtttt                                                  15

<210> SEQ ID NO 152
<211> LENGTH: 16
<212> TYPE: DNA
<213> ORGANISM: Aids-associated retrovirus
```

-continued

```
<400> SEQUENCE: 152
gggaattgga ggttgg                                                        16

<210> SEQ ID NO 153
<211> LENGTH: 15
<212> TYPE: DNA
<213> ORGANISM: Aids-associated retrovirus

<400> SEQUENCE: 153
ggagttggag gtttt                                                         15

<210> SEQ ID NO 154
<211> LENGTH: 16
<212> TYPE: DNA
<213> ORGANISM: Aids-associated retrovirus

<400> SEQUENCE: 154
gggagttgga ggttgg                                                        16

<210> SEQ ID NO 155
<211> LENGTH: 13
<212> TYPE: DNA
<213> ORGANISM: Aids-associated retrovirus

<400> SEQUENCE: 155
gggggagttg gag                                                           13

<210> SEQ ID NO 156
<211> LENGTH: 12
<212> TYPE: DNA
<213> ORGANISM: Aids-associated retrovirus

<400> SEQUENCE: 156
ggggagttgg ag                                                            12

<210> SEQ ID NO 157
<211> LENGTH: 12
<212> TYPE: DNA
<213> ORGANISM: Aids-associated retrovirus

<400> SEQUENCE: 157
gggggagttg ga                                                            12

<210> SEQ ID NO 158
<211> LENGTH: 15
<212> TYPE: DNA
<213> ORGANISM: Aids-associated retrovirus

<400> SEQUENCE: 158
ggaattgggg gtttg                                                         15

<210> SEQ ID NO 159
<211> LENGTH: 14
<212> TYPE: DNA
<213> ORGANISM: Aids-associated retrovirus

<400> SEQUENCE: 159
gaattggggg tttt                                                          14

<210> SEQ ID NO 160
<211> LENGTH: 16
<212> TYPE: DNA
<213> ORGANISM: Aids-associated retrovirus
```

-continued

```
<400> SEQUENCE: 160
gaattggggg ttttag                                              16

<210> SEQ ID NO 161
<211> LENGTH: 14
<212> TYPE: DNA
<213> ORGANISM: Aids-associated retrovirus

<400> SEQUENCE: 161
ggaattgggg gttg                                                14

<210> SEQ ID NO 162
<211> LENGTH: 13
<212> TYPE: DNA
<213> ORGANISM: Aids-associated retrovirus

<400> SEQUENCE: 162
ggaattgggg gtg                                                 13

<210> SEQ ID NO 163
<211> LENGTH: 13
<212> TYPE: DNA
<213> ORGANISM: Aids-associated retrovirus

<400> SEQUENCE: 163
gaattggggg ttg                                                 13

<210> SEQ ID NO 164
<211> LENGTH: 14
<212> TYPE: DNA
<213> ORGANISM: Aids-associated retrovirus

<400> SEQUENCE: 164
ggaattgggg gttt                                                14

<210> SEQ ID NO 165
<211> LENGTH: 13
<212> TYPE: DNA
<213> ORGANISM: Aids-associated retrovirus

<400> SEQUENCE: 165
gggggaattg cag                                                 13

<210> SEQ ID NO 166
<211> LENGTH: 14
<212> TYPE: DNA
<213> ORGANISM: Aids-associated retrovirus

<400> SEQUENCE: 166
ggaattgcag gttg                                                14

<210> SEQ ID NO 167
<211> LENGTH: 13
<212> TYPE: DNA
<213> ORGANISM: Aids-associated retrovirus

<400> SEQUENCE: 167
ggaattgcag gtg                                                 13

<210> SEQ ID NO 168
<211> LENGTH: 15
<212> TYPE: DNA
```

<213> ORGANISM: Aids-associated retrovirus

<400> SEQUENCE: 168
ggaattggag ggttg                                           15

<210> SEQ ID NO 169
<211> LENGTH: 14
<212> TYPE: DNA
<213> ORGANISM: Aids-associated retrovirus

<400> SEQUENCE: 169
gaattggagg gttg                                            14

<210> SEQ ID NO 170
<211> LENGTH: 14
<212> TYPE: DNA
<213> ORGANISM: Aids-associated retrovirus

<400> SEQUENCE: 170
gaattggagg gttt                                            14

<210> SEQ ID NO 171
<211> LENGTH: 15
<212> TYPE: DNA
<213> ORGANISM: Aids-associated retrovirus

<400> SEQUENCE: 171
ggaattggag gcttg                                           15

<210> SEQ ID NO 172
<211> LENGTH: 14
<212> TYPE: DNA
<213> ORGANISM: Aids-associated retrovirus

<400> SEQUENCE: 172
gaattggagg cttg                                            14

<210> SEQ ID NO 173
<211> LENGTH: 14
<212> TYPE: DNA
<213> ORGANISM: Aids-associated retrovirus

<400> SEQUENCE: 173
gaattggagg cttt                                            14

<210> SEQ ID NO 174
<211> LENGTH: 15
<212> TYPE: DNA
<213> ORGANISM: Aids-associated retrovirus

<400> SEQUENCE: 174
ggagttggag gtttg                                           15

<210> SEQ ID NO 175
<211> LENGTH: 14
<212> TYPE: DNA
<213> ORGANISM: Aids-associated retrovirus

<400> SEQUENCE: 175
gagttggagg tttt                                            14

<210> SEQ ID NO 176
<211> LENGTH: 16

```
<212> TYPE: DNA
<213> ORGANISM: Aids-associated retrovirus

<400> SEQUENCE: 176
ggttttatca aagtaa                                                       16

<210> SEQ ID NO 177
<211> LENGTH: 16
<212> TYPE: DNA
<213> ORGANISM: Aids-associated retrovirus

<400> SEQUENCE: 177
gttttatcaa agtaag                                                       16

<210> SEQ ID NO 178
<211> LENGTH: 17
<212> TYPE: DNA
<213> ORGANISM: Aids-associated retrovirus

<400> SEQUENCE: 178
gttttatcaa agtaaga                                                      17

<210> SEQ ID NO 179
<211> LENGTH: 16
<212> TYPE: DNA
<213> ORGANISM: Aids-associated retrovirus

<400> SEQUENCE: 179
ttttatcaaa gtaaga                                                       16

<210> SEQ ID NO 180
<211> LENGTH: 15
<212> TYPE: DNA
<213> ORGANISM: Aids-associated retrovirus

<400> SEQUENCE: 180
ggttttatca aagta                                                        15

<210> SEQ ID NO 181
<211> LENGTH: 14
<212> TYPE: DNA
<213> ORGANISM: Aids-associated retrovirus

<400> SEQUENCE: 181
gttttatcaa agta                                                         14

<210> SEQ ID NO 182
<211> LENGTH: 15
<212> TYPE: DNA
<213> ORGANISM: Aids-associated retrovirus

<400> SEQUENCE: 182
ggttttgcca aagta                                                        15

<210> SEQ ID NO 183
<211> LENGTH: 15
<212> TYPE: DNA
<213> ORGANISM: Aids-associated retrovirus

<400> SEQUENCE: 183
gttttgccaa agtaa                                                        15

<210> SEQ ID NO 184
```

```
<211> LENGTH: 16
<212> TYPE: DNA
<213> ORGANISM: Aids-associated retrovirus

<400> SEQUENCE: 184
gttttgccaa agtaag                                                    16

<210> SEQ ID NO 185
<211> LENGTH: 16
<212> TYPE: DNA
<213> ORGANISM: Aids-associated retrovirus

<400> SEQUENCE: 185
ttttgccaaa gtaaga                                                    16

<210> SEQ ID NO 186
<211> LENGTH: 14
<212> TYPE: DNA
<213> ORGANISM: Aids-associated retrovirus

<400> SEQUENCE: 186
ggttttgcca aagt                                                      14

<210> SEQ ID NO 187
<211> LENGTH: 14
<212> TYPE: DNA
<213> ORGANISM: Aids-associated retrovirus

<400> SEQUENCE: 187
gttttgccaa agta                                                      14

<210> SEQ ID NO 188
<211> LENGTH: 16
<212> TYPE: DNA
<213> ORGANISM: Aids-associated retrovirus

<400> SEQUENCE: 188
gttttatcaa ggtaaa                                                    16

<210> SEQ ID NO 189
<211> LENGTH: 16
<212> TYPE: DNA
<213> ORGANISM: Aids-associated retrovirus

<400> SEQUENCE: 189
ggttttatca aggtaa                                                    16

<210> SEQ ID NO 190
<211> LENGTH: 16
<212> TYPE: DNA
<213> ORGANISM: Aids-associated retrovirus

<400> SEQUENCE: 190
aggttttatc aaggta                                                    16

<210> SEQ ID NO 191
<211> LENGTH: 17
<212> TYPE: DNA
<213> ORGANISM: Aids-associated retrovirus

<400> SEQUENCE: 191
gttttatcaa agtcaga                                                   17
```

```
<210> SEQ ID NO 192
<211> LENGTH: 16
<212> TYPE: DNA
<213> ORGANISM: Aids-associated retrovirus

<400> SEQUENCE: 192
tttatcaaag tcagac                                                     16

<210> SEQ ID NO 193
<211> LENGTH: 17
<212> TYPE: DNA
<213> ORGANISM: Aids-associated retrovirus

<400> SEQUENCE: 193
aggctttatc aaagtaa                                                    17

<210> SEQ ID NO 194
<211> LENGTH: 16
<212> TYPE: DNA
<213> ORGANISM: Aids-associated retrovirus

<400> SEQUENCE: 194
aggctttatc aaagta                                                     16

<210> SEQ ID NO 195
<211> LENGTH: 17
<212> TYPE: DNA
<213> ORGANISM: Aids-associated retrovirus

<400> SEQUENCE: 195
aggttttatt aaagtaa                                                    17

<210> SEQ ID NO 196
<211> LENGTH: 17
<212> TYPE: DNA
<213> ORGANISM: Aids-associated retrovirus

<400> SEQUENCE: 196
ggttttatta aagtaag                                                    17

<210> SEQ ID NO 197
<211> LENGTH: 17
<212> TYPE: DNA
<213> ORGANISM: Aids-associated retrovirus

<400> SEQUENCE: 197
gaggttttat taaagta                                                    17

<210> SEQ ID NO 198
<211> LENGTH: 17
<212> TYPE: DNA
<213> ORGANISM: Aids-associated retrovirus

<400> SEQUENCE: 198
gaggttttat taaagta                                                    17

<210> SEQ ID NO 199
<211> LENGTH: 17
<212> TYPE: DNA
<213> ORGANISM: Aids-associated retrovirus

<400> SEQUENCE: 199
ggttttattg gttttat                                                    17
```

```
<210> SEQ ID NO 200
<211> LENGTH: 15
<212> TYPE: DNA
<213> ORGANISM: Aids-associated retrovirus

<400> SEQUENCE: 200
ggtttcatta aggta                                                    15

<210> SEQ ID NO 201
<211> LENGTH: 16
<212> TYPE: DNA
<213> ORGANISM: Aids-associated retrovirus

<400> SEQUENCE: 201
ggtttcatta aggtaa                                                   16

<210> SEQ ID NO 202
<211> LENGTH: 16
<212> TYPE: DNA
<213> ORGANISM: Aids-associated retrovirus

<400> SEQUENCE: 202
aggtttcatt aaggta                                                   16

<210> SEQ ID NO 203
<211> LENGTH: 16
<212> TYPE: DNA
<213> ORGANISM: Aids-associated retrovirus

<400> SEQUENCE: 203
aggtttcatt aaggta                                                   16

<210> SEQ ID NO 204
<211> LENGTH: 16
<212> TYPE: DNA
<213> ORGANISM: Aids-associated retrovirus

<400> SEQUENCE: 204
ggttttatta aggtaa                                                   16

<210> SEQ ID NO 205
<211> LENGTH: 16
<212> TYPE: DNA
<213> ORGANISM: Aids-associated retrovirus

<400> SEQUENCE: 205
ggttttatta aggtaa                                                   16

<210> SEQ ID NO 206
<211> LENGTH: 16
<212> TYPE: DNA
<213> ORGANISM: Aids-associated retrovirus

<400> SEQUENCE: 206
aggttttatt aaggta                                                   16

<210> SEQ ID NO 207
<211> LENGTH: 16
<212> TYPE: DNA
<213> ORGANISM: Aids-associated retrovirus

<400> SEQUENCE: 207
gaggttttat taaggt                                                   16
```

<210> SEQ ID NO 208
<211> LENGTH: 17
<212> TYPE: DNA
<213> ORGANISM: Aids-associated retrovirus

<400> SEQUENCE: 208
ggttttatta aggtaag                                                17

<210> SEQ ID NO 209
<211> LENGTH: 16
<212> TYPE: DNA
<213> ORGANISM: Aids-associated retrovirus

<400> SEQUENCE: 209
ggttttatca aagtaa                                                 16

<210> SEQ ID NO 210
<211> LENGTH: 17
<212> TYPE: DNA
<213> ORGANISM: Aids-associated retrovirus

<400> SEQUENCE: 210
aggttttatc aaagtaa                                                17

<210> SEQ ID NO 211
<211> LENGTH: 16
<212> TYPE: DNA
<213> ORGANISM: Aids-associated retrovirus

<400> SEQUENCE: 211
aggttttatc aaagta                                                 16

<210> SEQ ID NO 212
<211> LENGTH: 16
<212> TYPE: DNA
<213> ORGANISM: Aids-associated retrovirus

<400> SEQUENCE: 212
gaggttttat caaagt                                                 16

<210> SEQ ID NO 213
<211> LENGTH: 15
<212> TYPE: DNA
<213> ORGANISM: Aids-associated retrovirus

<400> SEQUENCE: 213
ggttttgtca aagta                                                  15

<210> SEQ ID NO 214
<211> LENGTH: 16
<212> TYPE: DNA
<213> ORGANISM: Aids-associated retrovirus

<400> SEQUENCE: 214
ggttttgtca aagtaa                                                 16

<210> SEQ ID NO 215
<211> LENGTH: 15
<212> TYPE: DNA
<213> ORGANISM: Aids-associated retrovirus

<400> SEQUENCE: 215

-continued

```
ggttttgtca gagta                                                  15

<210> SEQ ID NO 216
<211> LENGTH: 16
<212> TYPE: DNA
<213> ORGANISM: Aids-associated retrovirus

<400> SEQUENCE: 216
ggttttgtca gagtaa                                                 16

<210> SEQ ID NO 217
<211> LENGTH: 15
<212> TYPE: DNA
<213> ORGANISM: Aids-associated retrovirus

<400> SEQUENCE: 217
gggtttatca aagta                                                  15

<210> SEQ ID NO 218
<211> LENGTH: 16
<212> TYPE: DNA
<213> ORGANISM: Aids-associated retrovirus

<400> SEQUENCE: 218
gggtttatca aagtaa                                                 16

<210> SEQ ID NO 219
<211> LENGTH: 14
<212> TYPE: DNA
<213> ORGANISM: Aids-associated retrovirus

<400> SEQUENCE: 219
ggcttcatca aagt                                                   14

<210> SEQ ID NO 220
<211> LENGTH: 14
<212> TYPE: DNA
<213> ORGANISM: Aids-associated retrovirus

<400> SEQUENCE: 220
gaggcttcat caaa                                                   14

<210> SEQ ID NO 221
<211> LENGTH: 14
<212> TYPE: DNA
<213> ORGANISM: Aids-associated retrovirus

<400> SEQUENCE: 221
ggttttgtca aagt                                                   14

<210> SEQ ID NO 222
<211> LENGTH: 14
<212> TYPE: DNA
<213> ORGANISM: Aids-associated retrovirus

<400> SEQUENCE: 222
gttttgtcag agta                                                   14

<210> SEQ ID NO 223
<211> LENGTH: 14
<212> TYPE: DNA
<213> ORGANISM: Aids-associated retrovirus

<400> SEQUENCE: 223
```

```
ggttttgtca gagt                                                              14

<210> SEQ ID NO 224
<211> LENGTH: 16
<212> TYPE: DNA
<213> ORGANISM: Aids-associated retrovirus

<400> SEQUENCE: 224
aggtttaatc aaagta                                                            16

<210> SEQ ID NO 225
<211> LENGTH: 16
<212> TYPE: DNA
<213> ORGANISM: Aids-associated retrovirus

<400> SEQUENCE: 225
gaggtttaat caaagt                                                            16

<210> SEQ ID NO 226
<211> LENGTH: 15
<212> TYPE: DNA
<213> ORGANISM: Aids-associated retrovirus

<400> SEQUENCE: 226
ggttttacca aagta                                                             15

<210> SEQ ID NO 227
<211> LENGTH: 14
<212> TYPE: DNA
<213> ORGANISM: Aids-associated retrovirus

<400> SEQUENCE: 227
ggttttacca aagt                                                              14

<210> SEQ ID NO 228
<211> LENGTH: 20
<212> TYPE: DNA
<213> ORGANISM: Aids-associated retrovirus

<400> SEQUENCE: 228
cctacacctg tcaacataag                                                        20

<210> SEQ ID NO 229
<211> LENGTH: 21
<212> TYPE: DNA
<213> ORGANISM: Aids-associated retrovirus

<400> SEQUENCE: 229
cctacacctg tcaacataat g                                                      21

<210> SEQ ID NO 230
<211> LENGTH: 21
<212> TYPE: DNA
<213> ORGANISM: Aids-associated retrovirus

<400> SEQUENCE: 230
cctacacctg tcaacataat t                                                      21

<210> SEQ ID NO 231
<211> LENGTH: 21
<212> TYPE: DNA
<213> ORGANISM: Aids-associated retrovirus
```

-continued

```
<400> SEQUENCE: 231
acctacacct gtcaacataa g                                         21

<210> SEQ ID NO 232
<211> LENGTH: 22
<212> TYPE: DNA
<213> ORGANISM: Aids-associated retrovirus

<400> SEQUENCE: 232
acctacacct gtcaacataa tg                                        22

<210> SEQ ID NO 233
<211> LENGTH: 19
<212> TYPE: DNA
<213> ORGANISM: Aids-associated retrovirus

<400> SEQUENCE: 233
acctacacct gtcaacata                                            19

<210> SEQ ID NO 234
<211> LENGTH: 20
<212> TYPE: DNA
<213> ORGANISM: Aids-associated retrovirus

<400> SEQUENCE: 234
gacctacacc tgtcaacata                                           20

<210> SEQ ID NO 235
<211> LENGTH: 20
<212> TYPE: DNA
<213> ORGANISM: Aids-associated retrovirus

<400> SEQUENCE: 235
cacctgtcaa cataattgga                                           20

<210> SEQ ID NO 236
<211> LENGTH: 20
<212> TYPE: DNA
<213> ORGANISM: Aids-associated retrovirus

<400> SEQUENCE: 236
acctgtcaac ataattggaa                                           20

<210> SEQ ID NO 237
<211> LENGTH: 20
<212> TYPE: DNA
<213> ORGANISM: Aids-associated retrovirus

<400> SEQUENCE: 237
acacctgtca acataattgg                                           20

<210> SEQ ID NO 238
<211> LENGTH: 19
<212> TYPE: DNA
<213> ORGANISM: Aids-associated retrovirus

<400> SEQUENCE: 238
acctgtcaac ataattgga                                            19

<210> SEQ ID NO 239
<211> LENGTH: 20
<212> TYPE: DNA
<213> ORGANISM: Aids-associated retrovirus
```

```
<400> SEQUENCE: 239
cctacaccta ccaacataag                                          20

<210> SEQ ID NO 240
<211> LENGTH: 21
<212> TYPE: DNA
<213> ORGANISM: Aids-associated retrovirus

<400> SEQUENCE: 240
cctacaccta ccaacataat g                                        21

<210> SEQ ID NO 241
<211> LENGTH: 21
<212> TYPE: DNA
<213> ORGANISM: Aids-associated retrovirus

<400> SEQUENCE: 241
cctacaccta ccaacataat t                                        21

<210> SEQ ID NO 242
<211> LENGTH: 21
<212> TYPE: DNA
<213> ORGANISM: Aids-associated retrovirus

<400> SEQUENCE: 242
acctacacct accaacataa g                                        21

<210> SEQ ID NO 243
<211> LENGTH: 22
<212> TYPE: DNA
<213> ORGANISM: Aids-associated retrovirus

<400> SEQUENCE: 243
acctacacct accaacataa tg                                       22

<210> SEQ ID NO 244
<211> LENGTH: 19
<212> TYPE: DNA
<213> ORGANISM: Aids-associated retrovirus

<400> SEQUENCE: 244
acctacacct accaacata                                           19

<210> SEQ ID NO 245
<211> LENGTH: 20
<212> TYPE: DNA
<213> ORGANISM: Aids-associated retrovirus

<400> SEQUENCE: 245
gacctacacc taccaacata                                          20

<210> SEQ ID NO 246
<211> LENGTH: 20
<212> TYPE: DNA
<213> ORGANISM: Aids-associated retrovirus

<400> SEQUENCE: 246
cacctaccaa cataattgga                                          20

<210> SEQ ID NO 247
<211> LENGTH: 20
<212> TYPE: DNA
```

<213> ORGANISM: Aids-associated retrovirus

<400> SEQUENCE: 247
acctaccaac ataattggaa                    20

<210> SEQ ID NO 248
<211> LENGTH: 19
<212> TYPE: DNA
<213> ORGANISM: Aids-associated retrovirus

<400> SEQUENCE: 248
acacctacca acataattg                    19

<210> SEQ ID NO 249
<211> LENGTH: 21
<212> TYPE: DNA
<213> ORGANISM: Aids-associated retrovirus

<400> SEQUENCE: 249
cctacacctt tcaacataat t                    21

<210> SEQ ID NO 250
<211> LENGTH: 21
<212> TYPE: DNA
<213> ORGANISM: Aids-associated retrovirus

<400> SEQUENCE: 250
cctacacctg ccaacataat t                    21

<210> SEQ ID NO 251
<211> LENGTH: 21
<212> TYPE: DNA
<213> ORGANISM: Aids-associated retrovirus

<400> SEQUENCE: 251 cctacaccttt ccaacataat t                    21

<210> SEQ ID NO 252
<211> LENGTH: 20
<212> TYPE: DNA
<213> ORGANISM: Aids-associated retrovirus

<400> SEQUENCE: 252
acctttcaac ataattggaa                    20

<210> SEQ ID NO 253
<211> LENGTH: 20
<212> TYPE: DNA
<213> ORGANISM: Aids-associated retrovirus

<400> SEQUENCE: 253
acctgccaac ataattggaa                    20

<210> SEQ ID NO 254
<211> LENGTH: 20
<212> TYPE: DNA
<213> ORGANISM: Aids-associated retrovirus

<400> SEQUENCE: 254
acctttcaac ataattggaa                    20

<210> SEQ ID NO 255
<211> LENGTH: 16

```
<212> TYPE: DNA
<213> ORGANISM: Aids-associated retrovirus

<400> SEQUENCE: 255
acctaccaac ataatt                                                     16

<210> SEQ ID NO 256
<211> LENGTH: 19
<212> TYPE: DNA
<213> ORGANISM: Aids-associated retrovirus

<400> SEQUENCE: 256
acctttcaac ataattgga                                                  19

<210> SEQ ID NO 257
<211> LENGTH: 19
<212> TYPE: DNA
<213> ORGANISM: Aids-associated retrovirus

<400> SEQUENCE: 257
acctgccaac ataattgga                                                  19

<210> SEQ ID NO 258
<211> LENGTH: 19
<212> TYPE: DNA
<213> ORGANISM: Aids-associated retrovirus

<400> SEQUENCE: 258
accttccaac ataattgga                                                  19

<210> SEQ ID NO 259
<211> LENGTH: 15
<212> TYPE: DNA
<213> ORGANISM: Aids-associated retrovirus

<400> SEQUENCE: 259
tacacctgtc aacat                                                      15

<210> SEQ ID NO 260
<211> LENGTH: 16
<212> TYPE: DNA
<213> ORGANISM: Aids-associated retrovirus

<400> SEQUENCE: 260
tacacctgtc aacata                                                     16

<210> SEQ ID NO 261
<211> LENGTH: 15
<212> TYPE: DNA
<213> ORGANISM: Aids-associated retrovirus

<400> SEQUENCE: 261
acacctgtca acata                                                      15

<210> SEQ ID NO 262
<211> LENGTH: 14
<212> TYPE: DNA
<213> ORGANISM: Aids-associated retrovirus

<400> SEQUENCE: 262
cacctgtcaa cata                                                       14

<210> SEQ ID NO 263
```

```
<211> LENGTH: 15
<212> TYPE: DNA
<213> ORGANISM: Aids-associated retrovirus

<400> SEQUENCE: 263
acacctacca acata                                               15

<210> SEQ ID NO 264
<211> LENGTH: 14
<212> TYPE: DNA
<213> ORGANISM: Aids-associated retrovirus

<400> SEQUENCE: 264
cacctaccaa cata                                                14

<210> SEQ ID NO 265
<211> LENGTH: 15
<212> TYPE: DNA
<213> ORGANISM: Aids-associated retrovirus

<400> SEQUENCE: 265
acaccttcca acata                                               15

<210> SEQ ID NO 266
<211> LENGTH: 14
<212> TYPE: DNA
<213> ORGANISM: Aids-associated retrovirus

<400> SEQUENCE: 266 caccttcaa cata                                                 14

<210> SEQ ID NO 267
<211> LENGTH: 15
<212> TYPE: DNA
<213> ORGANISM: Aids-associated retrovirus

<400> SEQUENCE: 267
acacctgcca acata                                               15

<210> SEQ ID NO 268
<211> LENGTH: 14
<212> TYPE: DNA
<213> ORGANISM: Aids-associated retrovirus

<400> SEQUENCE: 268
cacctgccaa cata                                                14

<210> SEQ ID NO 269
<211> LENGTH: 14
<212> TYPE: DNA
<213> ORGANISM: Aids-associated retrovirus

<400> SEQUENCE: 269
cacctgtcaa cgta                                                14

<210> SEQ ID NO 270
<211> LENGTH: 13
<212> TYPE: DNA
<213> ORGANISM: Aids-associated retrovirus

<400> SEQUENCE: 270
cacctgtcaa cgt                                                 13
```

```
<210> SEQ ID NO 271
<211> LENGTH: 15
<212> TYPE: DNA
<213> ORGANISM: Aids-associated retrovirus

<400> SEQUENCE: 271
cctacacctg tcaac                                                    15

<210> SEQ ID NO 272
<211> LENGTH: 15
<212> TYPE: DNA
<213> ORGANISM: Aids-associated retrovirus

<400> SEQUENCE: 272
tacgcctgtc aacat                                                    15

<210> SEQ ID NO 273
<211> LENGTH: 16
<212> TYPE: DNA
<213> ORGANISM: Aids-associated retrovirus

<400> SEQUENCE: 273
ctacgcctgt caacag                                                   16

<210> SEQ ID NO 274
<211> LENGTH: 15
<212> TYPE: DNA
<213> ORGANISM: Aids-associated retrovirus

<400> SEQUENCE: 274
acaccttcca acata                                                    15

<210> SEQ ID NO 275
<211> LENGTH: 14
<212> TYPE: DNA
<213> ORGANISM: Aids-associated retrovirus

<400> SEQUENCE: 275
caccttccaa cata                                                     14

<210> SEQ ID NO 276
<211> LENGTH: 14
<212> TYPE: DNA
<213> ORGANISM: Aids-associated retrovirus

<400> SEQUENCE: 276
acaccttcca acat                                                     14

<210> SEQ ID NO 277
<211> LENGTH: 15
<212> TYPE: DNA
<213> ORGANISM: Aids-associated retrovirus

<400> SEQUENCE: 277
acacctatca acata                                                    15

<210> SEQ ID NO 278
<211> LENGTH: 16
<212> TYPE: DNA
<213> ORGANISM: Aids-associated retrovirus

<400> SEQUENCE: 278
cacctatcaa cataag                                                   16
```

```
<210> SEQ ID NO 279
<211> LENGTH: 17
<212> TYPE: DNA
<213> ORGANISM: Aids-associated retrovirus

<400> SEQUENCE: 279
cacctatcaa cataatg                                                    17

<210> SEQ ID NO 280
<211> LENGTH: 16
<212> TYPE: DNA
<213> ORGANISM: Aids-associated retrovirus

<400> SEQUENCE: 280
acctatcaac ataatg                                                     16

<210> SEQ ID NO 281
<211> LENGTH: 15
<212> TYPE: DNA
<213> ORGANISM: Aids-associated retrovirus

<400> SEQUENCE: 281
cctgtcaaca taatt                                                      15

<210> SEQ ID NO 282
<211> LENGTH: 16
<212> TYPE: DNA
<213> ORGANISM: Aids-associated retrovirus

<400> SEQUENCE: 282
cctgttaaca taattg                                                     16

<210> SEQ ID NO 283
<211> LENGTH: 16
<212> TYPE: DNA
<213> ORGANISM: Aids-associated retrovirus

<400> SEQUENCE: 283
acctgttaac ataatg                                                     16

<210> SEQ ID NO 284
<211> LENGTH: 15
<212> TYPE: DNA
<213> ORGANISM: Aids-associated retrovirus

<400> SEQUENCE: 284
ccggtcaaca taatt                                                      15

<210> SEQ ID NO 285
<211> LENGTH: 14
<212> TYPE: DNA
<213> ORGANISM: Aids-associated retrovirus

<400> SEQUENCE: 285
acgcctgtca acat                                                       14

<210> SEQ ID NO 286
<211> LENGTH: 15
<212> TYPE: DNA
<213> ORGANISM: Aids-associated retrovirus

<400> SEQUENCE: 286
cctgtcaata taatt                                                      15
```

```
<210> SEQ ID NO 287
<211> LENGTH: 17
<212> TYPE: DNA
<213> ORGANISM: Aids-associated retrovirus

<400> SEQUENCE: 287
cacctgtcaa tataatg                                                    17

<210> SEQ ID NO 288
<211> LENGTH: 17
<212> TYPE: DNA
<213> ORGANISM: Aids-associated retrovirus

<400> SEQUENCE: 288
acacctgtca atataag                                                    17

<210> SEQ ID NO 289
<211> LENGTH: 15
<212> TYPE: DNA
<213> ORGANISM: Aids-associated retrovirus

<400> SEQUENCE: 289
cctgccaata taatt                                                      15

<210> SEQ ID NO 290
<211> LENGTH: 16
<212> TYPE: DNA
<213> ORGANISM: Aids-associated retrovirus

<400> SEQUENCE: 290
cacctgccaa tataag                                                     16

<210> SEQ ID NO 291
<211> LENGTH: 15
<212> TYPE: DNA
<213> ORGANISM: Aids-associated retrovirus

<400> SEQUENCE: 291
cctaccaacg taatt                                                      15

<210> SEQ ID NO 292
<211> LENGTH: 15
<212> TYPE: DNA
<213> ORGANISM: Aids-associated retrovirus

<400> SEQUENCE: 292
cctaccaacg taatg                                                      15

<210> SEQ ID NO 293
<211> LENGTH: 14
<212> TYPE: DNA
<213> ORGANISM: Aids-associated retrovirus

<400> SEQUENCE: 293
cacctaccaa cgta                                                       14

<210> SEQ ID NO 294
<211> LENGTH: 14
<212> TYPE: DNA
<213> ORGANISM: Aids-associated retrovirus

<400> SEQUENCE: 294
```

-continued acacctacca acgt                                                          14

<210> SEQ ID NO 295
<211> LENGTH: 15
<212> TYPE: DNA
<213> ORGANISM: Aids-associated retrovirus

<400> SEQUENCE: 295
cctttcaacg taatt                                                         15

<210> SEQ ID NO 296
<211> LENGTH: 16
<212> TYPE: DNA
<213> ORGANISM: Aids-associated retrovirus

<400> SEQUENCE: 296
cacctttcaa cgtaag                                                        16

<210> SEQ ID NO 297
<211> LENGTH: 15
<212> TYPE: DNA
<213> ORGANISM: Aids-associated retrovirus

<400> SEQUENCE: 297
acacctttca acgta                                                         15

<210> SEQ ID NO 298
<211> LENGTH: 16
<212> TYPE: DNA
<213> ORGANISM: Aids-associated retrovirus

<400> SEQUENCE: 298
acctttcaac gtaatg                                                        16

<210> SEQ ID NO 299
<211> LENGTH: 15
<212> TYPE: DNA
<213> ORGANISM: Aids-associated retrovirus

<400> SEQUENCE: 299
ctgtcaatat aattg                                                         15

<210> SEQ ID NO 300
<211> LENGTH: 16
<212> TYPE: DNA
<213> ORGANISM: Aids-associated

<400> SEQUENCE: 300
cctgtcaata taattg                                                        16

<210> SEQ ID NO 301
<211> LENGTH: 16
<212> TYPE: DNA
<213> ORGANISM: Aids-associated retrovirus

<400> SEQUENCE: 301
acctgtcaat ataatt                                                        16

<210> SEQ ID NO 302
<211> LENGTH: 16
<212> TYPE: DNA
<213> ORGANISM: Aids-associated retrovirus

<400> SEQUENCE: 302

```
ctgtcaatat aattgg                                              16

<210> SEQ ID NO 303
<211> LENGTH: 14
<212> TYPE: DNA
<213> ORGANISM: Aids-associated retrovirus

<400> SEQUENCE: 303
cctacgcctg tcaa                                                14

<210> SEQ ID NO 304
<211> LENGTH: 14
<212> TYPE: DNA
<213> ORGANISM: Aids-associated retrovirus

<400> SEQUENCE: 304
ctacgcctgt caac                                                14

<210> SEQ ID NO 305
<211> LENGTH: 15
<212> TYPE: DNA
<213> ORGANISM: Aids-associated retrovirus

<400> SEQUENCE: 305
acctacgcct gtcaa                                               15

<210> SEQ ID NO 306
<211> LENGTH: 14
<212> TYPE: DNA
<213> ORGANISM: Aids-associated retrovirus

<400> SEQUENCE: 306
acctacgcct gtca                                                14

<210> SEQ ID NO 307
<211> LENGTH: 14
<212> TYPE: DNA
<213> ORGANISM: Aids-associated retrovirus

<400> SEQUENCE: 307
tacaccggtc aaca                                                14

<210> SEQ ID NO 308
<211> LENGTH: 13
<212> TYPE: DNA
<213> ORGANISM: Aids-associated retrovirus

<400> SEQUENCE: 308
ctacaccggt caa                                                 13

<210> SEQ ID NO 309
<211> LENGTH: 13
<212> TYPE: DNA
<213> ORGANISM: Aids-associated retrovirus

<400> SEQUENCE: 309
cctacaccgg tca                                                 13

<210> SEQ ID NO 310
<211> LENGTH: 15
<212> TYPE: DNA
<213> ORGANISM: Aids-associated retrovirus
```

```
<400> SEQUENCE: 310
cacctgtcaa cataa                                                15

<210> SEQ ID NO 311
<211> LENGTH: 15
<212> TYPE: DNA
<213> ORGANISM: Aids-associated retrovirus

<400> SEQUENCE: 311
acctgtcaac ataat                                                15

<210> SEQ ID NO 312
<211> LENGTH: 15
<212> TYPE: DNA
<213> ORGANISM: Aids-associated retrovirus

<400> SEQUENCE: 312
ctacacctgt caaca                                                15

<210> SEQ ID NO 313
<211> LENGTH: 14
<212> TYPE: DNA
<213> ORGANISM: Aids-associated retrovirus

<400> SEQUENCE: 313
acacctgtca acat                                                 14

<210> SEQ ID NO 314
<211> LENGTH: 17
<212> TYPE: DNA
<213> ORGANISM: Aids-associated retrovirus

<400> SEQUENCE: 314
acctgttaac ataattg                                              17

<210> SEQ ID NO 315
<211> LENGTH: 16
<212> TYPE: DNA
<213> ORGANISM: Aids-associated retrovirus

<400> SEQUENCE: 315
cacctgttaa cataag                                               16

<210> SEQ ID NO 316
<211> LENGTH: 17
<212> TYPE: DNA
<213> ORGANISM: Aids-associated retrovirus

<400> SEQUENCE: 316
acacctgtta acataag                                              17

<210> SEQ ID NO 317
<211> LENGTH: 15
<212> TYPE: DNA
<213> ORGANISM: Aids-associated retrovirus

<400> SEQUENCE: 317
tcacctgtca acata                                                15

<210> SEQ ID NO 318
<211> LENGTH: 16
<212> TYPE: DNA
<213> ORGANISM: Aids-associated retrovirus
```

-continued

```
<400> SEQUENCE: 318
acacctgtca acataa                                               16

<210> SEQ ID NO 319
<211> LENGTH: 16
<212> TYPE: DNA
<213> ORGANISM: Aids-associated retrovirus

<400> SEQUENCE: 319
cacctgtcaa cataat                                               16

<210> SEQ ID NO 320
<211> LENGTH: 15
<212> TYPE: DNA
<213> ORGANISM: Aids-associated retrovirus

<400> SEQUENCE: 320
cctgtcaaca taatt                                                15

<210> SEQ ID NO 321
<211> LENGTH: 16
<212> TYPE: DNA
<213> ORGANISM: Aids-associated retrovirus

<400> SEQUENCE: 321
acctgtcaac ataatt                                               16

<210> SEQ ID NO 322
<211> LENGTH: 16
<212> TYPE: DNA
<213> ORGANISM: Aids-associated retrovirus

<400> SEQUENCE: 322
cctgtcaaca taattg                                               16

<210> SEQ ID NO 323
<211> LENGTH: 14
<212> TYPE: DNA
<213> ORGANISM: Aids-associated retrovirus

<400> SEQUENCE: 323
cctacacctg tcaa                                                 14

<210> SEQ ID NO 324
<211> LENGTH: 15
<212> TYPE: DNA
<213> ORGANISM: Aids-associated retrovirus

<400> SEQUENCE: 324
tgtcaacata attgg                                                15

<210> SEQ ID NO 325
<211> LENGTH: 16
<212> TYPE: DNA
<213> ORGANISM: Aids-associated retrovirus

<400> SEQUENCE: 325
tgtcaacata attgga                                               16

<210> SEQ ID NO 326
<211> LENGTH: 16
<212> TYPE: DNA
```

<213> ORGANISM: Aids-associated retrovirus

<400> SEQUENCE: 326
acacctttca acataa                                              16

<210> SEQ ID NO 327
<211> LENGTH: 16
<212> TYPE: DNA
<213> ORGANISM: Aids-associated retrovirus

<400> SEQUENCE: 327
tacacctttc aacata                                              16

<210> SEQ ID NO 328
<211> LENGTH: 18
<212> TYPE: DNA
<213> ORGANISM: Aids-associated retrovirus

<400> SEQUENCE: 328
acacctatca acataatg                                            18

<210> SEQ ID NO 329
<211> LENGTH: 17
<212> TYPE: DNA
<213> ORGANISM: Aids-associated retrovirus

<400> SEQUENCE: 329
acacctatca acataag                                             17

<210> SEQ ID NO 330
<211> LENGTH: 17
<212> TYPE: DNA
<213> ORGANISM: Aids-associated retrovirus

<400> SEQUENCE: 330
cacctgccaa tataatg                                             17

<210> SEQ ID NO 331
<211> LENGTH: 17
<212> TYPE: DNA
<213> ORGANISM: Aids-associated retrovirus

<400> SEQUENCE: 331
acacctgcca atataag                                             17

<210> SEQ ID NO 332
<211> LENGTH: 15
<212> TYPE: DNA
<213> ORGANISM: Aids-associated retrovirus

<400> SEQUENCE: 332
acgcccttca acata                                               15

<210> SEQ ID NO 333
<211> LENGTH: 16
<212> TYPE: DNA
<213> ORGANISM: Aids-associated retrovirus

<400> SEQUENCE: 333
cgcccttcaa cataag                                              16

<210> SEQ ID NO 334
<211> LENGTH: 15

```
<212> TYPE: DNA
<213> ORGANISM: Aids-associated retrovirus

<400> SEQUENCE: 334
tacgcccttc aacat                                               15

<210> SEQ ID NO 335
<211> LENGTH: 14
<212> TYPE: DNA
<213> ORGANISM: Aids-associated retrovirus

<400> SEQUENCE: 335
ctacaccggt caac                                                14

<210> SEQ ID NO 336
<211> LENGTH: 14
<212> TYPE: DNA
<213> ORGANISM: Aids-associated retrovirus

<400> SEQUENCE: 336
cctacaccgg tcaa                                                14

<210> SEQ ID NO 337
<211> LENGTH: 16
<212> TYPE: DNA
<213> ORGANISM: Aids-associated retrovirus

<400> SEQUENCE: 337
accggtcaac ataatg                                              16

<210> SEQ ID NO 338
<211> LENGTH: 16
<212> TYPE: DNA
<213> ORGANISM: Aids-associated retrovirus

<400> SEQUENCE: 338
accggtcaac ataatt                                              16

<210> SEQ ID NO 339
<211> LENGTH: 14
<212> TYPE: DNA
<213> ORGANISM: Aids-associated retrovirus

<400> SEQUENCE: 339
ctacaccagt caac                                                14

<210> SEQ ID NO 340
<211> LENGTH: 15
<212> TYPE: DNA
<213> ORGANISM: Aids-associated retrovirus

<400> SEQUENCE: 340
ctacaccagt caaca                                               15

<210> SEQ ID NO 341
<211> LENGTH: 15
<212> TYPE: DNA
<213> ORGANISM: Aids-associated retrovirus

<400> SEQUENCE: 341
acaccagtca acata                                               15

<210> SEQ ID NO 342
```

```
<211> LENGTH: 17
<212> TYPE: DNA
<213> ORGANISM: Aids-associated retrovirus

<400> SEQUENCE: 342
acaccagtca acataag                                                      17

<210> SEQ ID NO 343
<211> LENGTH: 15
<212> TYPE: DNA
<213> ORGANISM: Aids-associated retrovirus

<400> SEQUENCE: 343
tacgcctgtc aacat                                                        15

<210> SEQ ID NO 344
<211> LENGTH: 15
<212> TYPE: DNA
<213> ORGANISM: Aids-associated retrovirus

<400> SEQUENCE: 344
acgcctgtca acata                                                        15

<210> SEQ ID NO 345
<211> LENGTH: 14
<212> TYPE: DNA
<213> ORGANISM: Aids-associated retrovirus

<400> SEQUENCE: 345
tacgcctgtc aaca                                                         14

<210> SEQ ID NO 346
<211> LENGTH: 15
<212> TYPE: DNA
<213> ORGANISM: Aids-associated retrovirus

<400> SEQUENCE: 346
cctacacctt tcaac                                                        15

<210> SEQ ID NO 347
<211> LENGTH: 14
<212> TYPE: DNA
<213> ORGANISM: Aids-associated retrovirus

<400> SEQUENCE: 347
ctacaccttt caac                                                         14

<210> SEQ ID NO 348
<211> LENGTH: 15
<212> TYPE: DNA
<213> ORGANISM: Aids-associated retrovirus

<400> SEQUENCE: 348
acctacacct ttcaa                                                        15

<210> SEQ ID NO 349
<211> LENGTH: 18
<212> TYPE: DNA
<213> ORGANISM: Aids-associated retrovirus

<400> SEQUENCE: 349
acgcctgtca acataagg                                                     18
```

```
<210> SEQ ID NO 350
<211> LENGTH: 16
<212> TYPE: DNA
<213> ORGANISM: Aids-associated retrovirus

<400> SEQUENCE: 350
tacgcctgtc aacata                                                  16

<210> SEQ ID NO 351
<211> LENGTH: 17
<212> TYPE: DNA
<213> ORGANISM: Aids-associated retrovirus

<400> SEQUENCE: 351
cgcctgtcaa cataagg                                                 17

<210> SEQ ID NO 352
<211> LENGTH: 16
<212> TYPE: DNA
<213> ORGANISM: Aids-associated retrovirus

<400> SEQUENCE: 352
tacacctttc aacgta                                                  16

<210> SEQ ID NO 353
<211> LENGTH: 18
<212> TYPE: DNA
<213> ORGANISM: Aids-associated retrovirus

<400> SEQUENCE: 353
acacctttca acgtaagg                                                18

<210> SEQ ID NO 354
<211> LENGTH: 17
<212> TYPE: DNA
<213> ORGANISM: Aids-associated retrovirus

<400> SEQUENCE: 354
cacctttcaa cgtaatg                                                 17

<210> SEQ ID NO 355
<211> LENGTH: 16
<212> TYPE: DNA
<213> ORGANISM: Aids-associated retrovirus

<400> SEQUENCE: 355
acctttcaac gtaatt                                                  16

<210> SEQ ID NO 356
<211> LENGTH: 16
<212> TYPE: DNA
<213> ORGANISM: Aids-associated retrovirus

<400> SEQUENCE: 356
caacgtaatt ggaaga                                                  16

<210> SEQ ID NO 357
<211> LENGTH: 15
<212> TYPE: DNA
<213> ORGANISM: Aids-associated retrovirus

<400> SEQUENCE: 357
caacgtaatt ggaag                                                   15
```

```
<210> SEQ ID NO 358
<211> LENGTH: 16
<212> TYPE: DNA
<213> ORGANISM: Aids-associated retrovirus

<400> SEQUENCE: 358
aaatctgttg actcag                                                 16

<210> SEQ ID NO 359
<211> LENGTH: 17
<212> TYPE: DNA
<213> ORGANISM: Aids-associated retrovirus

<400> SEQUENCE: 359
gaaatctgtt gactcag                                                17

<210> SEQ ID NO 360
<211> LENGTH: 20
<212> TYPE: DNA
<213> ORGANISM: Aids-associated retrovirus

<400> SEQUENCE: 360
gaaatctgtt gactcagagg                                             20

<210> SEQ ID NO 361
<211> LENGTH: 19
<212> TYPE: DNA
<213> ORGANISM: Aids-associated retrovirus

<400> SEQUENCE: 361
aaatctgttg actcagagg                                              19

<210> SEQ ID NO 362
<211> LENGTH: 21
<212> TYPE: DNA
<213> ORGANISM: Aids-associated retrovirus

<400> SEQUENCE: 362
agaaatctgt tgactcagag g                                           21

<210> SEQ ID NO 363
<211> LENGTH: 21
<212> TYPE: DNA
<213> ORGANISM: Aids-associated retrovirus

<400> SEQUENCE: 363
agaaatctgt tgactcagat g                                           21

<210> SEQ ID NO 364
<211> LENGTH: 21
<212> TYPE: DNA
<213> ORGANISM: Aids-associated retrovirus

<400> SEQUENCE: 364
agaaatctgt tgactcagat t                                           21

<210> SEQ ID NO 365
<211> LENGTH: 23
<212> TYPE: DNA
<213> ORGANISM: Aids-associated retrovirus

<400> SEQUENCE: 365
agaaatctgt tgactcagat tgg                                         23
```

```
<210> SEQ ID NO 366
<211> LENGTH: 23
<212> TYPE: DNA
<213> ORGANISM: Aids-associated retrovirus

<400> SEQUENCE: 366
gaagaaatct gttgactcag agg                                          23

<210> SEQ ID NO 367
<211> LENGTH: 22
<212> TYPE: DNA
<213> ORGANISM: Aids-associated retrovirus

<400> SEQUENCE: 367
aagaaatctg ttgactcaga tg                                           22

<210> SEQ ID NO 368
<211> LENGTH: 21
<212> TYPE: DNA
<213> ORGANISM: Aids-associated retrovirus

<400> SEQUENCE: 368
agaaatctga tgactcagat g                                            21

<210> SEQ ID NO 369
<211> LENGTH: 21
<212> TYPE: DNA
<213> ORGANISM: Aids-associated retrovirus

<400> SEQUENCE: 369
agaaatctga tgactcagat t                                            21

<210> SEQ ID NO 370
<211> LENGTH: 22
<212> TYPE: DNA
<213> ORGANISM: Aids-associated retrovirus

<400> SEQUENCE: 370
aagaaatctg atgactcaga gg                                           22

<210> SEQ ID NO 371
<211> LENGTH: 23
<212> TYPE: DNA
<213> ORGANISM: Aids-associated retrovirus

<400> SEQUENCE: 371
gaagaaatct gatgactcag agg                                          23

<210> SEQ ID NO 372
<211> LENGTH: 22
<212> TYPE: DNA
<213> ORGANISM: Aids-associated retrovirus

<400> SEQUENCE: 372
aagaaatctg atgactcaga tg                                           22

<210> SEQ ID NO 373
<211> LENGTH: 23
<212> TYPE: DNA
<213> ORGANISM: Aids-associated retrovirus

<400> SEQUENCE: 373
```

-continued

| gaagaaatct gatgactcag att | 23 |

```
<210> SEQ ID NO 374
<211> LENGTH: 21
<212> TYPE: DNA
<213> ORGANISM: Aids-associated retrovirus

<400> SEQUENCE: 374
```

| ggaagaaatc tgatgactca g | 21 |

```
<210> SEQ ID NO 375
<211> LENGTH: 19
<212> TYPE: DNA
<213> ORGANISM: Aids-associated retrovirus

<400> SEQUENCE: 375
```

| aagaaatctg atgactcag | 19 |

```
<210> SEQ ID NO 376
<211> LENGTH: 21
<212> TYPE: DNA
<213> ORGANISM: Aids-associated retrovirus

<400> SEQUENCE: 376
```

| aaatctgatg actcagattg g | 21 |

```
<210> SEQ ID NO 377
<211> LENGTH: 20
<212> TYPE: DNA
<213> ORGANISM: Aids-associated retrovirus

<400> SEQUENCE: 377
```

| aaatctgatg actcagattg | 20 |

```
<210> SEQ ID NO 378
<211> LENGTH: 20
<212> TYPE: DNA
<213> ORGANISM: Aids-associated retrovirus

<400> SEQUENCE: 378
```

| aaatctgatg actcagcttg | 20 |

```
<210> SEQ ID NO 379
<211> LENGTH: 19
<212> TYPE: DNA
<213> ORGANISM: Aids-associated retrovirus

<400> SEQUENCE: 379
```

| aaatctgatg actcagctt | 19 |

```
<210> SEQ ID NO 380
<211> LENGTH: 19
<212> TYPE: DNA
<213> ORGANISM: Aids-associated retrovirus

<400> SEQUENCE: 380
```

| aatctgatga ctcagcttg | 19 |

```
<210> SEQ ID NO 381
<211> LENGTH: 20
<212> TYPE: DNA
<213> ORGANISM: Aids-associated retrovirus

<400> SEQUENCE: 381
```

```
aaatctgttg actcagcttg                                              20

<210> SEQ ID NO 382
<211> LENGTH: 19
<212> TYPE: DNA
<213> ORGANISM: Aids-associated retrovirus

<400> SEQUENCE: 382
aaatctgttg actcagctt                                               19

<210> SEQ ID NO 383
<211> LENGTH: 19
<212> TYPE: DNA
<213> ORGANISM: Aids-associated retrovirus

<400> SEQUENCE: 383
aatctgttga ctcagcttg                                               19

<210> SEQ ID NO 384
<211> LENGTH: 14
<212> TYPE: DNA
<213> ORGANISM: Aids-associated retrovirus

<400> SEQUENCE: 384
aatctgttga ctca                                                    14

<210> SEQ ID NO 385
<211> LENGTH: 15
<212> TYPE: DNA
<213> ORGANISM: Aids-associated retrovirus

<400> SEQUENCE: 385
aatctgttga ctcag                                                   15

<210> SEQ ID NO 386
<211> LENGTH: 15
<212> TYPE: DNA
<213> ORGANISM: Aids-associated retrovirus

<400> SEQUENCE: 386
aaatctgttg actca                                                   15

<210> SEQ ID NO 387
<211> LENGTH: 16
<212> TYPE: DNA
<213> ORGANISM: Aids-associated retrovirus

<400> SEQUENCE: 387
aaatctgttg actcag                                                  16

<210> SEQ ID NO 388
<211> LENGTH: 14
<212> TYPE: DNA
<213> ORGANISM: Aids-associated retrovirus

<400> SEQUENCE: 388
aatctgatga ctca                                                    14

<210> SEQ ID NO 389
<211> LENGTH: 15
<212> TYPE: DNA
<213> ORGANISM: Aids-associated retrovirus
```

```
<400> SEQUENCE: 389
aatctgatga ctcag                                                15

<210> SEQ ID NO 390
<211> LENGTH: 15
<212> TYPE: DNA
<213> ORGANISM: Aids-associated retrovirus

<400> SEQUENCE: 390
aaatctgatg actca                                                15

<210> SEQ ID NO 391
<211> LENGTH: 16
<212> TYPE: DNA
<213> ORGANISM: Aids-associated retrovirus

<400> SEQUENCE: 391
aaatctgatg actcag                                               16

<210> SEQ ID NO 392
<211> LENGTH: 15
<212> TYPE: DNA
<213> ORGANISM: Aids-associated retrovirus

<400> SEQUENCE: 392
gaaatctgtt gactc                                                15

<210> SEQ ID NO 393
<211> LENGTH: 15
<212> TYPE: DNA
<213> ORGANISM: Aids-associated retrovirus

<400> SEQUENCE: 393
gaactctgtt gactc                                                15

<210> SEQ ID NO 394
<211> LENGTH: 16
<212> TYPE: DNA
<213> ORGANISM: Aids-associated retrovirus

<400> SEQUENCE: 394
tctgttgact cagatg                                               16

<210> SEQ ID NO 395
<211> LENGTH: 15
<212> TYPE: DNA
<213> ORGANISM: Aids-associated retrovirus

<400> SEQUENCE: 395
gaaatctgtt gactc                                                15

<210> SEQ ID NO 396
<211> LENGTH: 15
<212> TYPE: DNA
<213> ORGANISM: Aids-associated retrovirus

<400> SEQUENCE: 396
gaactctgtt gactc                                                15

<210> SEQ ID NO 397
<211> LENGTH: 15
<212> TYPE: DNA
<213> ORGANISM: Aids-associated retrovirus
```

```
<400> SEQUENCE: 397
aaatctgttg actca                                                    15

<210> SEQ ID NO 398
<211> LENGTH: 15
<212> TYPE: DNA
<213> ORGANISM: Aids-associated retrovirus

<400> SEQUENCE: 398
aatctgttga ctcag                                                    15

<210> SEQ ID NO 399
<211> LENGTH: 15
<212> TYPE: DNA
<213> ORGANISM: Aids-associated retrovirus

<400> SEQUENCE: 399
aatctgatga ctcag                                                    15

<210> SEQ ID NO 400
<211> LENGTH: 15
<212> TYPE: DNA
<213> ORGANISM: Aids-associated retrovirus

<400> SEQUENCE: 400
aaatctgatg actca                                                    15

<210> SEQ ID NO 401
<211> LENGTH: 16
<212> TYPE: DNA
<213> ORGANISM: Aids-associated retrovirus

<400> SEQUENCE: 401
atctgttgac tcagag                                                   16

<210> SEQ ID NO 402
<211> LENGTH: 15
<212> TYPE: DNA
<213> ORGANISM: Aids-associated retrovirus

<400> SEQUENCE: 402
ctgttgactc agatt                                                    15

<210> SEQ ID NO 403
<211> LENGTH: 15
<212> TYPE: DNA
<213> ORGANISM: Aids-associated retrovirus

<400> SEQUENCE: 403
agaaatctgt tgact                                                    15

<210> SEQ ID NO 404
<211> LENGTH: 16
<212> TYPE: DNA
<213> ORGANISM: Aids-associated retrovirus

<400> SEQUENCE: 404
atctgatgac tcagag                                                   16

<210> SEQ ID NO 405
<211> LENGTH: 15
<212> TYPE: DNA
```

-continued

<213> ORGANISM: Aids-associated retrovirus

<400> SEQUENCE: 405
ctgatgactc agatt                                                    15

<210> SEQ ID NO 406
<211> LENGTH: 17
<212> TYPE: DNA
<213> ORGANISM: Aids-associated retrovirus

<400> SEQUENCE: 406
agaaatctga tgactca                                                  17

<210> SEQ ID NO 407
<211> LENGTH: 15
<212> TYPE: DNA
<213> ORGANISM: Aids-associated retrovirus

<400> SEQUENCE: 407
aatatgttga ctcag                                                    15

<210> SEQ ID NO 408
<211> LENGTH: 16
<212> TYPE: DNA
<213> ORGANISM: Aids-associated retrovirus

<400> SEQUENCE: 408
gaaatatgtt gactca                                                   16

<210> SEQ ID NO 409
<211> LENGTH: 15
<212> TYPE: DNA
<213> ORGANISM: Aids-associated retrovirus

<400> SEQUENCE: 409
aatttgttga ctcag                                                    15

<210> SEQ ID NO 410
<211> LENGTH: 16
<212> TYPE: DNA
<213> ORGANISM: Aids-associated retrovirus

<400> SEQUENCE: 410
gaaatttgtt gactca                                                   16

<210> SEQ ID NO 411
<211> LENGTH: 15
<212> TYPE: DNA
<213> ORGANISM: Aids-associated retrovirus

<400> SEQUENCE: 411
aatatgttga cccag                                                    15

<210> SEQ ID NO 412
<211> LENGTH: 15
<212> TYPE: DNA
<213> ORGANISM: Aids-associated retrovirus

<400> SEQUENCE: 412
aaatatgttg accca                                                    15

<210> SEQ ID NO 413
<211> LENGTH: 15

```
<212> TYPE: DNA
<213> ORGANISM: Aids-associated retrovirus

<400> SEQUENCE: 413
aatatgatga cccag                                                 15

<210> SEQ ID NO 414
<211> LENGTH: 15
<212> TYPE: DNA
<213> ORGANISM: Aids-associated retrovirus

<400> SEQUENCE: 414
acagatgatg accca                                                 15

<210> SEQ ID NO 415
<211> LENGTH: 15
<212> TYPE: DNA
<213> ORGANISM: Aids-associated retrovirus

<400> SEQUENCE: 415
aacatgttga ctcag                                                 15

<210> SEQ ID NO 416
<211> LENGTH: 16
<212> TYPE: DNA
<213> ORGANISM: Aids-associated retrovirus

<400> SEQUENCE: 416
aaacatgttg actcag                                                16

<210> SEQ ID NO 417
<211> LENGTH: 14
<212> TYPE: DNA
<213> ORGANISM: Aids-associated retrovirus

<400> SEQUENCE: 417
tgttgactca gctt                                                  14

<210> SEQ ID NO 418
<211> LENGTH: 15
<212> TYPE: DNA
<213> ORGANISM: Aids-associated retrovirus

<400> SEQUENCE: 418
ctgttgactc agctg                                                 15

<210> SEQ ID NO 419
<211> LENGTH: 14
<212> TYPE: DNA
<213> ORGANISM: Aids-associated retrovirus

<400> SEQUENCE: 419
ctatgactca gctt                                                  14

<210> SEQ ID NO 420
<211> LENGTH: 14
<212> TYPE: DNA
<213> ORGANISM: Aids-associated retrovirus

<400> SEQUENCE: 420
ctgatgactc agcg                                                  14

<210> SEQ ID NO 421
```

```
<211> LENGTH: 14
<212> TYPE: DNA
<213> ORGANISM: Aids-associated retrovirus

<400> SEQUENCE: 421
tgactacaca gctt                                                          14

<210> SEQ ID NO 422
<211> LENGTH: 14
<212> TYPE: DNA
<213> ORGANISM: Aids-associated retrovirus

<400> SEQUENCE: 422
ctgttgacac agcg                                                          14

<210> SEQ ID NO 423
<211> LENGTH: 15
<212> TYPE: DNA
<213> ORGANISM: Aids-associated retrovirus

<400> SEQUENCE: 423
aatctgttga cacag                                                         15

<210> SEQ ID NO 424
<211> LENGTH: 14
<212> TYPE: DNA
<213> ORGANISM: Aids-associated retrovirus

<400> SEQUENCE: 424
aacctgttga ctca                                                          14

<210> SEQ ID NO 425
<211> LENGTH: 14
<212> TYPE: DNA
<213> ORGANISM: Aids-associated retrovirus

<400> SEQUENCE: 425
aaacctgttg actc                                                          14

<210> SEQ ID NO 426
<211> LENGTH: 14
<212> TYPE: DNA
<213> ORGANISM: Aids-associated retrovirus

<400> SEQUENCE: 426
gaaacctgtt gact                                                          14

<210> SEQ ID NO 427
<211> LENGTH: 15
<212> TYPE: DNA
<213> ORGANISM: Aids-associated retrovirus

<400> SEQUENCE: 427
tgttgactca gattg                                                         15

<210> SEQ ID NO 428
<211> LENGTH: 17
<212> TYPE: DNA
<213> ORGANISM: Aids-associated retrovirus

<400> SEQUENCE: 428
tgttgactca gattggg                                                       17
```

```
<210> SEQ ID NO 429
<211> LENGTH: 16
<212> TYPE: DNA
<213> ORGANISM: Aids-associated retrovirus

<400> SEQUENCE: 429
gttgactcag attggg                                                  16

<210> SEQ ID NO 430
<211> LENGTH: 15
<212> TYPE: DNA
<213> ORGANISM: Aids-associated retrovirus

<400> SEQUENCE: 430
tgttgacaca gcttg                                                   15

<210> SEQ ID NO 431
<211> LENGTH: 15
<212> TYPE: DNA
<213> ORGANISM: Aids-associated retrovirus

<400> SEQUENCE: 431
ctgttgacac agctt                                                   15

<210> SEQ ID NO 432
<211> LENGTH: 16
<212> TYPE: DNA
<213> ORGANISM: Aids-associated retrovirus

<400> SEQUENCE: 432
gttgacacag cttggg                                                  16

<210> SEQ ID NO 433
<211> LENGTH: 15
<212> TYPE: DNA
<213> ORGANISM: Aids-associated retrovirus

<400> SEQUENCE: 433
tgttgactca gcttg                                                   15

<210> SEQ ID NO 434
<211> LENGTH: 13
<212> TYPE: DNA
<213> ORGANISM: Aids-associated retrovirus

<400> SEQUENCE: 434
gttgactcag atg                                                     13

<210> SEQ ID NO 435
<211> LENGTH: 14
<212> TYPE: DNA
<213> ORGANISM: Aids-associated retrovirus

<400> SEQUENCE: 435
gttgactcag cttg                                                    14

<210> SEQ ID NO 436
<211> LENGTH: 15
<212> TYPE: DNA
<213> ORGANISM: Aids-associated retrovirus

<400> SEQUENCE: 436
tgttgaccca gattg                                                   15
```

```
<210> SEQ ID NO 437
<211> LENGTH: 14
<212> TYPE: DNA
<213> ORGANISM: Aids-associated retrovirus

<400> SEQUENCE: 437
gttgacccag attg                                                    14

<210> SEQ ID NO 438
<211> LENGTH: 16
<212> TYPE: DNA
<213> ORGANISM: Aids-associated retrovirus

<400> SEQUENCE: 438
gttgacccag attggg                                                  16

<210> SEQ ID NO 439
<211> LENGTH: 15
<212> TYPE: DNA
<213> ORGANISM: Aids-associated retrovirus

<400> SEQUENCE: 439
tgatgactca gattg                                                   15

<210> SEQ ID NO 440
<211> LENGTH: 17
<212> TYPE: DNA
<213> ORGANISM: Aids-associated retrovirus

<400> SEQUENCE: 440
tgatgactca gattggg                                                 17

<210> SEQ ID NO 441
<211> LENGTH: 16
<212> TYPE: DNA
<213> ORGANISM: Aids-associated retrovirus

<400> SEQUENCE: 441
gatgactcag attggg                                                  16

<210> SEQ ID NO 442
<211> LENGTH: 16
<212> TYPE: DNA
<213> ORGANISM: Aids-associated retrovirus

<400> SEQUENCE: 442
gatgactcag attggt                                                  16

<210> SEQ ID NO 443
<211> LENGTH: 15
<212> TYPE: DNA
<213> ORGANISM: Aids-associated retrovirus

<400> SEQUENCE: 443
ctgatgactc agctt                                                   15

<210> SEQ ID NO 444
<211> LENGTH: 15
<212> TYPE: DNA
<213> ORGANISM: Aids-associated retrovirus

<400> SEQUENCE: 444
tgatgactca gcttg                                                   15
```

<210> SEQ ID NO 445
<211> LENGTH: 15
<212> TYPE: DNA
<213> ORGANISM: Aids-associated retrovirus

<400> SEQUENCE: 445
aaatctgttg actca                                    15

<210> SEQ ID NO 446
<211> LENGTH: 15
<212> TYPE: DNA
<213> ORGANISM: Aids-associated retrovirus

<400> SEQUENCE: 446
aaatctgttg actca                                    15

<210> SEQ ID NO 447
<211> LENGTH: 15
<212> TYPE: DNA
<213> ORGANISM: Aids-associated retrovirus

<400> SEQUENCE: 447
aaatctgttg actca                                    15

<210> SEQ ID NO 448
<211> LENGTH: 15
<212> TYPE: DNA
<213> ORGANISM: Aids-associated retrovirus

<400> SEQUENCE: 448
aatctgatga ctcag                                    15

<210> SEQ ID NO 449
<211> LENGTH: 15
<212> TYPE: DNA
<213> ORGANISM: Aids-associated retrovirus

<400> SEQUENCE: 449
aaatctgatg actca                                    15

<210> SEQ ID NO 450
<211> LENGTH: 15
<212> TYPE: DNA
<213> ORGANISM: Aids-associated retrovirus

<400> SEQUENCE: 450
gaaatctgat gactc                                    15

<210> SEQ ID NO 451
<211> LENGTH: 15
<212> TYPE: DNA
<213> ORGANISM: Aids-associated retrovirus

<400> SEQUENCE: 451
ctgatgactc agatg                                    15

<210> SEQ ID NO 452
<211> LENGTH: 12
<212> TYPE: DNA
<213> ORGANISM: Aids-associated retrovirus

<400> SEQUENCE: 452

```
agaaatatga tg                                                         12

<210> SEQ ID NO 453
<211> LENGTH: 16
<212> TYPE: DNA
<213> ORGANISM: Aids-associated retrovirus

<400> SEQUENCE: 453
aagaaatatg atgact                                                     16

<210> SEQ ID NO 454
<211> LENGTH: 16
<212> TYPE: DNA
<213> ORGANISM: Aids-associated retrovirus

<400> SEQUENCE: 454
aagaaatctg atgact                                                     16

<210> SEQ ID NO 455
<211> LENGTH: 16
<212> TYPE: DNA
<213> ORGANISM: Aids-associated retrovirus

<400> SEQUENCE: 455
aagaaatata atgact                                                     16

<210> SEQ ID NO 456
<211> LENGTH: 16
<212> TYPE: DNA
<213> ORGANISM: Aids-associated retrovirus

<400> SEQUENCE: 456
aaatataatg actcag                                                     16

<210> SEQ ID NO 457
<211> LENGTH: 15
<212> TYPE: DNA
<213> ORGANISM: Aids-associated retrovirus

<400> SEQUENCE: 457
aatatgatga cccag                                                      15

<210> SEQ ID NO 458
<211> LENGTH: 15
<212> TYPE: DNA
<213> ORGANISM: Aids-associated retrovirus

<400> SEQUENCE: 458
aacctgatga ctcag                                                      15

<210> SEQ ID NO 459
<211> LENGTH: 16
<212> TYPE: DNA
<213> ORGANISM: Aids-associated retrovirus

<400> SEQUENCE: 459
agaaatttga tgactc                                                     16

<210> SEQ ID NO 460
<211> LENGTH: 19
<212> TYPE: DNA
<213> ORGANISM: Aids-associated retrovirus

<400> SEQUENCE: 460
```

```
aaatttgatg actatgact                                              19

<210> SEQ ID NO 461
<211> LENGTH: 14
<212> TYPE: DNA
<213> ORGANISM: Aids-associated retrovirus

<400> SEQUENCE: 461
acctgatgac tcag                                                   14

<210> SEQ ID NO 462
<211> LENGTH: 16
<212> TYPE: DNA
<213> ORGANISM: Aids-associated retrovirus

<400> SEQUENCE: 462
aatctgatga ctcaga                                                 16

<210> SEQ ID NO 463
<211> LENGTH: 17
<212> TYPE: DNA
<213> ORGANISM: Aids-associated retrovirus

<400> SEQUENCE: 463
atctgatgac tcagatg                                                17

<210> SEQ ID NO 464
<211> LENGTH: 14
<212> TYPE: DNA
<213> ORGANISM: Aids-associated retrovirus

<400> SEQUENCE: 464
atctgatgac tcag                                                   14

<210> SEQ ID NO 465
<211> LENGTH: 16
<212> TYPE: DNA
<213> ORGANISM: Aids-associated retrovirus

<400> SEQUENCE: 465
ctgatgactc agattg                                                 16

<210> SEQ ID NO 466
<211> LENGTH: 16
<212> TYPE: DNA
<213> ORGANISM: Aids-associated retrovirus

<400> SEQUENCE: 466
agaaatctga tgactc                                                 16

<210> SEQ ID NO 467
<211> LENGTH: 15
<212> TYPE: DNA
<213> ORGANISM: Aids-associated retrovirus

<400> SEQUENCE: 467
agaaatctga tgact                                                  15

<210> SEQ ID NO 468
<211> LENGTH: 15
<212> TYPE: DNA
<213> ORGANISM: Aids-associated retrovirus
```

```
<400> SEQUENCE: 468
gaagaaatct gatga                                              15

<210> SEQ ID NO 469
<211> LENGTH: 16
<212> TYPE: DNA
<213> ORGANISM: Aids-associated retrovirus

<400> SEQUENCE: 469
ggaagaaatc tgatga                                             16

<210> SEQ ID NO 470
<211> LENGTH: 16
<212> TYPE: DNA
<213> ORGANISM: Aids-associated retrovirus

<400> SEQUENCE: 470
gaagaaatct gatgac                                             16

<210> SEQ ID NO 471
<211> LENGTH: 14
<212> TYPE: DNA
<213> ORGANISM: Aids-associated retrovirus

<400> SEQUENCE: 471
agaaatctga tgac                                               14

<210> SEQ ID NO 472
<211> LENGTH: 15
<212> TYPE: DNA
<213> ORGANISM: Aids-associated retrovirus

<400> SEQUENCE: 472
aatctgttaa ctcag                                              15

<210> SEQ ID NO 473
<211> LENGTH: 16
<212> TYPE: DNA
<213> ORGANISM: Aids-associated retrovirus

<400> SEQUENCE: 473
tctgttaact cagatt                                             16

<210> SEQ ID NO 474
<211> LENGTH: 16
<212> TYPE: DNA
<213> ORGANISM: Aids-associated retrovirus

<400> SEQUENCE: 474
atctgttaac tcagag                                             16

<210> SEQ ID NO 475
<211> LENGTH: 15
<212> TYPE: DNA
<213> ORGANISM: Aids-associated retrovirus

<400> SEQUENCE: 475
agaaatttgt tgact                                              15

<210> SEQ ID NO 476
<211> LENGTH: 15
<212> TYPE: DNA
<213> ORGANISM: Aids-associated retrovirus
```

```
<400> SEQUENCE: 476
gaaatttgtt gactc                                                  15

<210> SEQ ID NO 477
<211> LENGTH: 15
<212> TYPE: DNA
<213> ORGANISM: Aids-associated retrovirus

<400> SEQUENCE: 477
aatttgttga ctcag                                                  15

<210> SEQ ID NO 478
<211> LENGTH: 24
<212> TYPE: DNA
<213> ORGANISM: Aids-associated retrovirus

<400> SEQUENCE: 478
ggaggtttta tcaaagtcag acaa                                        24

<210> SEQ ID NO 479
<211> LENGTH: 24
<212> TYPE: DNA
<213> ORGANISM: Aids-associated retrovirus

<400> SEQUENCE: 479
ggaggtttca ttaaggtaaa acag                                        24

<210> SEQ ID NO 480
<211> LENGTH: 24
<212> TYPE: DNA
<213> ORGANISM: Aids-associated retrovirus

<400> SEQUENCE: 480
ggaggtttta ttaaggtaag acag                                        24

<210> SEQ ID NO 481
<211> LENGTH: 24
<212> TYPE: DNA
<213> ORGANISM: Aids-associated retrovirus

<400> SEQUENCE: 481
ggaggtttta ttaaagtaag acaa                                        24

<210> SEQ ID NO 482
<211> LENGTH: 24
<212> TYPE: DNA
<213> ORGANISM: Aids-associated retrovirus

<400> SEQUENCE: 482
ggaggcttta tcaaagtaag acaa                                        24

<210> SEQ ID NO 483
<211> LENGTH: 24
<212> TYPE: DNA
<213> ORGANISM: Aids-associated retrovirus

<400> SEQUENCE: 483
ggaggtttta tcaaagtcag acaa                                        24

<210> SEQ ID NO 484
<211> LENGTH: 26
<212> TYPE: DNA
```

```
<213> ORGANISM: Aids-associated retrovirus

<400> SEQUENCE: 484
ggacctacac cggtcaacat aattgg                                    26

<210> SEQ ID NO 485
<211> LENGTH: 26
<212> TYPE: DNA
<213> ORGANISM: Aids-associated retrovirus

<400> SEQUENCE: 485
ggacctacac ctgccaatat aattgg                                    26

<210> SEQ ID NO 486
<211> LENGTH: 26
<212> TYPE: DNA
<213> ORGANISM: Aids-associated retrovirus

<400> SEQUENCE: 486
ggacctacgc ccttcaacat aattgg                                    26

<210> SEQ ID NO 487
<211> LENGTH: 26
<212> TYPE: DNA
<213> ORGANISM: Aids-associated retrovirus

<400> SEQUENCE: 487
ggaccgacac ctgtcaccat aattgg                                    26

<210> SEQ ID NO 488
<211> LENGTH: 26
<212> TYPE: DNA
<213> ORGANISM: Aids-associated retrovirus

<400> SEQUENCE: 488
ggacctatac ctgtcaacat aattgg                                    26

<210> SEQ ID NO 489
<211> LENGTH: 25
<212> TYPE: DNA
<213> ORGANISM: Aids-associated retrovirus

<400> SEQUENCE: 489
aaaaaatctg atgactcaga ttggc                                     25

<210> SEQ ID NO 490
<211> LENGTH: 25
<212> TYPE: DNA
<213> ORGANISM: Aids-associated retrovirus

<400> SEQUENCE: 490
aagaactctg ttgactcagc ttgga                                     25

<210> SEQ ID NO 491
<211> LENGTH: 25
<212> TYPE: DNA
<213> ORGANISM: Aids-associated retrovirus

<400> SEQUENCE: 491
aagaaatatg atgacccagc ttggc                                     25

<210> SEQ ID NO 492
<211> LENGTH: 25
```

```
<212> TYPE: DNA
<213> ORGANISM: Aids-associated retrovirus

<400> SEQUENCE: 492
aagaaatata atgactcagc ttgga                               25

<210> SEQ ID NO 493
<211> LENGTH: 25
<212> TYPE: DNA
<213> ORGANISM: Aids-associated retrovirus

<400> SEQUENCE: 493
aagaaatctg ctgactcaga ttggg                               25

<210> SEQ ID NO 494
<211> LENGTH: 25
<212> TYPE: DNA
<213> ORGANISM: Aids-associated retrovirus

<400> SEQUENCE: 494
aagaaatctg ttgacacagc ttggc                               25

<210> SEQ ID NO 495
<211> LENGTH: 25
<212> TYPE: DNA
<213> ORGANISM: Aids-associated retrovirus

<400> SEQUENCE: 495
aagaaatatg ttgactcagc ttggt                               25

<210> SEQ ID NO 496
<211> LENGTH: 25
<212> TYPE: DNA
<213> ORGANISM: Aids-associated retrovirus

<400> SEQUENCE: 496
aagaaatttg ttgactcaga ttggg                               25

<210> SEQ ID NO 497
<211> LENGTH: 25
<212> TYPE: DNA
<213> ORGANISM: Aids-associated retrovirus

<400> SEQUENCE: 497
aagaaatatg ttgactcagc ttggt                               25

<210> SEQ ID NO 498
<211> LENGTH: 25
<212> TYPE: DNA
<213> ORGANISM: Aids-associated retrovirus

<400> SEQUENCE: 498
aagaaatatg ttgactcagc ttgga                               25

<210> SEQ ID NO 499
<211> LENGTH: 25
<212> TYPE: DNA
<213> ORGANISM: Aids-associated retrovirus

<400> SEQUENCE: 499
aagaaatctg ttgactcagc ttgga                               25

<210> SEQ ID NO 500
```

```
<211> LENGTH: 25
<212> TYPE: DNA
<213> ORGANISM: Aids-associated retrovirus

<400> SEQUENCE: 500
aagaaacctg ttgactcaac ttggt                                    25

<210> SEQ ID NO 501
<211> LENGTH: 21
<212> TYPE: DNA
<213> ORGANISM: Aids-associated retrovirus

<400> SEQUENCE: 501
cagagccaac agccccacca g                                        21

<210> SEQ ID NO 502
<211> LENGTH: 26
<212> TYPE: DNA
<213> ORGANISM: Aids-associated retrovirus

<400> SEQUENCE: 502 tttcttctg tcaatggcca ttgttt                                    26

<210> SEQ ID NO 503
<211> LENGTH: 23
<212> TYPE: DNA
<213> ORGANISM: Aids-associated retrovirus

<400> SEQUENCE: 503
cctcaaatca ctctttggca acg                                      23

<210> SEQ ID NO 504
<211> LENGTH: 23
<212> TYPE: DNA
<213> ORGANISM: Aids-associated retrovirus

<400> SEQUENCE: 504
cctcagatca ctctttggca acg                                      23

<210> SEQ ID NO 505
<211> LENGTH: 20
<212> TYPE: DNA
<213> ORGANISM: Aids-associated retrovirus

<400> SEQUENCE: 505
cctgtcaaca taattgcaag                                          20

<210> SEQ ID NO 506
<211> LENGTH: 25
<212> TYPE: DNA
<213> ORGANISM: Aids-associated retrovirus

<400> SEQUENCE: 506
ctggtacagt ttcaataggg ctaat                                    25

<210> SEQ ID NO 507
<211> LENGTH: 25
<212> TYPE: DNA
<213> ORGANISM: Aids-associated retrovirus

<400> SEQUENCE: 507
ctggtacagt ttcaatagga ctaat                                    25
```

-continued

```
<210> SEQ ID NO 508
<211> LENGTH: 25
<212> TYPE: DNA
<213> ORGANISM: Aids-associated retrovirus

<400> SEQUENCE: 508
ctggtacagt ctcaatagga ctaat                                            25

<210> SEQ ID NO 509
<211> LENGTH: 25
<212> TYPE: DNA
<213> ORGANISM: Aids-associated retrovirus

<400> SEQUENCE: 509
ctggtacagt ctcaataggg ctaat                                            25

<210> SEQ ID NO 510
<211> LENGTH: 14
<212> TYPE: DNA
<213> ORGANISM: Aids-associated retrovirus

<400> SEQUENCE: 510
gtcatcagat ttct                                                        14

<210> SEQ ID NO 511
<211> LENGTH: 20
<212> TYPE: DNA
<213> ORGANISM: Aids-associated retrovirus

<400> SEQUENCE: 511 aggggggaatt ggaggtttta                                                 20

<210> SEQ ID NO 512
<211> LENGTH: 15
<212> TYPE: DNA
<213> ORGANISM: Aids-associated retrovirus

<400> SEQUENCE: 512
atgatagggg gaatt                                                       15

<210> SEQ ID NO 513
<211> LENGTH: 14
<212> TYPE: DNA
<213> ORGANISM: Aids-associated retrovirus

<400> SEQUENCE: 513
aagaatgata gggg                                                        14

<210> SEQ ID NO 514
<211> LENGTH: 15
<212> TYPE: DNA
<213> ORGANISM: Aids-associated retrovirus

<400> SEQUENCE: 514
tctgttgact cagat                                                       15

<210> SEQ ID NO 515
<211> LENGTH: 15
<212> TYPE: DNA
<213> ORGANISM: Aids-associated retrovirus

<400> SEQUENCE: 515
gagtcaacag agttc                                                       15
```

<210> SEQ ID NO 516
<211> LENGTH: 15
<212> TYPE: DNA
<213> ORGANISM: Aids-associated retrovirus

<400> SEQUENCE: 516
aggttttgcc aaagt                                                    15

<210> SEQ ID NO 517
<211> LENGTH: 17
<212> TYPE: DNA
<213> ORGANISM: Aids-associated retrovirus

<400> SEQUENCE: 517
acacctatca acataat                                                  17

<210> SEQ ID NO 518
<211> LENGTH: 15
<212> TYPE: DNA
<213> ORGANISM: Aids-associated retrovirus

<400> SEQUENCE: 518
acacctacca acata                                                    15

<210> SEQ ID NO 519
<211> LENGTH: 14
<212> TYPE: DNA
<213> ORGANISM: Aids-associated retrovirus

<400> SEQUENCE: 519
acacctacca acgt                                                     14

<210> SEQ ID NO 520
<211> LENGTH: 30
<212> TYPE: DNA
<213> ORGANISM: AIDS-associated retrovirus

<400> SEQUENCE: 520
acaggagcag atgatacagt attagaagaa                                    30

<210> SEQ ID NO 521
<211> LENGTH: 33
<212> TYPE: DNA
<213> ORGANISM: AIDS-associated retrovirus

<400> SEQUENCE: 521
ccaaaaatga tagggggaat tggaggtttt atc                                33

<210> SEQ ID NO 522
<211> LENGTH: 30
<212> TYPE: DNA
<213> ORGANISM: AIDS-associated retrovirus

<400> SEQUENCE: 522
aaaatgatag ggggaattgg aggttttatc                                    30

<210> SEQ ID NO 523
<211> LENGTH: 24
<212> TYPE: DNA
<213> ORGANISM: AIDS-associated retrovirus

<400> SEQUENCE: 523
ggaggtttta tcaaagtaag acag                                          24

<210> SEQ ID NO 524
<211> LENGTH: 30
<212> TYPE: DNA
<213> ORGANISM: AIDS-associated retrovirus

<400> SEQUENCE: 524
ggacctacac ctgtcaacat aaatggaaga                30

<210> SEQ ID NO 525
<211> LENGTH: 27
<212> TYPE: DNA
<213> ORGANISM: AIDS-associated retrovirus

<400> SEQUENCE: 525
ggaagaaatc tgttgactca gattggt                27

<210> SEQ ID NO 526
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 526
cctcaratca ctctttggga acg                23

<210> SEQ ID NO 527
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 527
taaccttctt tagacaactg a                21

<210> SEQ ID NO 528
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 528
cctgtcaaca taattggaag                20

<210> SEQ ID NO 529
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 529
taatcrggat aactytgaca tggtc                25